(12) United States Patent
Schorge et al.

(10) Patent No.: US 11,779,658 B2
(45) Date of Patent: Oct. 10, 2023

(54) EXPRESSION VECTORS COMPRISING ENGINEERED GENES

(71) Applicant: UCL BUSINESS LTD, London (GB)

(72) Inventors: Stephanie Schorge, London (GB); Matthew Charles Walker, London (GB); Dimitri M. Kullmann, London (GB); Albert Snowball, London (GB); Elodie Chabrol, London (GB)

(73) Assignee: UCL BUSINESS LTD, London (GB)

( * ) Notice: Subject to any disclaimer, the term of this patent is extended or adjusted under 35 U.S.C. 154(b) by 801 days.

(21) Appl. No.: 16/622,800

(22) PCT Filed: Jun. 15, 2018

(86) PCT No.: PCT/EP2018/065953
§ 371 (c)(1),
(2) Date: Dec. 13, 2019

(87) PCT Pub. No.: WO2018/229254
PCT Pub. Date: Dec. 20, 2018

(65) Prior Publication Data
US 2021/0000977 A1 Jan. 7, 2021

(30) Foreign Application Priority Data
Jun. 15, 2017 (GB) .................... 1709551

(51) Int. Cl.
*A61K 48/00* (2006.01)
*C12N 15/86* (2006.01)
*C07K 14/705* (2006.01)
*A61K 38/17* (2006.01)
*A61P 25/08* (2006.01)
*C12Q 1/6876* (2018.01)

(52) U.S. Cl.
CPC ........ *A61K 48/0058* (2013.01); *A61K 38/177* (2013.01); *A61P 25/08* (2018.01); *C07K 14/705* (2013.01); *C12N 15/86* (2013.01); *C12Q 1/6876* (2013.01); *C12N 2740/15043* (2013.01); *C12N 2740/15052* (2013.01); *C12N 2830/008* (2013.01); *C12Q 2600/158* (2013.01)

(58) Field of Classification Search
CPC ... A61K 48/0058; A61K 38/177; A61P 25/08; C07K 14/705; C12N 15/86; C12N 2740/15043; C12N 2740/15052; C12N 2830/008; C12Q 1/6876; C12Q 2600/158
See application file for complete search history.

(56) References Cited

U.S. PATENT DOCUMENTS 10,463,751 B2 * 11/2019 De Fougerolles ...... A61P 11/00

FOREIGN PATENT DOCUMENTS

WO WO-2012027358 A1 * 3/2012 ......... A61K 49/0017
WO 2015136247 9/2015

OTHER PUBLICATIONS

Streit AK, Matschke LA, Dolga AM, Rinné S, Decher N. RNA editing in the central cavity as a mechanism to regulate surface expression of the voltage-gated potassium channel Kv1. 1. Journal of Biological Chemistry. Sep. 1, 2014;289(39):26762-71 (Year: 2014).*
GenBank AAA36139.1; Apr. 27, 1993 (Year: 1993).*
Alignment of SEQ ID No. 2 (Qy) and GenBank #AAA36139.1 (Db), Jul. 29, 2022 (Year: 2022).*
D'Adamo et al. New insights into the pathogenesis and therapeutics of episodic ataxia type 1. Front. Cell. Neurosci. 2015; 9:317. (Year: 2015).*
Neurologic Diseases. downloaded from https://medlineplus.gov/neurologicdiseases.html, downloaded on Nov. 15, 2022. Published on Sep. 29, 2014. (Year: 2014).*
NCBI Reference Sequence: NP_000208.2. Downloaded from https://ncbi.nlm.nih.gov/protein/NP_000208.2, downloaded on Nov. 15, 2022, First published in 1990. (Year: 1990).*
Dittgen et al. Lentivirus-based genetic manipulations of cortical neurons and their optical and electrophysiological monitoring in vivo. PNAS, 2004, 101(52): 18206-18211. (Year: 2004).*
Wang et al. Identification of the RA response element and transcriptional silencer in human aCaMKII promoter. Mol Biol Rep. 2008, 35:37-44. (Year: 2008).*
Sequence comparison between US-16-622-800A-3 and human CAMK2A gene promoter region GenBank DQ399941.1. Downloaded from https://www.ncbi.nlm.nih.gov/nuccore/DQ399941, downloaded on Nov. 16, 2022. First published in 2008. Comparison done on Nov. 16, 2022. (Year: 2022).*
NCBI sequence alignment between Cohen-hCAMK2Apro-Guild KCNA1 versus SEQ ID No. 9. Alignment done on Nov. 22, 2022. (Year: 2022).*

(Continued)

*Primary Examiner* — Arthur S Leonard
*Assistant Examiner* — Jianjian Zhu
(74) *Attorney, Agent, or Firm* — Quarles & Brady, LLP

(57) ABSTRACT

The invention provides expression vectors, nucleic acids, vector particles and methods of treatment involving these vector particles, comprising an engineered KCNA1 gene encoding an edited Kv1.1 potassium channel, as well as methods of confirming the presence of engineered KCNA1 mRNA in a cell. The features of the engineered KCNA1 gene combine to advantageously enhance the translation and activity of the Kv1.1 protein and improve detection of KCNA1 gene expression in a cell and can be used for example in the treatment of epilepsy and similar neurological disorders.

Figure 1:
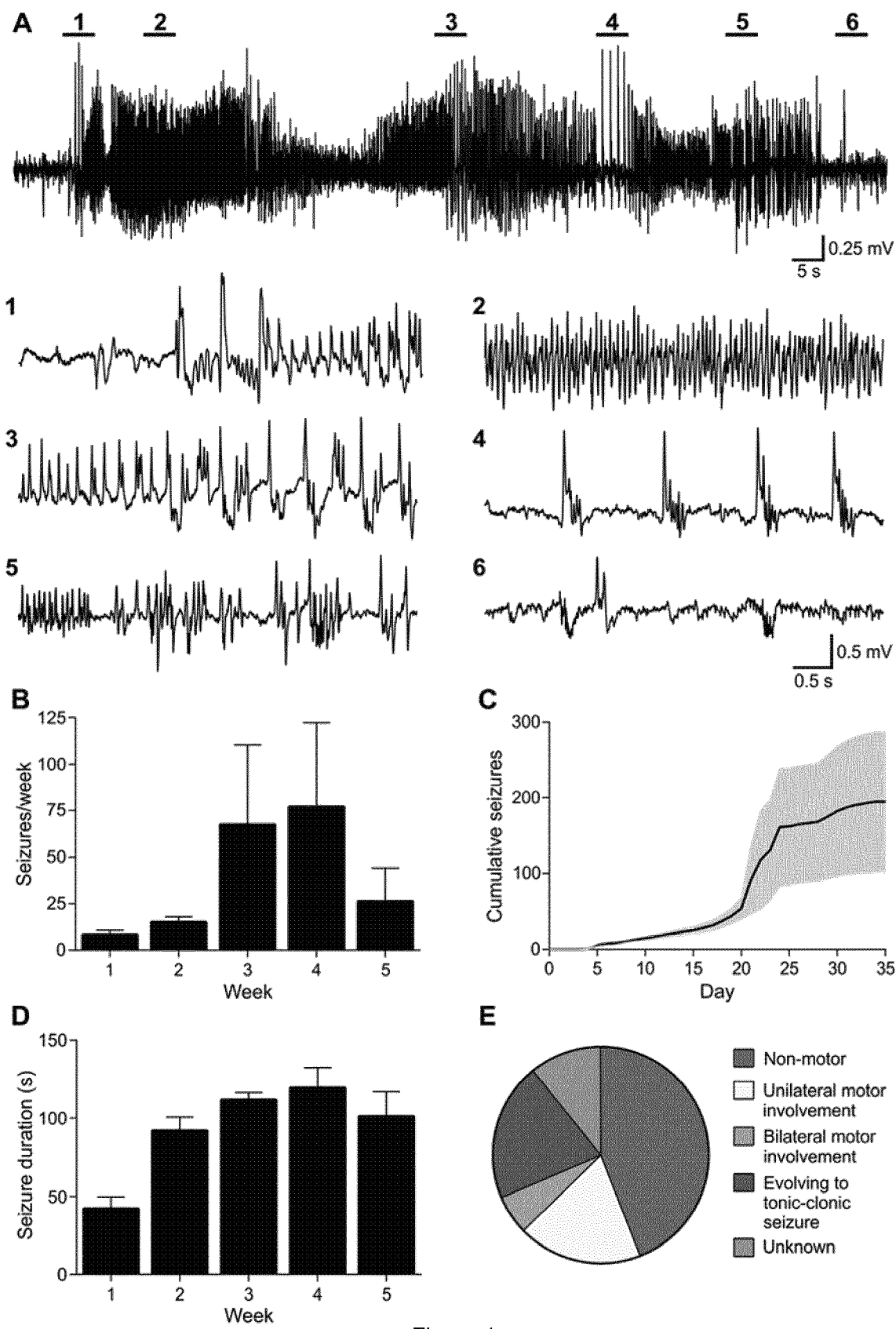

25 Claims, 7 Drawing Sheets
Specification includes a Sequence Listing.

(56) References Cited

OTHER PUBLICATIONS

Accession No. GAMP01000630.1, Database GenBank [online], Aug. 22, 2013 [Retrieved on Jan. 20, 2022], Retrieved from the Internet, URL:<https://www.ncbi.nlm.nih.gov/nuccore/532523515>.
Streit, A.K. et al., RNA Editing in the Central Cavity as a Mechanism to Regulate Surface Expression of the Voltage-gated Potassium Channel Kv1. 1. The Journal of Biological Chemistry (2014) 289(39):26762-26771.
D'Adamo, M.C. et al., K+ channelepsy: progress in the neurobiology of potassium channels and epilepsy Front. Cell. Neurosci. (2013) 7, Art. 134.
Wykes, R.C. & Lignani, G. Gene therapy and editing: Novel potential treatments for neuronal Channelopathies. Neuropharmacology (2018) 132:108-117.
Wykes, R.C. et al., Lentiviral-mediated over-expression of the potassium channel Kv1.1 as a treatment for focal neocortical epilepsy. Soc. Neurosci. Abstract Viewer (2011) vol. 41.
Heeroma, J.H. et al., Episodic ataxia type 1 mutations differentially affect neuronal excitability and transmitter release. Disease Models & Mechanisms (2009) 2:612-619 doi:10.1242/dmm.003582.
Snowball, A. et al., Epilepsy Gene Therapy Using an Engineered Potassium Channel. Journal of Neuroscience (2019) 39(16):3159-3169.
Kätzel, D. et al., Chemical-genetic attenuation of focal neocortical seizures. Nat. Commun. (2014) 5:3847.
Colasante, G, et al., In vivo CRISPRa decreases seizures and rescues cognitive deficits in a rodent model of epilepsy. Brain. (2020) 143(3):891-905. doi: 10.1093/brain/awaa045.
Bhalla, T., et al. "Control of human potassium channel inactivation by editing of a small mRNA hairpin." Nature structural & molecular biology 11.10 (2004): 950-956.
Database UniProt. Nov. 13, 2013. SubName: Full=Potassium voltage-gated channel shaker-related subfamily, member 1 (ECO:0000313 | EMBL:AAI12971.1). Database Accession No. Q2KHP0 Sequence.
Database UniProt. Nov. 13, 2013. SubName: Full=Potassium voltage-gated channel subfamily A member 1 (ECO:0000313 | EMBL:JAB52125.1). Database Accession No. U3FYB1 Sequence.
International Searching Authority. International Search Report and Written Opinion for application PCT/EP2018-065953, dated Jul. 30, 2018.
Snowball, A. et al. "Changing channels in pain and epilepsy: Exploiting ion channel gene therapy for disorders of neuronal hyperexcitability." FEBS letters 589.14 (2015): 1620-1634.
Streit, A. K., et al. "RNA editing of Kv1. 1 channels may account for reduced ictogenic potential of 4-aminopyridine in chronic epileptic rats." Epilepsia 52.3 (2011): 645-648.
Wykes, R. C., et al. "Lentivector-Mediated Potassium Channel Overexpression Decreases Focal Cortical Seizure Frequency." Epilepsia. vol. 58. No. Suppl. 5, Sp. Iss. SI, Dec. 2017, p. S25.
Wykes, R. C., et al. "Optogenetic and potassium channel gene therapy in a rodent model of focal neocortical epilepsy." Science translational medicine 4.161 (2012): 161ra152-161ra152.

* cited by examiner

EXPRESSION VECTORS COMPRISING ENGINEERED GENES

This application is a national stage filing under 35 U.S.C. 371 of International Application No. PCT/EP2018/065953, filed Jun. 15, 2018, which claims priority from Great Britain Application No. GB1709551.4, filed 15 Jun. 2017, the contents and elements of which are herein incorporated by reference for all purposes.

SEQUENCE LISTING

This application includes an electronically submitted Sequence Listing in .txt format. The .txt file contains a sequence listing entitled "SMKLP377732_ST25.txt" created on Aug. 18, 2020 and is 97.0 kb in size. The Sequence Listing contained in this .txt file is part of the specification and is hereby incorporated by reference herein in its entirety.

TECHNICAL FIELD

The present invention relates generally to methods and materials involving engineered genes encoding potassium channels which can be used in treating epilepsy and similar neurological disorders.

BACKGROUND ART

Epilepsy affects over 60 million people worldwide (Ngugi et al., 2010). Even with optimal treatment ~30% remain resistant to pharmacotherapy (Kwan et al., 2011; Picot et al., 2008). The development of new anti-epileptic drugs in the last 20 years has had little impact on refractory epilepsy; people with inadequately controlled seizures continue to experience major co-morbidities, social exclusion, and an annual rate of sudden unexpected death in epilepsy (SUDEP) of 0.5-1% (Devinsky, 2011; Hoppe and Elger, 2011). Although surgery can result in seizure freedom for patients with refractory epilepsy, it is unsuitable in over 90% of cases. Neocortical focal epilepsy is particularly poorly suited to surgical intervention because of the high risk of damage to eloquent regions of the cortex involved in language, vision or fine motor control (Schuele and Lüders, 2008). People with focal neocortical epilepsy are often left with very few, usually palliative, treatment options. There is therefore an urgent need to develop new treatments.

Gene therapy is one promising option (Kullmann et al., 2014), but major hurdles remain in achieving stable, predictable and safe transgene expression with viral vectors. Hitherto, clinical trials with lentivectors for CNS disorders have mainly been restricted to ex-vivo treatment of haematopoietic stem cells for enzyme defects (Biffi et al., 2013, 2013; Cartier et al., 2009); however a recent trial using a lentivector injected into the striatum has demonstrated safety and tolerability in Parkinson's disease, with some evidence of decreased L-DOPA requirement (Palfi et al., 2014).

Studies of gene therapy for epilepsy initially focused on acutely precipitated seizures, which often translate poorly (Galanopoulou et al., 2012). However, more recent strategies, mainly focusing on adeno-associated viruses (AAVs) in models of temporal lobe epilepsy, have shown that the development of seizures after an epileptogenic insult (epileptogenesis) can be attenuated (Bovolenta et al., 2010; Haberman et al., 2003; Kanter-Schlifke et al., 2007; Lin et al., 2006; McCown, 2006; Noe' et al., 2012; Richichi et al., 2004; Woldbye et al., 2010).

Potassium ion channels normally reduce the propensity of neurons to fire and to release neurotransmitters. When introduced to the brain using viral vectors they are effective as tools to dampen brain excitability and to treat experimental epilepsy in rodents. Potassium channel gene therapy is therefore promising for the treatment of human epilepsy as well as other neuropsychiatric diseases where neurons fire excessively such as chronic pain.

The association of potassium channels with neurological disorders, such as epilepsy, has been described (D'Adamo et al., 2013). Gene therapy strategies based on the up or downregulation of genes that modulate neuronal excitability have been described as a potential therapy (Wykes and Lignani, 2017).

Previous approaches to gene therapy in a model of epilepsia partialis continua (EPC) induced by tetanus toxin (TeNT) injection into the rat motor cortex (Katzel et al., 2014; Wykes et al., 2012) have been described. In this model pathological high-frequency electrocorticographic (ECoG) activity is prominent, but discrete long-lasting seizures are rare. Lentiviral overexpression of the human potassium channel Kv1.1, encoded by KCNA1, was highly effective at reducing pathological high frequency activity in the motor cortex (Wykes et al., 2011 & 2012). In vitro studies showed that Kv1.1 overexpression reduced both intrinsic neuronal excitability and glutamate release from transduced pyramidal neurons (Heeroma et al., 2009; Wykes et al., 2012). Importantly both effects were graded; that is, neither neuronal excitability nor neurotransmitter release was completely abolished. However, it remains unclear whether these graded effects on excitability and transmitter release, and the reduction of pathological ECoG activity in the motor cortex, can be extrapolated to commoner, longer-lasting focal seizures arising from other parts of the brain.

Streit et al. (2011 & 2014) describe that Kv1.1 channels undergo enzymatic RNA deamination to generate a channel with a single amino acid exchange located in the inner pore cavity (Kv1.1$^{I400V}$).

Therefore, there remains a need in the art for improved gene therapy tools for treating neurological diseases, such as epilepsy.

DISCLOSURE OF THE INVENTION

The present inventors have made a number of modifications to the KCNA1 gene that unexpectedly can be combined to enhance the translation and activity of the encoded Kv1.1 protein and improve the detection of KCNA1 gene expression in a cell. Briefly, the inventors have designed and tested an expression vector comprising an engineered KCNA1 gene that encodes an edited potassium channel. As demonstrated herein, the engineered KCNA1 gene of the present invention produces functional Kv1.1 channels and that when packaged in a lentiviral vector was able to significantly reduce seizure frequency when administered to rats in a randomised, blinded preclinical trial.

Aspects of the invention are defined in the claims appended hereto.

In one aspect the invention provides an expression vector comprising an engineered KCNA1 gene encoding an edited Kv1.1 potassium channel operably linked to a promoter suitable to drive expression of the edited Kv1.1 potassium channel in human cells, wherein the edited Kv1.1 potassium channel comprises a valine amino acid residue at a position corresponding to amino acid residue 400 shown in SEQ ID NO: 2. In one embodiment the engineered KCNA1 gene has a nucleotide sequence comprising or consisting of the nucleotide sequence shown in SEQ ID NO: 1.

In some embodiments, the expression vector is a viral vector, such as a lentiviral vector.

The invention also provides viral particles and in vitro methods of making viral particles as defined herein.

Further, the invention provides kits comprising viral vectors as defined herein and one or more viral packaging and envelope vectors as defined herein.

Further, the invention provides a viral particle as defined herein for use in a method of treatment of the human or animal body.

Further, the invention provides methods of confirming the presence of engineered KCNA1 RNA in a cell as defined herein and also an in vitro or ex vivo method of confirming the presence of engineered KCNA1 RNA in a cell that has been obtained from a subject administered with a viral particle as defined herein.

The invention also provides cells comprising the expression vector as defined herein.

Furthermore, the invention also provides a nucleic acid as defined herein.

Some particular aspects of the invention will now be discussed in more detail.

Expression Vectors

The invention provides an expression vector comprising an engineered KCNA1 gene encoding an edited Kv1.1 potassium channel operably linked to a promoter as defined herein.

An expression vector as used herein is a DNA molecule used to transfer and express foreign genetic material in a cell. Such vectors include a promoter sequence operably linked to the gene encoding the protein to be expressed. "Promoter" means a minimal DNA sequence sufficient to direct transcription of a DNA sequence to which it is operably linked. "Promoter" is also meant to encompass those promoter elements sufficient for promoter-dependent gene expression controllable for cell type specific expression; such elements may be located in the 5' or 3' regions of the native gene.

An expression vector may also include a termination codon and expression enhancers. Any suitable vectors, promoters, enhancers and termination codons may be used to express the edited Kv1.1 potassium channel from an expression vector according to the invention. Suitable vectors include plasmids, binary vectors, phages, phagemids, viral vectors and artificial chromosomes (e.g. yeast artificial chromosomes or bacterial artificial chromosomes). As described in more detail below, preferred expression vectors include viral vectors such as lentiviral vectors.

An expression vector may additionally include a reporter gene encoding a reporter protein. An example of a reporter protein is a green fluorescent protein (GFP). A reporter gene may be operably linked to its own promoter or, more preferably, may be operably linked to the same promoter as the engineered KCNA1 gene of the invention. As an example of the latter, the KCNA1 gene and reporter gene may be located either side of a sequence encoding a 2A peptide, such as a T2A peptide. 2A peptides are short (~20 amino acids) sequences that permit multicistronic gene expression from single promoters by impairing peptide bond formation during ribosome-mediated translation (Szymczak and Vignali, 2005). Having the reporter gene operably linked to the same promoter as the engineered KCNA1 gene is thought to act as a reliable indicator of KCNA1 gene expression. An expression vector including a reporter gene may be particularly useful in for preclinical applications, for example for use in animal models where it would be it can be used to help assess the localisation of gene expression.

In other embodiments, the expression vector lacks a sequence encoding a reporter protein. This may be preferred for regulatory reasons, for example. In embodiments of the invention, reporting or detecting the KCNA1 gene of the invention may be achieved in different ways—for example based on its engineered sequence.

Generally speaking, those skilled in the art are well able to construct vectors and design protocols for recombinant gene expression. Suitable vectors can be chosen or constructed, containing, in addition to the elements of the invention described above, appropriate regulatory sequences, including promoter sequences, terminator fragments, polyadenylation sequences, marker genes and other sequences as appropriate. Molecular biology techniques suitable for the expression of polypeptides in cells are well known in the art. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wiley & Sons, (1995, and periodic supplements).

The term "operably linked" used herein includes the situation where a selected gene and promoter are covalently linked in such a way as to place the expression of the gene (i.e. polypeptide coding) under the influence or control of the promoter. Thus, a promoter is operably linked to an engineered KNCA1 gene if the promoter is capable of effecting transcription of the gene into RNA in a cell. Where appropriate, the resulting RNA transcript may then be translated into a desired protein or polypeptide. The promoter is suitable to effect expression of the operably linked gene in a mammalian cell. Preferably, the mammalian cell is a human cell.

KCNA1 Genes and Kv1.1 Potassium Channels

KCNA1 (Gene ID 3736, also known as the Potassium Voltage-Gated Channel Subfamily A Member 1, KV1.1, HBK1 and RBK1) is a human gene that encodes the human Kv1.1 potassium channel (also known as Potassium voltage-gated channel subfamily A member 1). By "wild-type KCNA1 gene" it is meant the nucleic acid molecule that is found in human cells and encodes the human Kv1.1 potassium channel. The KCNA1 gene may include regulatory sequences upstream or downstream of the coding sequence. A nucleotide sequence for the wild-type KCNA1 gene, including the non-coding 5' and 3' untranslated regions (5' and 3' UTRs) is provided in NCBI Reference Sequence NM_000217.2. The coding sequence for the wild-type KCNA1 gene has the nucleotide sequence of SEQ ID NO: 4, which corresponds to positions 1106 to 2593 of NCBI Reference Sequence NM_000217.2.

The Kv1.1 potassium channel is a voltage-gated delayed potassium channel that is phylogenetically related to the *Drosophila* Shaker channel. The amino acid sequence for the wild-type Kv1.1 potassium channel has the amino acid sequence of SEQ ID NO: 5 which is identical to the NCBI Reference Sequence NP_000208.2. Voltage-dependent potassium channels modulate excitability by opening and closing a potassium-selective pore in response to voltage. In many cases, potassium ion flow can be interrupted when an intracellular particle occludes the pore, a process known as fast inactivation. The Kv1.1 potassium channel has six putative transmembrane segments, and the loop between the fifth and sixth segment forms the pore.

During normal production in cells, some of the KCNA1 RNA in the cell is edited by an adenosine deaminase acting on RNA (ADAR) that causes an isoleucine/valine (I/V) recoding event at a single position 1400 that lies within the sixth transmembrane domain and lines the inner vestibule of the ion-conducting pore (Hoopengardner et al., *Science* 301(5634):832-6, 2003). At negative membrane potentials, channels containing unedited 1400 recover from inactivation at a rate around twenty times slower than their edited (V400) counterparts (Bhalla et al., 2004).

The present invention involves the expression of an edited Kv1.1 potassium channel.

An "edited Kv1.1 potassium channel" is a functional Kv1.1 potassium channel but contains the isoleucine/valine mutation described above. Without wishing to be bound by any particular theory, it is believed that providing an edited Kv1.1 potassium channel is advantageous as it immediately provides the cell with edited Kv1.1 potassium channels, without relying on the ADAR-dependent RNA edited step that normally occurs in the cell. It is believed that these edited Kv1.1 potassium channels are much quicker at recovering from inactivation than their unedited counterparts.

Furthermore, not all of the KCNA1 RNA is normally edited in the cell. As described by Hoopengardner et al., *Science* 301(5634):832-6, 2003 (see, in particular, FIG. 3) the amount of RNA editing that occurs varies across different regions of the human nervous system, ranging from around 17% in the caudate nucleus to around 77% in the medulla. For example, around 20% of KCNA1 RNA is believed to be edited in the frontal cortex meaning that around 80% of KCNA1 RNA remains unedited in this region of the brain. As shown in the examples herein, providing an engineered KCNA1 gene that encodes an edited Kv1.1 channel was able to efficiently reduce seizure frequency when administered to rats in a randomised, blinded, preclinical trial.

As used herein, an edited Kv1.1 potassium channel has an amino acid sequence having at least 70, 75, 80, 85, 90, 91, 92, 93, 94, 95, 96, 97, 98, 99 or 100% sequence identity to the amino acid sequence shown in SEQ ID NO: 2 provided it also contains a valine amino acid residue at a position corresponding to amino acid residue 400 shown in SEQ ID NO: 2 (the 'edited position'). In some preferred embodiments, the edited Kv1.1 potassium channel has an amino acid sequence comprising or consisting of the amino acid sequence shown in SEQ ID NO: 2.

An edited Kv1.1 potassium channel that contains a valine amino acid residue at a position corresponding to amino acid residue 400 shown in SEQ ID NO: 2 can be identified by methods known in the art. For example, the edited position can be identified by a sequence alignment between the amino acid sequence of SEQ ID NO: 2 and the amino acid sequence of the edited Kv1.1 potassium channel of interest. Such sequence alignments can then be used to identify the edited position in the edited Kv1.1 potassium channel of interest which, at least in the alignment, is near, or at the same position as, the edited position at amino acid residue 400 in the amino acid sequence shown in SEQ ID NO: 2.

A functional Kv1.1 potassium channel is a protein that retains the normal activity of a potassium channel, e.g. the channels are able to open and close in response to voltage. Methods of testing that the Kv1.1 potassium channels are functional are known in the art and some of which are described herein. Briefly, a suitable method for confirming that the Kv1.1 potassium channel is functional involves transfecting cells with an expression vector encoding a Kv1.1 potassium channel and using electrophysiological techniques such as patch clamping to record currents of the potassium channels.

The wild-type Kv1.1 potassium channel comprises a tyrosine amino acid at position 379 as shown in SEQ ID NO: 5. In some embodiments, an edited Kv1.1 potassium channel comprises a tyrosine amino acid residue at a position corresponding to amino acid residue 379 shown in SEQ ID NO: 2.

In other embodiments, an edited Kv1.1 potassium channel comprises a valine amino acid residue at a position corresponding to amino acid residue 379 shown in SEQ ID NO: 2. An example of an edited Kv1.1 potassium channel with this amino acid sequence is shown in SEQ ID NO: 14. Without wishing to be bound by any particular theory, it is believed that a Y379V mutation reduces the sensitivity of Kv1.1 channels to tetraethylammonium (TEA) without altering the functional properties of the potassium channel. For example, this change in sensitivity allows transgenic Kv1.1 channels to be pharmacologically isolated from their wild-type counterparts in patch clamp electrophysiology experiments (Heeroma et al. 2009).

In the present invention an "engineered KCNA1 gene" is used. An engineered KCNA1 gene differs from the nucleotide sequence of the wild-type KCNA1 gene as described herein but still encodes for a functional Kv1.1 potassium channel. As used herein, an engineered KCNA1 gene has a nucleotide sequence having at least 70, 75, 80, 85, 90, 91, 92, 93, 94, 95, 96, 97, 98, 99 or 100% sequence identity to the nucleotide sequence shown in SEQ ID NO: 1. In some preferred embodiments, the engineered KCNA1 gene has a nucleotide sequence comprising or consisting of the nucleotide sequence shown in SEQ ID NO: 1.

As described above, an embodiment of the invention includes an engineered KCNA1 gene encoding an edited potassium channel that comprises a valine amino acid residue at position 379, as shown in SEQ ID NO: 14. An example of an engineered KCNA1 gene that encodes the amino acid sequence shown in SEQ ID NO: 14 is the nucleotide sequence shown in SEQ ID NO: 13. In some embodiments, the engineered KCNA1 gene has a nucleotide sequence comprising or consisting of the nucleotide sequence shown in SEQ ID NO: 13, or has at least 75, 80, 85, 90, 91, 92, 93, 94, 95, 96, 97, 98, 99 or 100% sequence identity to the nucleotide sequence shown in SEQ ID NO: 13.

Cell Type Specific Promoters

Previous studies relied on driving overexpression of KCNA1 with a strong viral promoter (CMV), which in rat demonstrated a strong bias for excitatory neurons (Wykes et al., 2013). However, there are safety concerns associated with the use of non-specific promoters such as the CMV promoter. For example, in the case of epilepsy, a concern is the possibility of potassium channel overexpression in cells other than excitatory neurons, for example interneurons, which could aggravate seizure activity by exacerbating rather than attenuating local excitability. A method of improving safety would therefore be to restrict expression of the Kv1.1 potassium channel to particular cell types. However it is not clear if promoters that drive cell type specificity would provide sufficient expression to have a functional effect in vivo, particularly in the case where an edited Kv1.1 potassium channel is expressed.

The present inventors found that the improved expression as a result of the engineered KCNA1 gene meant that a cell type specific promoter could be used to drive expression of this gene.

Thus, in some embodiments, the promoter is a cell type specific promoter that drives cell type specific expression of the edited Kv1.1 potassium channel. A cell type specific promoter is a promoter that drives more expression in the cell type of interest than in other cell types. For example, where the cell type specific promoter is specific for neurons, this will drive more expression in neurons than in other cell types, for example glial cells. Preferably, the cell type specific promoter means at least 60%, 70%, 80%, 90%, 95%, 96%, 97%, 98% 99% or most preferably 100% of expression occurs in the cell type of interest than in another cell type.

Methods of determining gene and protein expression and localisation are known in the art. They include assays that detect RNA transcripts, such as hybridisation methods described herein, as well as and methods that detect protein such as immunohistochemical methods. One such method for assessing the cell type specificity of the cell type specific promoter would be to compare the overlap of RNA transcripts or protein with markers for particular cell types. For example, where the cell type specific promoter is believed to be specific for neurons, localisation of the RNA or protein for the gene of interest operably linked to this promoter can be compared for overlap with localisation of known immunohistochemical markers for neurons, e.g. NeuN, and glial cells, e.g. GFAP. The promoter will be considered a neuron cell type specific promoter if greater overlap is observed between the gene of interest and neurons than between the gene of interest and glial cells.

The cell type specific promoter that is used will depend on the cell type that is being targeted. For example, in the case of a treating a neurological disorder, it may be preferable to target neural cells, such as neurons and glial cells. In particularly preferred examples, the cell type specific promoters is specific for neurons, in other words it drives higher levels of expression in neurons than in glial cells. In some cases, the cell type specific promoter is specific for excitatory neurons, such as glutamatergic neurons. An example of an excitatory neuron is a pyramidal neuron. Glutamatergic neurons can be identified by detecting markers that are specific for gluatamatergic cells, such as vGlut1, vGlut2, NMDAR1, NMDAR2B, glutaminase, glutamine synthetase. Without wishing to be bound by any particular theory, cell type specific expression of the engineered KCNA1 gene in glutamatergic neurons is believed to be useful for treatment of diseases associated with neuronal hyperexcitability, in particular epilepsy.

A preferred example of the neuronal cell type specific promoter is the human CAMK2A (alpha CaM kinase II gene) promoter. The CAMK2A promoter is known to bias expression to excitatory neurons and furthermore leads to very little expression in GABAergic cells (also known as interneurons) (Dittgen et al., 2004; Yaguchi et al., 2013). The CAMK2A promoter is therefore an example of a cell type specific promoter that is specific for excitatory neurons. The CAMK2A promoter may have a nucleotide sequence comprising or consisting of the nucleotide sequence of SEQ ID NO: 3. Alternatively, the CAMK2A promoter may have a nucleotide sequence comprising or consisting of a nucleotide sequence having at least 70, 75, 80, 85, 90, 91, 92, 93, 94, 95, 96, 97, 98 or 99% identity to the nucleotide sequence of SEQ ID NO: 3.

Another promoter that is believed to be specific for neurons is the VGLUTI promoter (Zhang et al. Brain Research 1377:1-12, 2011, herein incorporated by reference at least for the sequence of the promoters and related sequences). As described by Zhang et al., the rat VGLUT1 upstream promoter or the first intron, after fusion to a basal promoter, results in glutamatergic-specific expression. A further example of a promoter that has been shown to be specific for glutamatergic neurons in rats is the PAG promoter (Rasmussen et al. Brain Research 1144: 19-32, 2007, herein incorporated by reference at least for the sequence of the promoters and related sequences).

Other neuronal cell type-specific promoters include the NSE promoter (Liu H. et al., Journal of Neuroscience. 23(18):7143-54, 2003 & Peel A L. et al., Gene Therapy. 4(1): 16-24, 1997); tyrosine hydroxylase promoter (Kessler M A. et al., Brain Research. Molecular Brain Research. 112(I-2):8-23, 2003); myelin basic protein promoter (Kessler M A. et al Biochemical & Biophysical Research Communications. 288(4):809-18, 2001); neurofilaments gene (heavy, medium, light) promoters (Yaworsky P J. et al., Journal of Biological Chemistry. 272(40):25112-20, 1997) (All of which are herein incorporated by reference at least for the sequence of the promoters and related sequences.). A further suitable promoter is the Synapsin1 promoter (see Kugler et al "Human synapsin 1 gene promoter confers highly neuron-specific long-term transgene expression from an adenoviral vector in the adult rat brain depending on the transduced area." Gene Therapy. 10(4):337-47 2003).

The Nav1.7 and Nav1.8 sodium channels are thought to play an important role in pain and therefore their promoter could be used for the treatment of diseases such as chronic pain. The human gene that encodes Nav1.7 is SCN9A and the identification and use of the SCN9A promoter has been described, for example, in Diss et al. Molecular and Cellular Neuroscience. 37(3): 537-47, 2008. The human gene that encodes Nav1.8 is SCN10A and the identification and use of the SCN10A has been described, for example, in Puhl & Ikeda, Journal of Neurochemistry. 106(3): 1209-24, 2008. These references are herein incorporated by reference at least for the sequence of the promoters and related sequences.

Viral Vectors

A preferred expression vector for use with the present invention is a viral vector, such as a lentiviral or AAV vector. A particularly preferred expression vector is a lentiviral vector. Lentiviral vectors are a special type of retroviral vector which, when assembled into viral particles, are typically characterized by having a long incubation period for infection and are able to infect non-dividing cells, such as post-mitotic neurons. Lentiviral vectors generally lead to rapid, stable and spatially-restricted expression (Lundberg et al., 2008). This may be optimal for treatment of disease such as epilepsy where focal seizures often arise from brain areas very close to eloquent cortex. In addition, the large packaging capacity of lentivectors allows a greater choice of promoter-transgene combinations (Kantor et al., 2014), which can further increase the specificity of expression.

Lentiviral vectors are based on the nucleic acid backbone of a virus from the lentiviral family of viruses. The infectious process of a lentivirus found in nature is well known to the skilled person. Without wishing to be bound by any particular theory, a brief description of this is provided here. A lentivirus is a retrovirus, meaning it has a single stranded RNA genome and a reverse transcriptase enzyme. This single stranded RNA genome is packaged within a viral envelope with protruding glycoproteins that aid in attachment to a host cell's outer membrane. Within the viral genome are nucleic acid sequences, including the gag, pol and env gene regions. The pol gene encodes the reverse transcriptase enzyme, required for reverse transcription of the viral RNA genome and the integrase enzyme, required for efficient integration of the viral genome into the host cell genome. The env gene encodes various envelope proteins and the gag gene encodes various structural proteins.

During infection, the viral material is injected into the host cell where the viral reverse transcriptase performs reverse transcription of the viral RNA genome to create a viral DNA genome. The viral DNA is then incorporated into the host cell's genome. From there the host cell performs transcription and translation to create viral particles which burst from the host cell and can go on to infect other host cells.

Lentiviral vectors have been developed by removing the non-essential sequences and genomic regions involved with viral replication and virulence from the wild-type lentiviral genome, resulting in a replication defective vector containing the necessary elements for packaging and processing (Shaw & Cornetta, *Biomedicines* 2(1): 14-35, 2014).

As used herein a lentiviral vector means a DNA expression vector which comprises the lentiviral genes sufficient to result in the engineered KCNA1 gene being transcribed into RNA and which RNA is packaged into a viral particle when expressed alongside lentiviral envelope and packaging proteins. Typically, the lentiviral vector contains 5' and 3' long terminal repeat (LTR) regions of a lentivirus, such as SIV and HIV. The 5' LTR can act as an RNA polymerase promoter. In some lentiviral vectors, part of the 5' LTR promoter, such as the U3 region, is replaced by another promoter, generally a constitutive promoter such as a CMV or RSV promoter. The lentiviral vector may also contain a bacterial plasmid portion, additional lentiviral elements required for viral vector RNA packaging and intracellular transport, a marker gene and elements for their regulation, optional chromatin-control elements and sites for convenient plasmid DNA re-engineering.

In preferred embodiments, the lentiviral vector comprises, in order from 5' to 3', a CMV enhancer/promoter, a truncated 5' LTR, a HIV-1 packaging signal, a Rev response element, a central polypurine tract and central termination sequence (cPPT/CTS), a cell type specific promoter (such as a human CAMK2A promoter), an engineered KCNA1 gene, a woodchuck hepatitis virus post-translational regulatory element and a 3' LTR. In some embodiments, the lentiviral vector contains a sequence encoding a reporter protein, such as a fluorescent protein. An example of a lentiviral vector containing a sequence encoding GFP is shown in SEQ ID NO: 7. In other embodiments the lentiviral vector lacks a sequence encoding a reporter protein, such as a fluorescent protein.

In some embodiments, the lentiviral vector comprises a nucleotide sequence having at least 70, 75, 80, 85, 90, 91, 92, 93, 94, 95, 96, 97, 98 or 99% identity to the nucleotide sequence of SEQ ID NO: 9 or SEQ ID NO: 11. In some embodiments, the lentiviral vector comprises the nucleotide sequence of SEQ ID NO: 9 or SEQ ID NO: 11. SEQ ID NO: 9 encodes an edited Kv1.1 potassium channel with a tyrosine at position 379 whilst SEQ ID NO: 11 encodes an edited Kv1.1 potassium channel with a valine at position 379.

In some embodiments, the lentiviral vector comprises a nucleotide sequence having at least 70, 75, 80, 85, 90, 91, 92, 93, 94, 95, 96, 97, 98 or 99% identity to the nucleotide sequence of SEQ ID NO: 10 or SEQ ID NO: 12. In some embodiments, the lentiviral vector comprises or consists of the nucleotide sequence of SEQ ID NO: 10 or SEQ ID NO: 12. SEQ ID NO: 10 encodes an edited Kv1.1 potassium channel with a tyrosine at position 379 whilst SEQ ID NO: 12 encodes an edited Kv1.1 potassium channel with a valine at position 379.

In some embodiments, the lentiviral vector additionally comprises genes encoding viral packaging and envelope proteins.

In some embodiments, the lentiviral vector is a non-integrating lentiviral vector (NILV). Vector particles produced from these vectors do not integrate their viral genome into the genome of the cells and therefore are useful in applications where transient expression is required or for sustained episomal expression such as in quiescent cells. NILVs can be developed by mutations in the integrase enzyme or by altering the 5' LTR and/or the 3' LTR to prevent integrase from attaching these sequences. These modifications eliminate integrase activity without affecting reverse transcription and transport of the pre-integration complex to the nucleus. Without wishing to be bound by any particular theory, when a NILV enters a cell the lentiviral DNA is expected to remain as remains in the nucleus as an episome, leading to sustained expression in cell, e.g. post-mitotic cells. As demonstrated herein, the combined use of a NILV and a cell type specific promoter such as CAMK2A means that expression can be effectively targeted to particular cell types such as neurons.

Methods of generating NILVs are described by Shaw & Cornetta *Biomedicines* 2(1): 14-35, 2014, which is herein incorporated by reference. Examples of a mutation that is used to inhibit integration is the D64 mutation in an integrase enzyme, for example a D64V substitution. This and other examples of suitable modifications that inhibit integration are described in, e.g. Table 1 of Shaw & Cornetta, *Biomedicines* 2(1): 14-35, 2014.

Viral Particles

The invention also includes in vitro methods of making lentiviral particles. In one embodiment, this method involves transducing mammalian cells with a lentiviral vector as described herein and expressing viral packaging and envelope proteins necessary for particle formation in the cells and culturing the transduced cells in a culture medium, such that the cells produce lentiviral particles that are released into the medium. An example of a suitable mammalian cell is a human embryonic kidney (HEK) 293 cell.

It is possible to use a single expression vector that encodes all the lentiviral components required for viral particle formation and function. Most often, however, multiple plasmid expression vectors or individual expression cassettes integrated stably into a host cell are utilised to separate the various genetic components that generate the lentiviral vector particles.

In some embodiments, expression cassettes encoding the one or more viral packaging and envelope proteins have been integrated stably into a mammalian cell. In these embodiments, transducing these cells with a lentiviral vector described herein is sufficient to result in the production of lentiviral particles without the addition of further expression vectors.

In other embodiments, the in vitro methods involve using multiple expression vectors. In some embodiments, the method comprises transducing the mammalian cells with one or more expression vectors encoding the viral packaging and envelope proteins that encode the viral packaging and envelope proteins necessary for particle formation.

Examples of suitable viral packaging and envelope proteins and expression vectors encoding these proteins are commercially available and well known in the art. In general, the viral packaging expression vector or expression cassette expresses the gag, pol, rev, and tat gene regions of HIV-1 which encode proteins required for vector particle formation and vector processing. In general, the viral envelope expression vector or expression cassette expresses an envelope protein such as VSV-G. In some cases, the packaging proteins are provided on two separate vectors—one encoding Rev and one encoding Gag and Pol. Examples of lentiviral vectors along with their associated packaging and envelope vectors include those of Dull, T. et al., "A Third-generation lentivirus vector with a conditional packaging system" *J. Virol* 72(11):8463-71 (1998), which is herein incorporated by reference.

An example of a viral envelope expression vector is pMDG-VSV-G, which contains the vsv-g gene operably linked to a CMV promoter. The construction of this vector is described by Kafri et al. 1999 *J Virol.* 73(1): 576-584, which is herein incorporated by reference.

An example of a viral packaging expression vector is pCMVdR8.74, which contains the gag, pol, tat and rev genes operably linked to a CMV promoter. This viral packaging expression vector is available, for example, from Addgene (Cambridge, Mass., USA) as plasmid number 22036.

As explained above, in some embodiments the viral packaging expression vector is an integrase-deficient viral packaging expression vector. For example, the integrase-deficient viral packaging expression vector may encode a non-functional (e.g. mutated) integrase enzyme, such as a mutant D64V integrase. Vector particles produced from these vectors having non-functional integrases do not efficiently integrate their viral genome into the genome of the cells. An example of an integrase-deficient viral packaging expression vector is pCMVdR8.74$^{D64V}$, which contains the gag, pol, tat and rev genes operably linked to a CMV promoter and where the pol gene encodes a mutant D64V integrase. pCMVdR8.74$^{D64V}$ is a 2$^{nd}$ generation human immunodeficiency virus 1 (HIV-1) packaging plasmid with an aspartic acid$^{64}$-valine mutation in its integrase coding sequence. This mutation reduces genomic integration by a factor of 10,000 compared to wild-type levels (Leavitt et al. 1996). The construction and use of this vector is described in Leavitt et al. 1996 and Yáñez-Muñoz et al. *Nature Medicine.* 12(3): 348-53, 2006, which are herein incorporated by reference.

Following release of viral particles, the culture medium comprising the viral particles may be collected and, optionally the viral particles may be separated from the culture medium. Optionally, the viral particles may be concentrated.

Following production and optional concentration, the viral particles may be stored, for example by freezing at −80° C. ready for use by administering to a cell and/or use in therapy.

The invention also provides viral particles, for example those produced by the methods described herein. As used herein, a viral particle comprises a RNA genome packaged within the viral envelope that is capable of infecting a cell, e.g. a mammalian cell. A viral particle may be integrase deficient, e.g. it may contain a mutant integrase enzyme or contain alterations in the 5' and/or 3' LTRs as described herein.

Kits

The invention also provides kits that comprise a lentiviral vector as described herein and one or more packaging and envelope expression vectors also described herein. In some embodiments the viral packaging expression vector is an integrase-deficient viral packaging expression vector, such as the pCMVdR8.74$^{D64V}$ vector described herein.

Disorders

The viral vectors and viral particles described herein may also be for use as a medicament. For example, a viral particle as described herein may be used in gene therapy.

The invention provides the use of a viral particle as described herein for the manufacture of a medicament for the treatment of a human or animal body, a viral particle as described herein for use in the treatment of a human or animal body and a method of treatment which comprises administering the viral particle as described herein to an individual in need thereof.

In certain embodiments, the viral particle is used in the treatment of a neurological disorder. Non-limiting examples of neurological disorders include seizure disorders (such as epilepsy), Alzheimer's disease, multiple sclerosis, Parkinson's disease, tremor and other movement disorders, chronic pain, migraine, and other neuropsychiatric diseases associated with alterations in neuronal excitability, including major depression, bipolar disorder, anxiety, and schizophrenia.

In certain embodiments, the neurological disorder is associated with neuronal hyperexcitibility. Non-limiting examples of neurological disorders associated with neuronal hyperexcitability include seizure disorders (such as epilepsy), Alzheimer's disease, multiple sclerosis, Parkinson's disease, tremor and other movement disorders, chronic pain, migraine, major depression, bipolar disorder, anxiety, and schizophrenia.

In preferred embodiments the treatment is for epilepsy, chronic pain, depression or Parkinson's disease.

In particularly preferred embodiments, the treatment is for epilepsy, for example idiopathic, symptomatic and cryptogenic epilepsy. The epilepsy may be neocortical epilepsy. The treatments described herein may be used to quench or blocking epileptogenic activity. The treatments may be used to reduce the frequency of seizures. The treatments may be used to temporally or permanently reduce neuronal excitability in the neurons.

Administration and Dosage

The viral particles described herein can be delivered to the subject in a variety of ways, such as direct injection of the viral particles into the brain. For example, the treatment may involve direct injection of the viral particles into the cerebral cortex, in particular the neocortex. The treatment may involve direct injection of the viral particles into the location in the brain where it is believed to be functionally associated with the disorder. For example, where the treatment is for epilepsy this may involve direct injection of the viral particles into the motor cortex; where the treatment is for chronic pain, this may involve direct injection of the viral particles into the dorsal root ganglion; and where the treatment is for Parkinson's disease, this may involve direct injection of the viral particles into the Substantia Nigra. The particular method and site of administration would be at the discretion of the physician who would also select administration techniques using his/her common general knowledge and those techniques known to a skilled practitioner.

The invention may also be used to treat multiple epileptic foci simultaneously by injection directly into the multiple identified loci.

The patient may be one who has been diagnosed as having drug-resistant or medically-refractory epilepsy, by which is meant that epileptic seizures continue despite adequate administration of antiepileptic drugs.

The subject may be one who has been diagnosed as having well defined focal epilepsy affecting a single area of the neocortex of the brain. Focal epilepsy can arise, for example, from developmental abnormalities or following strokes, tumours, penetrating brain injuries or infections.

Following administration of the viral particles, the recipient individual may exhibit reduction in symptoms of the disease or disorder being treated. For example, for an individual being treated who has a seizure disorder such as epilepsy, the recipient individual may exhibit a reduction in the number of seizures. This may have a beneficial effect on the disease condition in the individual.

The term "treatment," as used herein in the context of treating a condition, pertains generally to treatment and therapy of a human, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The viral particle can be delivered in a therapeutically-effective amount.

The term "therapeutically-effective amount" as used herein, pertains to that amount of the viral particle which is effective for producing some desired therapeutic effect, commensurate with a reasonable benefit/risk ratio, when administered in accordance with a desired treatment regimen.

Similarly, the term "prophylactically effective amount," as used herein pertains to that amount of the viral particle which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

While it is possible for the viral particle to be used (e.g., administered) alone, it is often preferable to present it as a composition or formulation e.g. with a pharmaceutically acceptable carrier or diluent.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some embodiments, the composition is a pharmaceutical composition (e.g., formulation, preparation, medicament) comprising, or consisting essentially of, or consisting of as a sole active ingredient, viral particle as described herein, and a pharmaceutically acceptable carrier, diluent, or excipient.

As described in WO2008096268, in gene therapy embodiments employing delivery of the viral particle, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100 fold) due to the presence of infection-defective particles.

In some embodiments the methods or treatments of the present invention may be combined with other therapies, whether symptomatic or disease modifying.

The term "treatment" includes combination treatments and therapies, in which two or more treatments or therapies are combined, for example, sequentially or simultaneously.

For example it may be beneficial to combine treatment with a compound as described herein with one or more other (e.g., 1, 2, 3, 4) agents or therapies.

Appropriate examples of co-therapeutics will be known to those skilled in the art on the basis of the disclosure herein. Typically the co-therapeutic may be any known in the art which it is believed may give therapeutic effect in treating the diseases described herein, subject to the diagnosis of the individual being treated. For example epilepsy can sometimes be ameliorated by directly treating the underlying etiology, but anticonvulsant drugs, such as phenytoin, gabapentin, lamotrigine, levetiracetam, carbamazepine and clobazam, and topiramate, and others, which suppress the abnormal electrical discharges and seizures, are the mainstay of conventional treatment (Rho & Sankar, 1999, Epilepsia 40: 1471-1483).

The particular combination would be at the discretion of the physician who would also select dosages using his/her common general knowledge and dosing regimens known to a skilled practitioner.

The agents (i.e. viral particle, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

Methods of Confirming Presence of KCNA1

The invention also provides a method of confirming the presence of engineered KCNA1 in a cell.

Overexpressing a normal human brain potassium channel avoids the risk of immune reactions, which potentially limit the clinical translation of gene therapy using other membrane proteins. However, a limitation of clinical translation using the normal gene sequence of human potassium channels is that it is difficult to detect their expression against the background endogenous channels present in the brain.

Because the sequence of the engineered KCNA1 gene differs from the wild-type KCNA1 gene found in cells, when this gene is transcribed into RNA it incorporates a unique RNA sequence (an 'RNA-fingerprint'). This RNA-fingerprint permits specific tracking of transgene expression with RNA-targeted techniques that would otherwise fail to distinguish between transgenic and endogenous KCNA1. This is particularly useful where it is important to determine the localisation of engineered KCNA1 gene expression without having to include sequences encoding fluorescent tags or epitopes that could potentially result in immunogenicity.

For example, tissue removed from patients who have been treated with the engineered KCNA1 gene could be examined to determine where and in which cell types (excitatory neurons as expected, or inhibitory neurons or glial cells) the KCNA1 RNA was present. Such tissue could be obtained, for instance, from epilepsy surgery in the event of epilepsy gene therapy failure, or post-mortem. This data is expected to be useful for preclinical dosage calculation, biodistribution studies, regulatory approval and further clinical development on potassium channel gene therapy.

Thus, in one embodiment the method comprises transducing a cell with an expression vector as described herein or administering a viral particle as described herein to a cell under conditions that permit expression of engineered KCNA1 RNA and detecting the presence of engineered KCNA1 RNA in the cell using a hybridisation assay. This method can be carried out in vitro or ex vivo, for example in cell culture or in cells explanted from a human or animal body. Alternatively, the method can be carried out in vivo, for example where the viral particles are administered to a cell in a human or animal subject before extracting the cells or tissues from the human or animal subject in order to detect the presence of engineered KCNA1 RNA in the cell using a hybridisation assay.

In some embodiments, cells or tissues are extracted from a subject who has been treated with viral particles of the invention in order to examine localisation of the expressed KCNA1 gene. Such tissue could be obtained, for instance, from epilepsy surgery in the event of epilepsy gene therapy failure, or post-mortem.

The invention also provides an in vitro or ex vivo method of confirming the presence of engineered KCNA1 in a cell that has been obtained from a subject administered with a viral particle described herein, the method comprising detecting the presence of engineered KCNA1 RNA in the cell using a hybridisation assay.

Hybridisation assays are known in the art and generally involve using complementary nucleic acid probes (such as in situ hybridization using labelled probe, Northern blot and related techniques). In some embodiments, the hybridisation assay is an in situ hybridisation assay using a labelled probe, such as a fluorescently labelled probe.

As used herein, the term "probe" refers to a nucleic acid used to detect a complementary nucleic acid. Typically the probe is an RNA probe.

Suitable selective hybridisation conditions for oligonucleotides of 17 to 30 bases include hybridization overnight at 42° C. in 6×SSC and washing in 6×SSC at a series of increasing temperatures from 42 oC to 65 oC. One common formula for calculating the stringency conditions required to achieve hybridization between nucleic acid molecules of a specified sequence homology is (Sambrook et al., 1989): Tm=81.5 oC+16.6 Log [Na+]+0.41 (% G+C)−0.63 (% formamide)−600/ #bp in duplex.

Cells

The invention also provides a cell comprising the nucleic acid or vector described above. In some embodiments, this cell is a mammalian cell such as a human cell. In some embodiments, the cell is a human embryonic kidney cell (HEK) 293.

Nucleic Acids and Sequence Variants

The invention also provides a nucleic acid comprising an engineered KCNA1 gene encoding an edited Kv1.1 potassium channel, as defined herein. The engineered KCNA1 gene present in the nucleic acid and edited Kv1.1 potassium channel can have the requisite features and sequence identity as described herein in relation to the expression vectors.

Alignment and calculation of percentage amino acid or nucleotide sequence identity can be achieved in various ways know to a person of skill in the art, for example, using publically available computer software such as ClustalW 1.82, T-coffee or Megalign (DNASTAR) software. When using such software, When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA END-GAP=−1, Protein/DNA GAPDIST=4.

The percentage identity can then be calculated from the multiple alignment as (N/T)*100, where N is the number of positions at which the two sequences share an identical residue, and T is the total number of positions compared. Alternatively, percentage identity can be calculated as (N/S) *100 where S is the length of the shorter sequence being compared. The amino acid/polypeptide/nucleic acid sequences may be synthesised de novo, or may be native amino acid/polypeptide/nucleic acid sequence, or a derivative thereof.

Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. As described herein, suitable variants of the edited Kv1.1 potassium channel can contain amino acid substitutions at any amino acid other than the amino acid residue at a position corresponding to amino acid residue 400 shown in SEQ ID NO: 2.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1: Characterisation of the visual cortex TeNT model of focal neocortical epilepsy.

A. Representative seizure from an adult male Sprague Dawley rat showing its long duration and evolution over time (see FIG. 2 for representative seizures from Lister Hooded and Long-Evans rats). Expanded sections are taken at the times indicated.

B. Number of seizures per week for 9 animals recorded over a period of 5 weeks showing an increase to plateau at week 3, followed by a decline in frequency during week 5.

C. Cumulative seizure frequency (per day) over the same period.

D. Seizure duration (per week) over the same period indicating an initial rise to a stable duration of around 100 s.

E. Behavioural correlates of 102 randomly selected electrographic seizures (N=8 animals, n=102 seizures). All behaviour was assessed by a neurologist using video recordings time-locked to the ECoG trace. In the 11 cases where the behavioural correlate is 'unknown', either the animals were not visible beneath bedding or the video signal was interrupted.

Data are presented as mean±the standard error of the mean (SEM).

Figure 2:
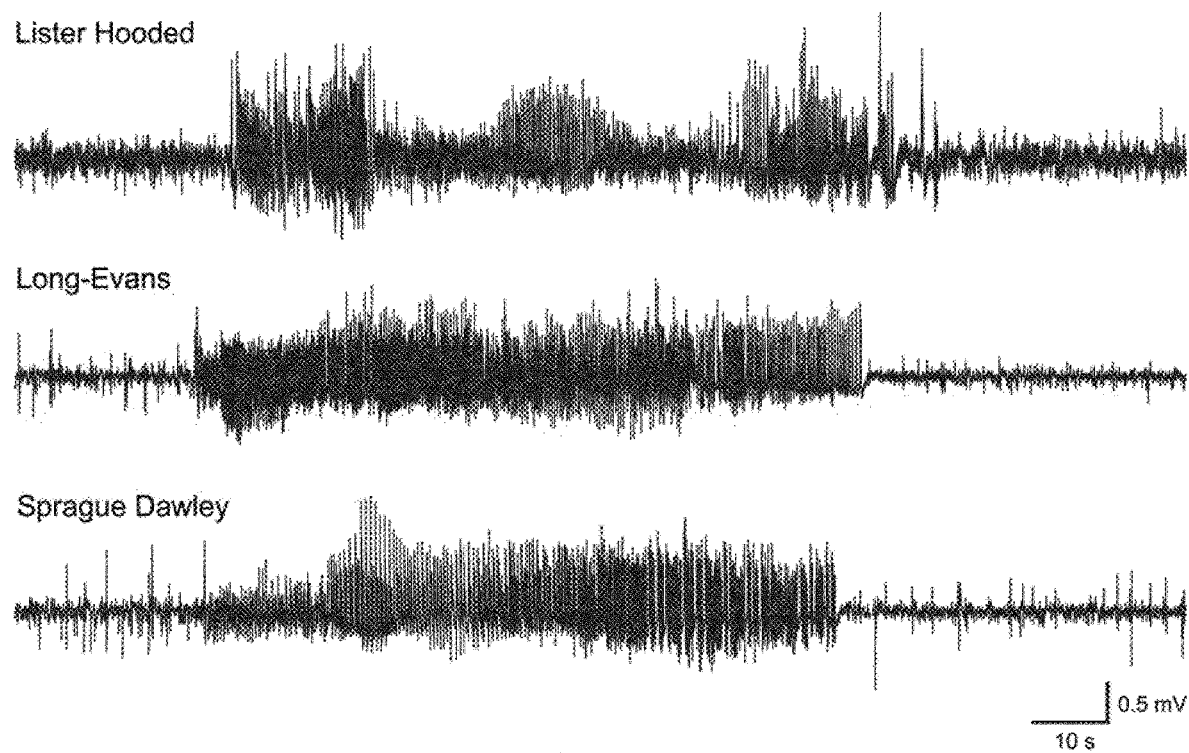

FIG. 2: The TeNT visual cortex model of focal neocortical epilepsy is not strain-specific.

Representative seizures from Lister Hooded, Long-Evans and Sprague Dawley rats.

Figure 3:
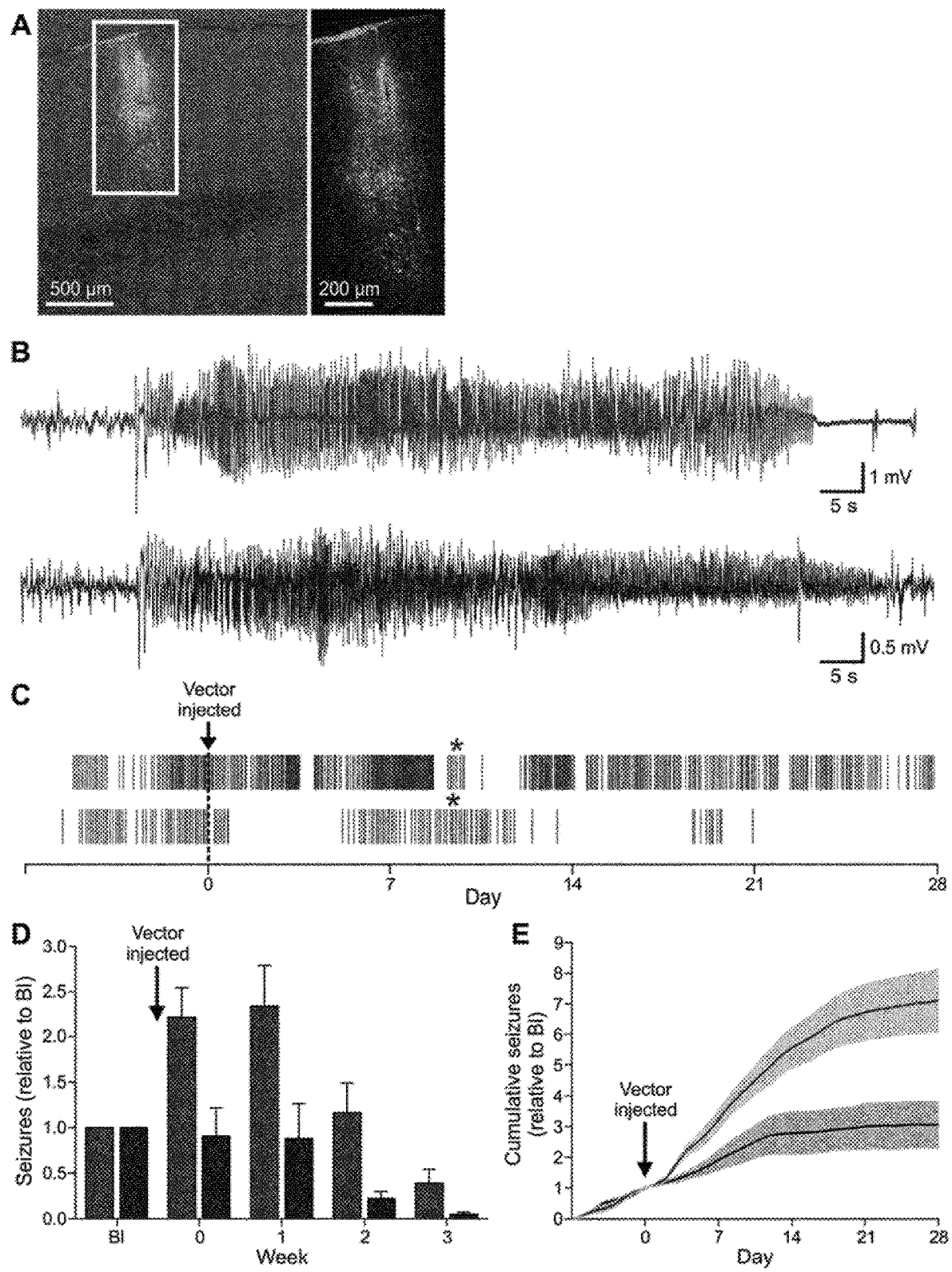

FIG. 3: Kv1.1 overexpression reduces seizure frequency in the visual cortex model of focal neocortical epilepsy.

A. Neuronal transduction by the CMV-KCNA1 lentivector is restricted to a narrow column of cortex surrounding the site of injection.

B. Representative seizures from two animals after treatment with the CMV-KCNA1 lentivector (bottom trace) or its GFP-only control (top trace).

C. Raster plots of all seizures experienced by the same animals over the full 5 weeks of recording. Seizures presented in panel B are marked by asterisks.

D. Seizure frequency (per week) for rats treated with the CMV-KCNA1 lentivector (n=8) or its GFP-only control (n=8). The numbers of seizures experienced each week were normalized to the number experienced by each animal in the week preceding treatment (week BI). The CMV-KCNA1 lentivector significantly reduced normalized seizure frequency in the weeks following treatment.

E. Cumulative seizure frequency (per day) for rats treated with the CMV-KCNA1 lentivector or its GFP-only control. Cumulative seizure counts were normalized to the number experienced by each animal in the 7 days preceding treatment.

Data are presented as mean±SEM.

Figure 4:
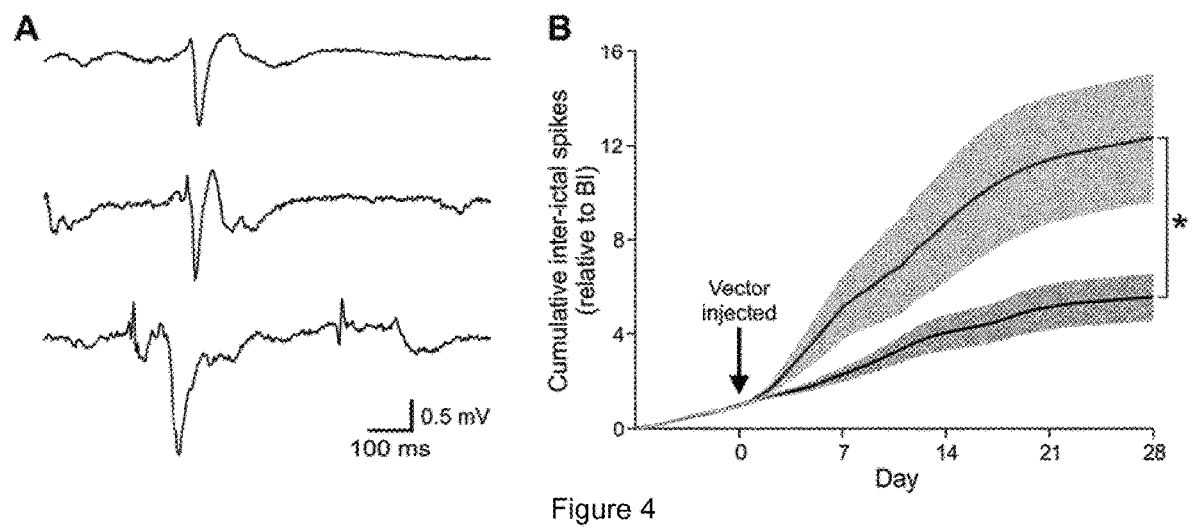

FIG. 4: Kv1.1 overexpression with the CMV-KCNA1 lentivector suppresses inter-ictal spiking A. Example ECoG traces of inter-ictal spikes.

B. Cumulative inter-ictal spike frequency (per day) for rats treated with the CMV-KCNA1 lentivector (n=8) or its GFP-only control (n=7). Cumulative inter-ictal spike counts were normalized to the number experienced by each animal in the 7 days preceding treatment. The frequency of inter-ictal spikes was significantly reduced by treatment with the CMV-KCNA1 lentivector (cumulative values at day 28 compared with a Mann Whitney U test; p=0.04).

Figure 5:
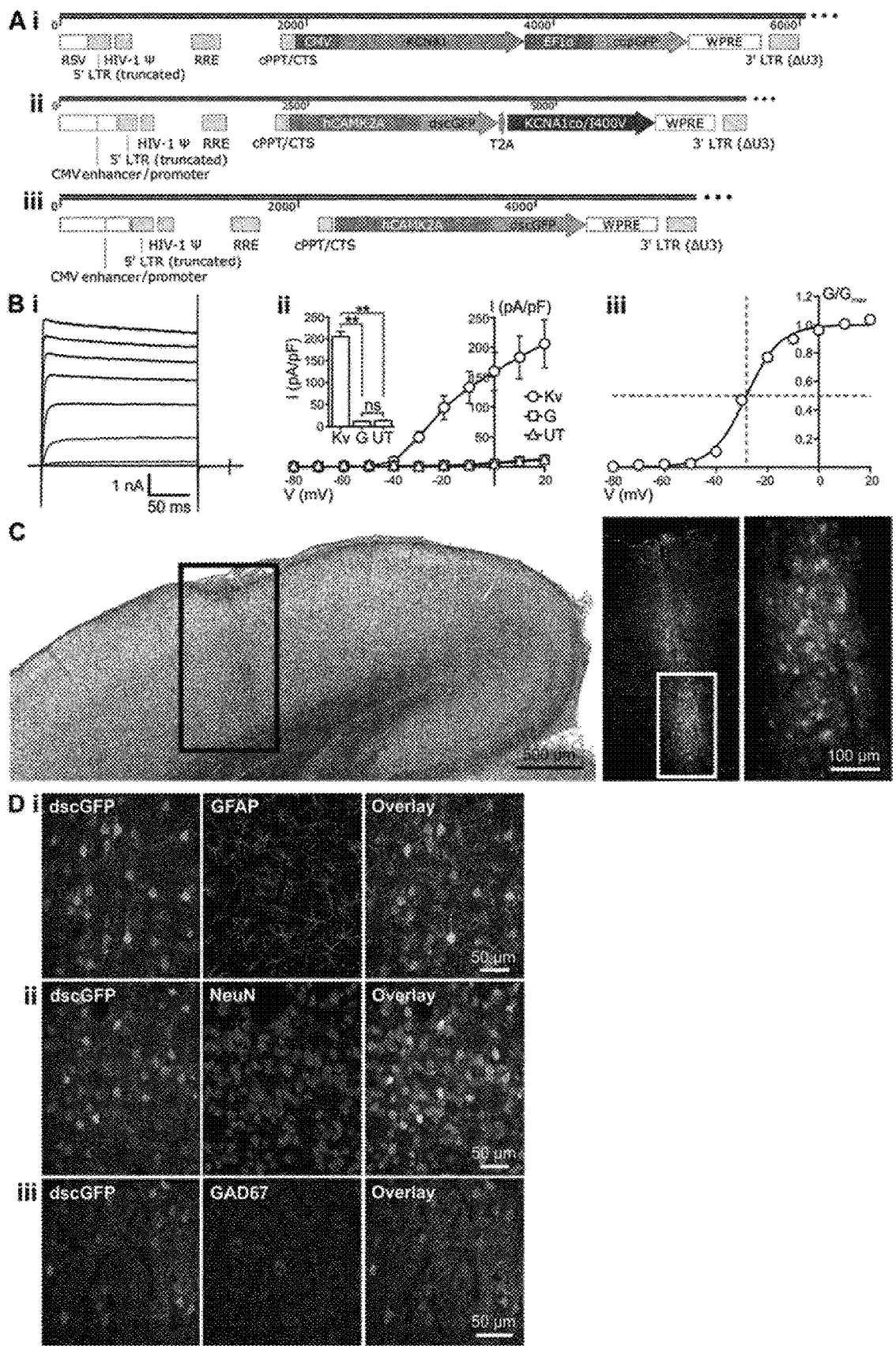

FIG. 5: Design and characterisation of an optimized KCNA1 gene therapy for clinical translation.

A. Lentiviral transfer plasmid maps for the CMV-KCNA1 pilot vector (i), the optimized EKC vector (ii) and its reporter-only control (iii). Abbreviations: RSV—Rous sarcoma virus promoter; LTR—long terminal repeat; HIV-1 Ψ—HIV-1 packaging signal; RRE—Rev response element; cPPT/CTS—central polypurine tract and central termination sequence; EF1α—elongation factor 1 α promoter; WPRE—woodchuck hepatitis virus post-transcriptional regulatory element.

B. Heterologous expression of functional Kv1.1 channels from the optimized EKC transfer plasmid. (i): Representative current-time trace from a Neuro-2a cell transfected with the EKC transfer plasmid. (ii): Plot of mean current density against voltage for cells transfected with the EKC transfer plasmid (Kv; n=13), cells transfected with the dscGFP-only control plasmid (G; n=8), and untransfected controls (UT; n=10). Inset: histogram showing differences in current density between the three groups during the voltage step to +20 mV (Kv vs. UT: p=0.0013; Kv vs. G: p=0.0012; UT vs. G: p=0.82; ns=not significant; Welch's one-way ANOVA with Games-Howell post-hoc tests). (iii): Plot of mean normalised conductance against voltage for cells transfected with the EKC transfer plasmid. Data are fit with a single Boltzmann function. The $V_{0.5}$ (voltage of half-maximal conductance) of −28.2 mV is similar to values obtained from human embryonic kidney 293 (HEK293) cells transfected with CMV-driven, wild-type KCNA1 (−32.8±0.9 mV) (Tomlinson et al., 2013). All error bars represent SEM.

C. Bright-field (left) and fluorescence (right) images of a brain slice from a rat injected in the left visual cortex with 1.25 μl (~3×10$^6$ infectious units (IU)) of the EKC lentivector showing a pattern of transduction similar to that of the CMV-KCNA1 vector.

D. Immunohistochemical assessment of the cell type specificity of EKC expression. (i): There was no overlap between lentivector-transduced neurons expressing dscGFP and astrocytes stained for GFAP. (ii): There was 100% overlap between dscGFP+ cells and neurons stained for NeuN. (iii): Minimal overlap was observed between dscGFP+ cells and inhibitory interneurons stained for GAD67.

Figure 6:
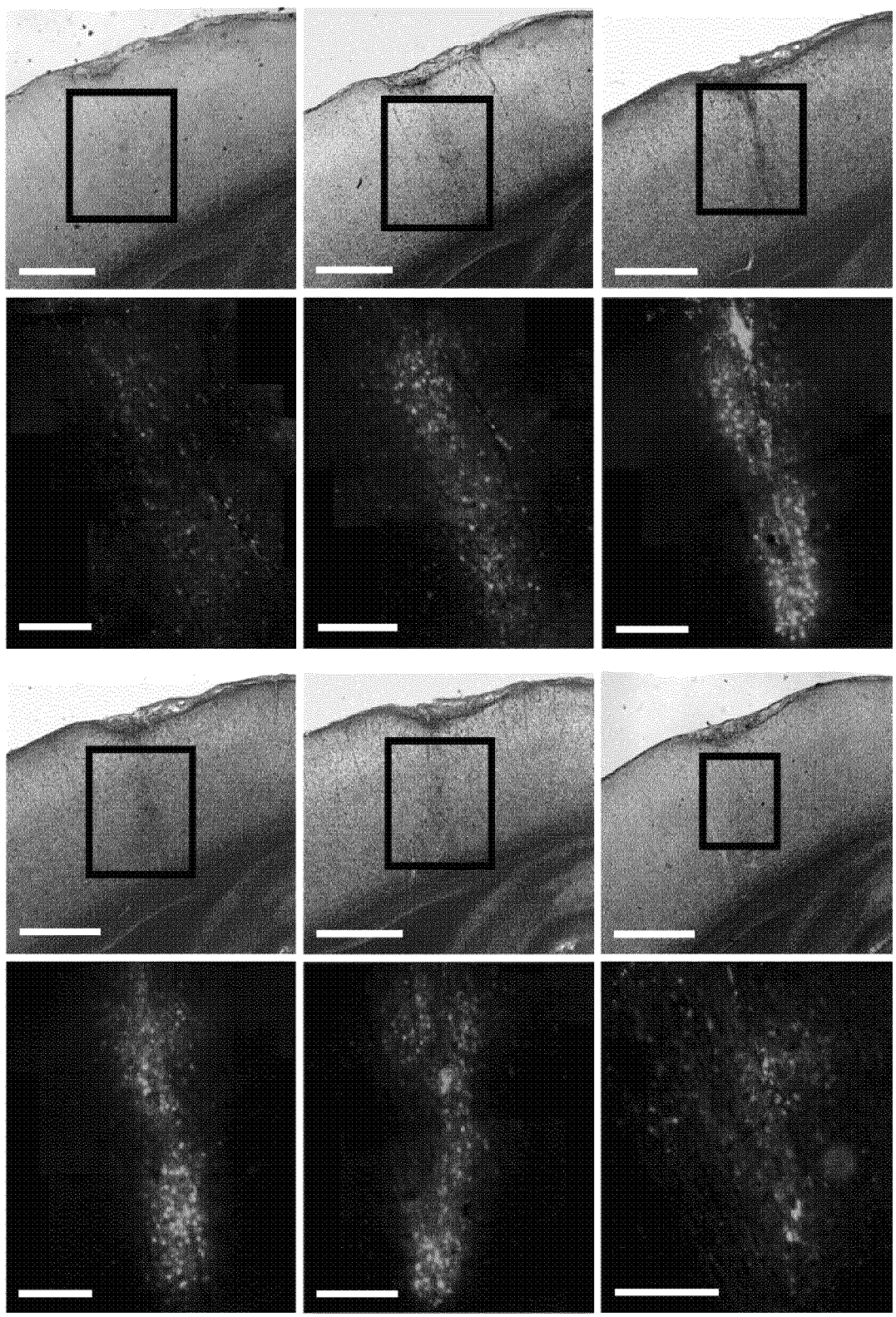

FIG. 6: Cortical spread of EKC lentivector transduction.

Bright-field and fluorescence images of 6 sequential left-hemisphere visual cortex slices (70 μm thick) from a rat brain injected with 1.25 μl (~3×10$^6$ IU) of the EKC lentivector. Slices are ordered from top left (rostral) to bottom right (caudal). Scale bars represent 600 μm and 200 μm for bright-field and fluorescence images, respectively.

Figure 7:
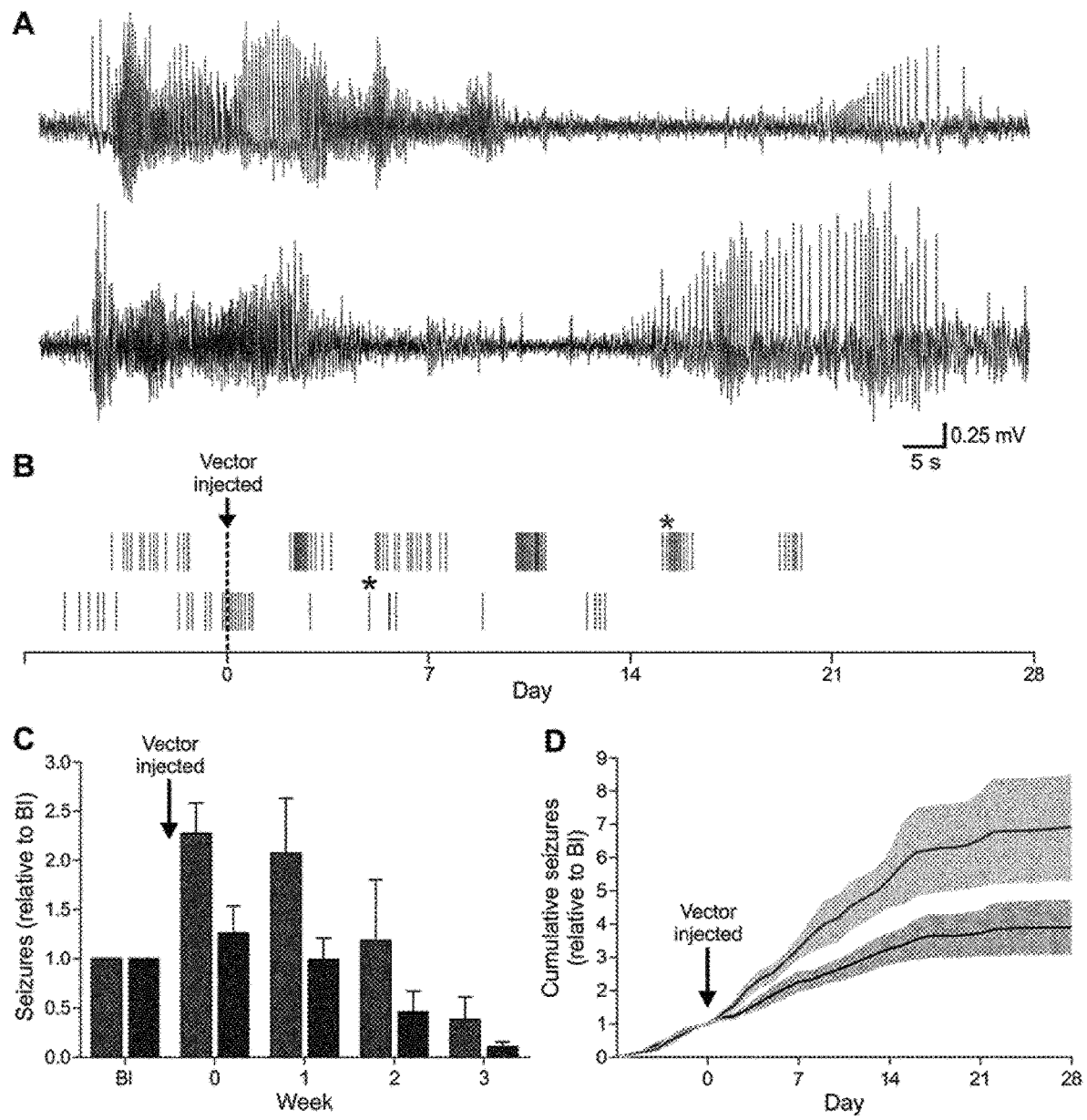

FIG. 7: EKC gene therapy robustly reduces seizure frequency in a blinded, randomised, pre-clinical trial.

A. Representative seizures from two animals after treatment with the EKC lentivector (bottom trace) or its dscGFP-only control (top trace).

B. Raster plots of all seizures experienced by the same animals over the full 5 weeks of recording. Seizures presented in panel A are marked by asterisks.

C. Normalized seizure frequency (per week) for rats treated with the EKC lentivector (n=7) or its reporter-only control (n=11). The EKC lentivector significantly reduced seizure frequency in the weeks following treatment.

D. Normalized cumulative seizure frequency (per day) for rats treated with the EKC lentivector or its reporter-only control.

Data are presented as mean±SEM.

EXAMPLES

Example 1

Demonstration of Delivery of an Engineered Potassium Channel Gene in Epilepsy Gene Therapy Materials and Methods Molecular Biology Lentiviral transfer plasmids were constructed using standard subcloning techniques. KCNA1 was codon optimized for human expression using GeneOptimizer® software, and synthesised using GeneArt® (Thermo Fisher Scientific). All plasmids were fully sequenced before use.

Voltage Clamp Recordings

Neuro-2a cells were obtained as a gift from the laboratory of S. Hart (UCL Institute of Child Health). Cells were grown in Gibco® Dulbecco's Modified Eagle Medium (DMEM)+ GlutaMAX™ (Thermo Fisher Scientific), supplemented with 10% heat-inactivated foetal bovine serum (Thermo Fisher Scientific), 1% penicillin/streptomycin (Thermo Fisher Scientific) and 1% non-essential amino acids (Sigma). Cultures were maintained in logarithmic growth phase in a humidified 5% $CO_2$ atmosphere at 37° C. Transfections were performed using TurboFect™ transfection reagent (Thermo Fisher Scientific) according to the manufacturer's instructions. Transfected cells were plated onto 13 mm borosilicate glass coverslips (VWR). Coverslips were placed into the chamber of a BX51WI fixed-stage upright microscope equipped with UMPLFLN 10× and LUMPLFLN 40× water-immersion objectives (Olympus). Coverslips were submerged in a static bath of extracellular solution with the following composition (in mM): 140 NaCl, 4 KCl, 1.8 $CaCl_2$, 2 $MgCl_2$, 10 HEPES (pH 7.35, osmolarity ~301 mOsm/L). Filamented borosilicate glass micropipettes (GC150-F; Warner Instruments) were pulled to tip resistances between 2.0 and 3.0 MΩ using a P-97 Flaming/Brown micropipette puller (Sutter Instrument Company). Micropipettes were filled with an intracellular solution of the following composition (in mM): 140 KCl, 10 HEPES, 10 EGTA (pH 7.35, osmolarity ~291 mOsm/L). Transfected cells were identified by their expression of the fluorescent marker dscGFP, excited with light of wavelength 488 nm. Macroscopic currents were recorded under voltage clamp using the whole-cell patch clamp configuration. The voltage step protocol used was as follows: cells were held at a resting potential of −80 mV and currents evoked by 200 ms depolarising steps delivered in 10 mV increments up to +20 mV. A 40 ms hyperpolarising step to −100 mV was included before returning to baseline. Data were filtered at 3 kHz and acquired at 10 kHz using WinWCP software (J. Dempster, University of Strathclyde) and an Axon Multiclamp 700B amplifier (Molecular Devices). Series resistance compensation was employed throughout, with prediction and correction components adjusted to 80% and the bandwidth set to 1.2 kHz. Cells with series resistance greater than 10 MΩ were excluded from the analysis. All recordings were made at room temperature (23-26° C.). The liquid junction potential, calculated to be +4.1 mV, was left uncorrected. Leak currents were minimal and left unsubtracted.

For analysis, evoked currents were taken as the steady-state current in the last 40 ms of each voltage step. Baseline holding currents were subtracted before division by cell capacitance to generate current density values. To calculate normalised conductance, the current density at each voltage step was divided by the step potential minus the potassium reversal potential (−91.34 mV). This generates raw conductance values that are corrected for the variation in $K^+$ driving force which accompanies stepwise changes in membrane potential. Plots of raw conductance against voltage for each EKC-transfected cell were fit with individual Boltzmann functions given by the equation:

$$G = A_2 + \frac{A_1 - A_2}{1 + e^{\frac{V - V_{0.5}}{k}}}$$

where G is the conductance, V the voltage, $A_1$ the initial (minimum) conductance, $A_2$ the final (maximum) conductance, $V_{0.5}$ the voltage of half-maximal conductance, and k the slope factor. Raw conductance values were normalised to $A_1$ and $A_2$ of their own Boltzmann functions.

Raw conductance values were normalised to $A_1$ and $A_2$ of their own Boltzmann functions. Normalised conductance was then plotted against voltage for each EKC-transfected cell and again fit with individual Boltzmann functions. The mean adjusted $R^2$ and $V_{0.5}$ values presented in the results were extracted from these fits. For FIG. 5Biii, mean normalised conductance across cells was plotted against voltage before fitting with a final Boltzmann function. In line with convention, adjusted $R^2$ and $V_{0.5}$ values for this fit were not reported.

Lentiviral Synthesis

The CMV-KCNA1 lentivector was identical to that used in Wykes et al., 2012 and has the nucleotide sequence shown in SEQ ID NO: 6.

HEK293 producer cells were grown in Gibco® DMEM+GlutaMAX™, supplemented with 10% heat-inactivated foetal bovine serum and 1% penicillin/streptomycin. Cultures were maintained in logarithmic growth phase in a humidified 5% $CO_2$ atmosphere at 37° C. Cells were split every 3-4 days using 0.05% Trypsin-EDTA (Thermo Fisher Scientific) and never grown for more than 15 passages. For lentiviral synthesis, cells were grown to a confluency of ~70% and transiently co-transfected with pMDG-VSV.G, pCMVdR8.74$^{D64V}$, and either the EKC transfer plasmid or its dscGFP-only control. pMDG-VSV.G and pCMVdR8.74$^{D64V}$ were obtained as gifts from the laboratory of A. J. Thrasher and W. Qasim (UCL Institute of Child Health). pMDG(VSV-G) encodes the envelope glycoprotein of the vesicular stomatitis virus. Lentivectors pseudotyped with VSV-G display a broad tropism and are relatively resistant to mechanical destruction during ultracentrifugation (Burns et al., 1993). pCMVdR8.74$^{D64V}$ is a $2^{nd}$ generation human immunodeficiency virus 1 (HIV-1) packaging plasmid with an aspartic acid$^{64}$-valine mutation in its integrase coding sequence. This mutation reduces genomic integration by a factor of 10,000 compared to wild-type levels (Leavitt et al., 1996). The mass ratio of envelope to packaging to transfer plasmids was 1:2.5:1.5. Transfections were performed using Lipofectamine® 2000 transfection reagent (Thermo Fisher Scientific) at approximately 160 µl per 100 µg of total plasmid DNA. The transfection medium was removed after 18 hours and replaced with fresh medium. Two media harvests were collected, at 40 hours and 60 hours following transfection. Special care was taken to minimise cell detachment during each harvest. Harvested media were pre-cleaned by centrifugation at 1000 rpm for 3 min at 4° C., filtered through 0.45 µm micropores and stored at 4° C. Media were overlaid on a sucrose solution with the following composition (in mM): 50 Tris-HCl, 100 NaCl, 0.5 EDTA (pH 7.4, 10% w/v sucrose), and centrifuged at 20,000 rpm for 2 hr at 4° C. The supernatant was discarded and lentiviral pellet resuspended in sterile PBS. Lentiviral suspensions were aliquoted and snap-frozen in liquid nitrogen before long-term storage at −80° C. A rough approximation of viral titre was obtained using the Lenti-X™ p24 rapid titer kit (Clontech). Each titration was performed in triplicate with 3 separate aliquots of each virus. Estimated titres were $2.42 \times 10^9$ IU/ml (EKC) and $4.26 \times 10^9$ IU/ml (control).

Surgical Procedures

All experiments were performed in accordance with the United Kingdom Animal (Scientific Procedures) Act 1986. Adult male rats (Sprague Dawley, Long-Evans or Lister Hooded; 300-400 g) were anaesthetized and placed into a stereotaxic frame (Kopf). 15 ng of TeNT (a gift from the laboratory of G. Schiavo (UCL Institute of Neurology)) was injected into layer 5 of the right visual cortex in a final volume of 1.0 µl at a rate of 100 nl min$^{-1}$ (coordinates: 3 mm lateral, 7 mm posterior of bregma; 1.0 mm deep from the pia). An ECoG transmitter (A3028E; Open Source Instruments, MA, USA) was implanted subcutaneously with a subdural intracranial recording electrode positioned above the injection site. A reference electrode was implanted in the contralateral skull. A cannula (Plastics One) was positioned above the injection site for delivery of lentiviral vectors 11 or 14 days later. Each rat received a maximum of 2.0 µl of lentivirus injected directly into the seizure focus. Animals injected with TeNT were housed separately in Faraday cages for the duration of the study.

ECoG Acquisition and Analysis

ECoG was recorded continuously for up to 6 weeks after surgery. Data were acquired using hardware and software purchased from Open Source Instruments. The method of seizure detection differed for the characterisation of the model, the pilot study and the final preclinical experiment. For the model characterisation, seizures were detected by continuous observation of the entire ECoG dataset by a neurologist. For the pilot study, ECoG traces were first divided into 1 s epochs. Four metrics (power, coastline, intermittency and coherence) were quantified for each epoch, and their values compared to those from a user-curated library of epochs validated by video as representing seizure activity (Wykes et al., 2012). Matched values were fed into a consolidation script that returned all instances of 5 or more sequential epochs identified as containing seizure activity. All seizures in the consolidation output were verified by an experimenter. For the final preclinical trial, 6 metrics were quantified for each epoch (power, coastline, intermittency, coherence, asymmetry and rhythm) and all matched values were checked for seizure activity without the use of a consolidation script. Seizure counts in this experiment were performed by an experimenter blinded to the treatment. For all datasets the minimum duration for a seizure was set at 10 s.

Behavioural Seizure Assessment

Assessment of the behavioural correlates of electrographic seizures was carried out by a neurologist. Seizures were randomly selected from the 5 weeks of recording, and associated behaviours observed using top-down video footage time-locked to the ECoG trace.

Immunohistochemistry 1 week after lentivirus injection rats were terminally anaesthetised with sodium pentobarbital (Euthatal; Merial) and transcardially perfused with cold (4° C.) heparinised PBS (80 mg/litre heparin sodium salt; Sigma) followed by 4% paraformaldehyde (PFA) in PBS (Santa Cruz Biotechnology). Brains were removed and post-fixed in 4% PFA at 4° C. for a further 24 hours. After washing in PBS brains were sliced into 70 µm coronal sections using a vibrating microtome (Leica). Slices were stored free-floating at 4° C. in PBS plus 0.02% sodium azide (Sigma). For antibody staining, slices were permeabilised for 20 minutes in PBS plus 0.3% Triton X-100 (Sigma) before blocking for 1 hour in PBS plus 0.3% Triton X-100 (Sigma), 1% bovine serum albumin (Sigma) and 4% goat serum (Sigma). Slices were incubated overnight at 4° C. in PBS plus 0.3% Triton X-100 and rabbit anti-NeuN (diluted 1:750; ab177487; Abcam), mouse anti-GFAP (diluted 1:500; MAB3402; Merck Millipore) or mouse anti-GAD67 (diluted 1:500; MAB5406; Merck Millipore) primary antibodies. After three 10 minute washes in PBS, slices were incubated at room temperature for 3 hours in PBS plus the relevant Alexa Fluor® 594-conjugated secondary antibody (goat anti-rabbit (A-11037; Thermo Fisher Scientific) or goat anti-mouse (A-11005; Thermo Fisher Scientific); both diluted 1:750). After a further three 10 minute washes in PBS, slices were mounted onto plain glass microscope slides (Thermo Fisher Scientific) using Vectashield® HardSet™ mounting medium (Vector Laboratories) and borosilicate glass coverslips (VWR). Bright-field and fluorescence images were acquired using one of two microscopes: an Axio Imager Al fluorescence microscope (Axiovision LE software) equipped with 2.5×, 10× and 40× EC Plan-Neofluar non-immersion objectives, or an inverted LSM 710 confocal laser scanning microscope (ZEN 2009 software) equipped with 40× and 63× EC Plan-Neofluar oil-immersion objectives (Zeiss). For the confocal microscope, dscGFP and Alexa Fluor® 594 were excited with the 488 nm and 561 nm lines of an argon or diode pumped solid state (DPSS) laser, respectively. All image processing was performed using ImageJ software. Composite images were assembled using the MosaicJ ImageJ plugin.

Statistics

Efficacy of treatment data (FIGS. 3D, 7C) were analysed using a generalized log-linear mixed model with random effect of animal (autoregressive covariance) and fixed effects of treatment group, week, and the interaction between treatment group and week. Seizure counts in the week preceding treatment (FIG. 7C) were compared using a Mann Whitney U test. Current densities at +20 mV (FIG. 5Bii) were compared using a Welch's one-way ANOVA followed by Games-Howell post-hoc tests.

Results

Injection of TeNT into the Visual Cortex Produces a Model of Focal Epilepsy with Discrete Seizures Starting with a model developed in mice (Mainardi et al., 2012), we characterized the electrographic features, temporal evolution, and behavioural correlates of seizures evoked by injection of TeNT into the visual cortices of 9 adult male Sprague Dawley rats. In striking contrast to the brief, near-continuous epileptiform discharges seen following TeNT injection into the motor cortex (Wykes et al., 2012), injection into the visual cortex produced discrete spontaneous seizures (FIG. 1A). Seizures emerged approximately 4 days after the injection of TeNT, increased in frequency over 7-10 days, reached a plateau for 2-3 weeks, and resolved in most animals after 5 or 6 weeks (FIGS. 1B, C). The total number of seizures experienced by each animal was highly variable. Average seizure duration evolved over time, increasing from just under 50 s in the first week to approximately 100 s for the next four (FIG. 1D). Time-locked video-ECoG was employed to identify the behavioural correlates of a randomly selected subset of seizures (n=102; FIG. 1E). For 11 seizures (10.8%), associated behaviours were unobservable due to interrupted recordings or the animal remaining out of sight within its environmental enrichment material. All remaining seizures had observable behavioural correlates. For 45 seizures (44.1%) these were subtle, including repetitive eye blinking, sudden increases in agitation or aggressive searching behaviour. Unilateral motor involvement, e.g. twitching of the contralateral limb, was observed for 19 seizures (18.6%), with bilateral motor symptoms seen in a further 6 (5.9%). 21 seizures (20.6%) developed into full bilateral tonic-clonic seizures. This model of focal neocortical epilepsy was not strain-specific; similar seizures were evoked in both Lister Hooded and Long-Evans rats (FIG. 2).

A Pilot Study Shows KCNA1 Gene Therapy is Sufficient to Reduce Spontaneous Seizures We asked whether the CMV-driven Kv1.1 vector (CMV-KCNA1) used earlier in a model of EPC (Wykes et al., 2012) remained effective against these longer and more complex seizures. Two weeks after the injection of TeNT, following the establishment of spontaneous seizures, animals were randomly divided into 2 groups and injected via pre-implanted cannula with either the CMV-KCNA1 lentivector or a control lentivector expressing only green fluorescent protein (GFP). ECoG recordings were continued for a further 4 weeks. As previously observed (Wykes et al., 2012), the CMV-KCNA1 lentivector transduced neurons within a narrow column of the cortex (FIG. 3A). Given the high variability in total seizure counts, to compare seizure frequency between the two treatment groups the numbers of seizures experienced each week were normalized to the number experienced by each animal in the week preceding treatment (baseline week (BI)). The CMV-KCNA1 lentivector significantly reduced normalized seizure frequency in the weeks following treatment (generalized log-linear mixed model on weeks 0-3, treatment*week interaction effect: $F(1,60)=69.499$, $p<0.001$; FIG. 3D). The therapeutic effect emerged rapidly; plots of cumulative daily seizure frequency for the two treatment groups begin to diverge within 3 days of lentivector injection (FIG. 3E). Kv1.1 overexpression did not influence seizure duration (data not shown).

Epilepsy is associated with a number of comorbidities. Among these are cognitive deficits which in temporal lobe epilepsies strongly correlate to inter-ictal discharges (Holmes G L 2013, Bragatti J A et al 2014, Dinkelacker V et al 2016). Similarly, in the neocortex inter-ictal activity is likely to cause significant disruption to normal brain function. In addition to its suppression of seizure frequency, Kv1.1 overexpression with the CMV-KCNA1 lentivector significantly reduced the frequency of inter-ictal discharges, another signature consistent with epileptogenesis (FIG. 4).

Because our model of focal neocortical epilepsy was not strain-specific (FIG. 2), this initial study included 16 animals from 3 different strains (Sprague Dawley, Lister Hooded and Long-Evans). To ensure that the positive effect of CMV-KCNA1 treatment was not biased by the minority of Lister Hooded and Long-Evans animals, seizure frequency data were reanalysed for the Sprague Dawley animals only. Despite the small sample size (6 treated vs. 5 controls), the CMV-KCNA1 lentivector still significantly reduced normalized seizure frequency in the weeks following treatment (generalized log-linear mixed model on weeks 0-3, treatment*week interaction effect: $F(1,40)=4.851$, $p=0.033$). This pilot study therefore strongly suggests that over-expression of KCNA1 is sufficient to reduce the number of discrete spontaneous seizures.

Design and Characterisation of a Gene Therapy Tool Optimized for Clinical Translation To bring KCNA1 gene therapy closer to the clinic, we designed a new lentiviral transfer plasmid (FIG. 5Aii). The CMV promoter from the original CMV-KCNA1 construct (FIG. 5Ai) was replaced with a 1.3 kb human CAMK2A promoter (hCAMK2A) to bias expression to excitatory neurons (Dittgen et al., 2004; Yaguchi et al., 2013). The KCNA1 gene was codon-optimized for expression in human cells, and mutated to introduce an I400V amino acid change normally generated by RNA-editing. The I400V substitution elicits a 20-fold increase in the rate at which Kv1.1 channels recover from inactivation (Bhalla et al., 2004). For preclinical evaluation, a dscGFP reporter gene was linked to the engineered potassium channel (EKC) gene by a T2A peptide, which permits dual protein expression from a single promoter.

The salient components of our EKC lentiviral transfer plasmid (FIG. 5Aii) include:

1) A 1.3 kb human CAMK2A promoter (hCAMK2A) comprising 100 bp of the 5' untranslated region of CAMK2A coupled to 1.2 kb of upstream DNA. A murine Camk2a promoter of similar size has been shown to drive pyramidal neuron-specific gene expression in lentiviral-injected rat barrel cortex (Dittgen et al., 2004) and primate motor cortex (Yaguchi et al., 2013). This contrasts with the CMV promoter of our pilot vector, which is known to drive transgene expression preferentially within glia following lentiviral injection into the primate rhinal (Lerchner et al., 2014) or motor (Yaguchi et al., 2013) cortices.

2) An engineered potassium channel gene consisting of a codon-optimized KCNA1 with an adenine$^{1998}$>guanine point mutation to modify channel inactivation properties. Codon optimization is useful beyond the benefit of increased Kv1.1 expression. It permits specific tracking of transgene expression with RNA-targeted techniques that would otherwise fail to distinguish between transgenic and endogenous KCNA1. Such tracking will prove particularly useful further along the translation pipeline with vectors that necessarily lack coding sequences for fluorescent reporter proteins. At negative membrane potentials, channels containing unedited I$^{400}$ recover from inactivation at a rate around twenty times slower than their edited (V$^{400}$) counterparts (Bhalla et al., 2004). Because Kv1.1 channels that recover faster from inactivation would be expected to dampen neuronal excitability, we decided to pre-empt the RNA edit in our codon-optimized KCNA1 by purposefully introducing the A$^{1998}$G point mutation.

3) A superbright dscGFP reporter gene linked to EKC by a T2A peptide. 2A peptides are short (~20 amino acids) sequences that permit multicistronic gene expression from single promoters by impairing peptide bond formation during ribosome-mediated translation (Szymczak and Vignali, 2005). Importantly, genes either side of a 2A peptide are expressed in a 1:1 ratio with translation taking place simultaneously. As such, reporter expression serves as a very reliable indicator of therapeutic transgene expression. This set-up contrasts with that of our pilot vector, where therapeutic and reporter transgenes were placed under the transcriptional control of separate and distinct promoters.

The EKC transfer plasmid used in these experiments has the sequence shown in SEQ ID NO: 7. The sequence of the dscGFP-only control transfer plasmid has the sequence shown in SEQ ID NO: 8.

To determine whether the optimized transfer plasmid could be decoded to produce functional Kv1.1 channels, Neuro-2a cells were transiently transfected with the EKC or dscGFP-only control transfer plasmids and subjected to whole-cell patch clamping. Cells exposed to the transfection mixture but lacking dscGFP fluorescence were used as a second set of controls. A typical voltage step protocol evoked negligible outward currents in both control groups, while Neuro-2a cells transfected with the EKC transfer plasmid displayed large voltage-dependent currents that peaked in amplitude at several nanoamps (FIG. 5Bi,ii). Current densities at the largest depolarising voltage step (+20 mV) were significantly larger in EKC-transfected cells than controls, which displayed only small endogenous voltage-dependent currents (FIG. 5Bii). There was no significant difference in current density between untransfected cells and cells transfected with the control plasmid (FIG. 5Bii). To determine if our molecular optimizations influenced the voltage dependence of Kv1.1 channel activation, normalised conductance-voltage plots were fit with individual Boltzmann functions for each EKC-transfected cell. A mean adjusted $R^2$ of $0.995 \pm 0.0007$ demonstrated a good fit across all cells. The mean $V_{0.5}$ of $-28.2 \pm 0.4$ mV was similar to values obtained from HEK293 cells transfected with CMV-driven, wild-type KCNA1 ($-32.8 \pm 0.9$ mV) (Tomlinson et al., 2013). A plot of mean normalised conductance against voltage for all SKC-transfected cells, fit with its own Boltzmann function, is provided in FIG. 5Biii. Together these data indicate that the optimized EKC transfer plasmid supports the generation of robust Kv1.1 currents.

The EKC transfer plasmid was packaged into a non-integrating lentiviral vector (Yáñez-Muñoz et al., 2006). When injected into the rat visual cortex, this lentivector drove strong, localised expression of the dscGFP reporter (FIG. 5C). Imaging of sequential brain slices produced an estimated transduction volume of ~0.075 mm3 (FIG. 6).

Immunohistochemistry revealed no visible overlap between dscGFP expression and glial fibrillary acidic protein (GFAP) staining (0/512 dscGFP+ cells co-localized with GFAP, n=3 animals; FIG. 5Di). In contrast, all dscGFP+ cells co-localized with the neuronal marker NeuN (714/714, n=3 animals; FIG. 5Di). These data indicate that transgene expression from the EKC lentivector is restricted to neurons. There was minimal overlap between dscGFP expression and staining for glutamic acid decarboxylase 67 (GAD67), an enzymatic marker for GABAergic neurons (3/603 dscGFP+ cells co-localized with GAD67, n=3 animals; FIG. 3Diii). This suggests that EKC transgene expression is largely restricted to excitatory neurons.

EKC Gene Therapy Reduces Seizure Frequency in a Randomised, Blinded, Preclinical Trial To test the efficacy of the EKC lentivector, we designed a randomised, blinded preclinical trial to mimic clinical trial conditions, and selected reduced seizure frequency as the primary outcome measure. A new batch of TeNT with slightly reduced potency produced fewer overall seizures and improved animal welfare. Eleven days after the injection of TeNT, 26 Sprague Dawley rats were randomly divided into 2 groups and injected via pre-implanted cannula with either the EKC lentivector or a dscGFP-only control vector. ECoG recordings were continued for a further 4 weeks. The timeline was altered from that of the pilot study to treat after 11 days in order to capture the period when seizure activity is at its highest (2-4 weeks following TeNT). To minimise the confounding influence of animals that failed to develop robust epilepsy, subjects were excluded if they experienced fewer than 5 seizures in the week preceding treatment. This criterion, applied prior to unblinding, led to the exclusion of 8 animals (6 EKC, 2 control). There was no significant difference between treatment groups in the number of seizures experienced in the week preceding virus injection (Mann Whitney U test, p=0.185). Analysis of the primary outcome measure indicated that EKC treatment produced a robust decrease in seizure frequency over time (generalized log-linear mixed model on weeks 0-3, treatment*week interaction effect: $F(1,67)=29.704$, $p<0.001$; FIG. 7C). As in the pilot study, the effect lasted for the duration of recording, and the absolute effect size only decreased as seizures abated in the control group. Again, the therapeutic effect emerged rapidly, with plots of cumulative daily seizure frequency for the two groups starting to diverge 2 days after treatment (FIG. 7D).

Discussion

EKC gene therapy represents an effective new treatment for focal neocortical seizures in a format adapted to improve safety and translation to the clinic.

We have previously shown that overexpression of Kv1.1 can reduce the frequency of epileptiform discharges in a motor cortex TeNT model of EPC (Wykes et al., 2012). However, it was unclear whether Kv1.1 overexpression would be sufficient to inhibit discrete long-lasting seizures. We show here, in two independent experiments, that Kv1.1 overexpression is indeed sufficient to reduce seizure frequency. The effect on seizure number is pronounced, but once initiated the seizures progress in a similar pattern with similar electrographic features in both treated and control animals.

Injection of TeNT into the occipital cortex induced seizures that lasted markedly longer (50-150 s) than those induced by TeNT injection in motor cortex (<1 s) (Wykes et al., 2012). The difference, which parallels that seen with occipital lobe seizures and EPC in human patients, may be a consequence of different connectivity in the occipital and motor cortices. Further studies will be needed to determine how cortical architecture impacts the type of epileptiform activity induced by TeNT insult.

Lentiviral gene therapy approaches are becoming more common in CNS disorders, and have shown good safety and tolerability even in extended trials (Palfi et al., 2014). In the case of epilepsy, an additional safety concern is the possibility of potassium channel overexpression in interneurons, which could aggravate seizure activity by exacerbating rather than attenuating local excitability. To mitigate this risk we have utilised a human CAMK2A promoter that in rats leads to very little expression in GABAergic cells. Our estimate of specificity may even be slightly conservative as a small proportion of excitatory pyramidal neurons in the rodent cortex stain positively for GABA as well as glutamate (Hill et al., 2000; Lavdas et al., 1996), and may therefore express GAD67 despite pyramidal morphology and physiology.

Because the role of potassium channels, including Kv1.1, in regulating neuronal excitability is conserved across a broad range of neurons, potassium channel overexpression may hold therapeutic promise in the treatment of other diseases characterised by neuronal hyperexcitability. There is currently an unmet clinical need for new treatments for chronic pain, and a variety of gene therapy approaches aimed at reducing the excitability of dorsal root ganglion neurons have already demonstrated preclinical efficacy (Snowball and Schorge, 2015). Other disorders such as Parkinson's disease may be associated with excessive activity in specific groups of neurons (Lobb, 2014), and could be candidates for treatment if suitable cell type specific promoters can be identified.

REFERENCES

Baum, C., von Kalle, C., Staal, F. J. T., Li, Z., Fehse, B., Schmidt, M., Weerkamp, F., Karlsson, S., Wagemaker, G., and Williams, D. A. (2004). Chance or necessity? Insertional mutagenesis in gene therapy and its consequences. Mol. Ther. J. Am. Soc. Gene Ther. 9, 5-13.

Bhalla, T., Rosenthal, J. J. C., Holmgren, M., and Reenan, R. (2004). Control of human potassium channel inactivation by editing of a small mRNA hairpin. Nat. Struct. Mol. Biol. 11, 950-956.

Biffi, A., Montini, E., Lorioli, L., Cesani, M., Fumagalli, F., Plati, T., Baldoli, C., Martino, S., Calabria, A., Canale, S., et al. (2013). Lentiviral Hematopoietic Stem Cell Gene Therapy Benefits Metachromatic Leukodystrophy. Science 341, 1233158.

Bovolenta, R., Zucchini, S., Paradiso, B., Rodi, D., Merigo, F., Navarro Mora, G., Osculati, F., Berto, E., Marconi, P., Marzola, A., et al. (2010). Hippocampal FGF-2 and BDNF overexpression attenuates epileptogenesis-associated neuroinflammation and reduces spontaneous recurrent seizures. J. Neuroinflammation 7, 81.

Burns, J. C., Friedmann, T., Driever, W., Burrascano, M., and Yee, J. K. (1993). Vesicular stomatitis virus G glycoprotein pseudotyped retroviral vectors: concentration to very high titer and efficient gene transfer into mammalian and nonmammalian cells. Proc. Natl. Acad. Sci. U.S.A. 90, 8033-8037.

Cartier, N., Hacein-Bey-Abina, S., Bartholomae, C. C., Veres, G., Schmidt, M., Kutschera, I., Vidaud, M., Abel, U., Dal-Cortivo, L., Caccavelli, L., et al. (2009). Hematopoietic stem cell gene therapy with a lentiviral vector in X-linked adrenoleukodystrophy. Science 326, 818-823.

D'Adamo M C, Catacuzzeno L, Di Giovanni G, Franciolini F, Pessia M. (2013). K(+) channelepsy: progress in the neurobiology of potassium channels and epilepsy. Front. Cell. Neurosci. 7, 134

Devinsky, O. (2011). Sudden, unexpected death in epilepsy. N. Engl. J. Med. 365, 1801-1811.

Dittgen, T., Nimmerjahn, A., Komai, S., Licznerski, P., Waters, J., Margrie, T. W., Helmchen, F., Denk, W., Brecht, M., and Osten, P. (2004). Lentivirus-based genetic manipulations of cortical neurons and their optical and electrophysiological monitoring in vivo. Proc. Natl. Acad. Sci. U.S.A. 101, 18206-18211.

Galanopoulou, A. S., Buckmaster, P. S., Staley, K. J., Moshé, S. L., Perucca, E., Engel, J., Jr, Löscher, W., Noebels, J. L., Pitkänen, A., Stables, J., et al. (2012). Identification of new epilepsy treatments: issues in preclinical methodology. Epilepsia 53, 571-582.

Haberman, R. P., Samulski, R. J., and McCown, T. J. (2003). Attenuation of seizures and neuronal death by adeno-associated virus vector galanin expression and secretion. Nat Med 9, 1076-1080.

Hacein-Bey-Abina, S., Von Kalle, C., Schmidt, M., McCormack, M. P., Wulffraat, N., Leboulch, P., Lim, A., Osborne, C. S., Pawliuk, R., Morillon, E., et al. (2003). LMO2-associated clonal T cell proliferation in two patients after gene therapy for SCID-X1. Science 302, 415-419.

Heeroma, J. H., Henneberger, C., Rajakulendran, S., Hanna, M. G., Schorge, S., and Kullmann, D. M. (2009). Episodic ataxia type 1 mutations differentially affect neuronal excitability and transmitter release. Dis. Model. Mech. 2, 612-619.

Hill, E., Kalloniatis, M., and Tan, S. S. (2000). Glutamate, GABA and precursor amino acids in adult mouse neocortex: cellular diversity revealed by quantitative immunocytochemistry. Cereb. Cortex N. Y. N 1991 10, 1132-1142.

Hoppe, C., and Elger, C. E. (2011). Depression in epilepsy: a critical review from a clinical perspective. Nat. Rev. Neurol. 7, 462-472.

Kanter-Schlifke, I., Georgievska, B., Kirik, D., and Kokaia, M. (2007). Seizure suppression by GDNF gene therapy in animal models of epilepsy. Mol. Ther. J. Am. Soc. Gene Ther. 15, 1106-1113.

Kantor, B., McCown, T., Leone, P., and Gray, S. J. (2014). Chapter Two—Clinical Applications Involving CNS Gene Transfer. In Advances in Genetics, J.C.D. and S.F.G. Theodore Friedmann, ed. (Academic Press), pp. 71-124.

Kätzel, D., Nicholson, E., Schorge, S., Walker, M. C., and Kullmann, D. M. (2014). Chemical-genetic attenuation of focal neocortical seizures. Nat. Commun. 5, 3847.

Kullmann, D. M., Schorge, S., Walker, M. C., and Wykes, R. C. (2014). Gene therapy in epilepsy-is it time for clinical trials? Nat. Rev. Neurol. 10, 300-304.

Kwan, P., Schachter, S. C., and Brodie, M. J. (2011). Drug-resistant epilepsy. N. Engl. J. Med. 365, 919-926.

Lavdas, A. A., Mione, M. C., and Parnavelas, J. G. (1996). Neuronal clones in the cerebral cortex show morphological and neurotransmitter heterogeneity during development. Cereb. Cortex N. Y. N 1991 6, 490-497.

Leavitt, A. D., Robles, G., Alesandro, N., and Varmus, H. E. (1996). Human immunodeficiency virus type 1 integrase mutants retain in vitro integrase activity yet fail to integrate viral DNA efficiently during infection. J. Virol. 70, 721-728.

Lerchner, W., Corgiat, B., Der Minassian, V., Saunders, R. C., and Richmond, B. J. (2014). Injection parameters and virus dependent choice of promoters to improve neuron targeting in the nonhuman primate brain. Gene Ther.

Lin, E.-J. D., Young, D., Baer, K., Herzog, H., and During, M. J. (2006). Differential actions of NPY on seizure modulation via Y1 and Y2 receptors: evidence from receptor knockout mice. Epilepsia 47, 773-780.

Lobb, C. (2014). Abnormal Bursting as a Pathophysiological Mechanism in Parkinson's Disease. Basal Ganglia 3, 187-195.

Lundberg, C., Björklund, T., Carlsson, T., Jakobsson, J., Hantraye, P., Déglon, N., and Kirik, D. (2008). Applications of lentiviral vectors for biology and gene therapy of neurological disorders. Curr. Gene Ther. 8, 461-473.

Mainardi, M., Pietrasanta, M., Vannini, E., Rossetto, O., and Caleo, M. (2012). Tetanus neurotoxin-induced epilepsy in mouse visual cortex. Epilepsia 53, e132-136.

McCown, T. J. (2006). Adeno-associated Virus-Mediated Expression and Constitutive Secretion of Galanin Suppresses Limbic Seizure Activity in Vivo. Mol Ther 14, 63-68.

Ngugi, A. K., Bottomley, C., Kleinschmidt, I., Sander, J. W., and Newton, C. R. (2010). Estimation of the burden of active and life-time epilepsy: a meta-analytic approach. Epilepsia 51, 883-890.

Nikitidou, L., Torp, M., Fjord-Larsen, L., Kusk, P., Wahlberg, L. U., and Kokaia, M. (2014). Encapsulated galanin-producing cells attenuate focal epileptic seizures in the hippocampus. Epilepsia 55, 167-174.

Noe', F. M., Sørensen, A. T., Kokaia, M., and Vezzani, A. (2012). Gene therapy of focal onset epilepsy using adeno-associated virus vector-mediated overexpression of neuropeptide Y. In Jasper's Basic Mechanisms of the Epilepsies, J. L. Noebels, M. Avoli, M. A. Rogawski, R. W. Olsen, and A. V. Delgado-Escueta, eds. (Bethesda (Md.): National Center for Biotechnology Information (US)), p.

Palfi, S., Gurruchaga, J. M., Ralph, G. S., Lepetit, H., Lavisse, S., Buttery, P. C., Watts, C., Miskin, J., Kelleher, M., Deeley, S., et al. (2014). Long-term safety and tolerability of ProSavin, a lentiviral vector-based gene therapy for Parkinson's disease: a dose escalation, open-label, phase 1/2 trial. Lancet Lond. Engl. 383, 1138-1146.

Picot, M.-C., Baldy-Moulinier, M., Daurès, J.-P., Dujols, P., and Crespel, A. (2008). The prevalence of epilepsy and pharmacoresistant epilepsy in adults: a population-based study in a Western European country. Epilepsia 49, 1230-1238.

Rahim, A. A., Wong, A. M. S., Howe, S. J., Buckley, S. M. K., Acosta-Saltos, A. D., Elston, K. E., Ward, N. J., Philpott, N. J., Cooper, J. D., Anderson, P. N., et al. (2009). Efficient gene delivery to the adult and fetal CNS using pseudotyped non-integrating lentiviral vectors. Gene Ther. 16, 509-520.

Richichi, C., Lin, E.-J. D., Stefanin, D., Colella, D., Ravizza, T., Grignaschi, G., Veglianese, P., Sperk, G., During, M. J., and Vezzani, A. (2004). Anticonvulsant and antiepileptogenic effects mediated by adeno-associated virus vector neuropeptide Y expression in the rat hippocampus. J. Neurosci. Off. J. Soc. Neurosci. 24, 3051-3059.

Schuele, S. U., and Lüders, H. O. (2008). Intractable epilepsy: management and therapeutic alternatives. Lancet Neurol. 7, 514-524.

Snowball, A., and Schorge, S. (2015). Changing channels in pain and epilepsy: Exploiting ion channel gene therapy for disorders of neuronal hyperexcitability. FEBS Lett. 589, 1620-1634.

Streit A K, Derst C, Wegner S, Heinemann U, Zahn R K, Decher N. (2011) RNA editing of Kv1.1 channels may account for reduced ictogenic potential of 4-aminopyridine in chronic epileptic rats. Epilepsia. 52, 645-8

Streit A K, Matschke L A, Dolga A M, Rinné S, Decher N. (2014). RNA editing in the central cavity as a mechanism to regulate surface expression of the voltage-gated potassium channel. J Biol Chem. 289, 26762-71

Szymczak, A. L., and Vignali, D. A. A. (2005). Development of 2A peptide-based strategies in the design of multi-cistronic vectors. Expert Opin. Biol. Ther. 5, 627-638.

Tomlinson, S. E., Rajakulendran, S., Tan, S. V., Graves, T. D., Bamiou, D. E., Labrum, R. W., Burke, D., Sue, C. M., Giunti, P., Schorge, S., et al. (2013). Clinical, genetic, neurophysiological and functional study of new mutations in episodic ataxia type 1. J Neurol Neurosurg Psychiatry.

Woldbye, D. P. D., Angehagen, M., Gøotzsche, C. R., Elbrønd-Bek, H., Sørensen, A. T., Christiansen, S. H., Olesen, M. V., Nikitidou, L., Hansen, T. V. O., Kanter-Schlifke, I., et al. (2010). Adeno-associated viral vector-induced overexpression of neuropeptide Y Y2 receptors in the hippocampus suppresses seizures. Brain J. Neurol. 133, 2778-2788.

Wykes, R. C., Heeroma, J. H., Kullmann, D. M., Walker, M. C., and Schorge, S. (2011) Lentiviral-mediated overexpression of the potassium channel Kv1.1 as a treatment for focal neocortical epilepsy. Poster No. 248.20/S6. 2011 Neuroscience Meeting Planner. Washington, D.C.: Society for Neuroscience, 2011. Online.

Wykes, R. C., Heeroma, J. H., Mantoan, L., Zheng, K., MacDonald, D. C., Deisseroth, K., Hashemi, K. S., Walker, M. C., Schorge, S., and Kullmann, D. M. (2012). Optogenetic and potassium channel gene therapy in a rodent model of focal neocortical epilepsy. Sci. Transl. Med. 4, 161ra152.

Wykes, R. C. and Lignani. G (2018). Gene therapy and editing: Novel potential treatments for neuronal channelopathies. Neuropharmacology. 132, 108-117

Yaguchi, M., Ohashi, Y., Tsubota, T., Sato, A., Koyano, K. W., Wang, N., and Miyashita, Y. (2013). Characterization of the properties of seven promoters in the motor cortex of rats and monkeys after lentiviral vector-mediated gene transfer. Hum. Gene Ther. Methods 24, 333-344.

Yáñez-Muñoz, R. J., Balaggan, K. S., MacNeil, A., Howe, S. J., Schmidt, M., Smith, A. J., Buch, P., MacLaren, R. E., Anderson, P. N., Barker, S. E., et al. (2006). Effective gene therapy with nonintegrating lentiviral vectors. Nat. Med. 12, 348-353.

```
                            Sequence Annex

Nucleotide sequence of an exemplary engineered human KCNA1 gene
(SEQ ID NO: 1)
ATGACCGTGATGAGCGGCGAGAACGTGGACGAGGCCTCTGCCGCTCCTGGACACCCTCAGGATGGC
AGCTATCCCAGACAGGCCGACCACGACGATCACGAGTGCTGCGAGCGGGTCGTGATCAACATCAGC
GGCCTGAGATTCGAGACACAGCTGAAAACCCTGGCCCAGTTCCCCAACACCCTGCTGGGCAACCCC
AAGAAACGGATGCGGTACTTCGACCCCCTGCGGAACGAGTACTTCTTCGACCGGAACCGGCCCAGC
TTCGACGCCATCCTGTACTACTACCAGAGCGGCGGACGAGCTGCGGAGGCCCGTGAATGTGCCCCTG
GACATGTTCAGCGAGGAAATCAAGTTCTACGAGCTGGGCGAGGAAGCCATGGAAAAGTTCAGAGAG
GACGAGGGCTTCATCAAAGAGGAAGAGAGGCCCCTGCCCGAGAAAGAATACCAGAGACAAGTGTGG
CTGCTGTTCGAGTACCCCGAGTCTAGCGGCCCTGCCAGAGTGATCGCCATCGTGTCCGTGATGGTC
ATCCTGATCTCTATCGTGATCTTCTGCCTGGAAACCCTGCCTGAGCTGAAGGACGACAAGGACTTC
ACCGGCACCGTGCACCGGATCGACAACACCACCGTGATCTACAACAGCAATATCTTCACCGACCCA
TTCTTCATCGTGGAAACACTGTGCATCATCTGGTTCAGCTTCGAGCTGGTCGTGCGGTTCTTCGCC
TGCCCCAGCAAGACCGACTTCTTCAAGAACATCATGAACTTCATTGATATCGTGGCCATCATCCCC
TACTTCATCACCCTGGGCACCGAGATCGCCGAGCAGGAAGGCAATCAGAAGGGCGAGCAGGCCACC
AGCCTGGCCATTCTGAGAGTGATCAGACTCGTGCGGGTGTTCCGGATCTTCAAGCTGAGCCGGCAC
AGCAAGGGCCTGCAGATCCTGGGCCAGACACTGAAGGCCAGCATGAGAGAGCTGGGCCTGCTGATC
TTCTTTCTGTTCATCGGCGTGATCCTGTTCAGCAGCGCCGTGTACTTCGCCGAGGCCGAAGAAGCC
GAGAGCCACTTCAGCTCTATCCCCGACGCCTTTTGGTGGGCCGTGGTGTCCATGACCACAGTGGGC
TACGGCGACATGTAnCCCGTGACAATCGGCGGCAAGATCGTGGGCAGCCTGTGTGCCATTGCCGGC
GTGCTGACAGTCGCCCTGCCTGTGCCTGTGATCGTGTCCAACTTCAACTACTTCTACCACCGGGAA
ACCGAGGGGGAGGAACAGGCTCAGCTGCTGCACGTGTCCAGCCCCAATCTGGCCAGCGACAGCGAC
CTGAGCAGACGGTCTAGCAGCACCATGAGCAAGAGCGAGTACATGGAAATCGAAGAGGACATGAAC
AACTCTATCGCCCACTACCGCCAAGTGAACATCCGGACCGCCAACTGCACCACCGCCAACCAGAAC
TGCGTGAACAAGAGCAAGCTGCTGACCGATGTCTGA
wherein n is T or C Amino acid sequence of an edited human Kv1.1 comprising a valine at
position 400 (underlined) (SEQ ID NO: 2)
MTVMSGENVDEASAAPGHPQDGSYPRQADHDDHECCERVVINISGLRFETQLKTLAQFPNTLLGNP
KKRMRYFDPLRNEYFFDRNRPSFDAILYYYQSGGRLRRPVNVPLDMFSEEIKFYELGEEAMEKFRE
DEGFIKEEERPLPEKEYQRQVWLLFEYPESSGPARVIAIVSVMVILISIVIFCLETLPELKDDKDF
TGTVHRIDNTTVIYNSNIFTDPFFIVETLCIIWFSFELVVRFFACPSKTDFFKNIMNFIDIVAIIP
YFITLGTEIAEQEGNQKGEQATSLAILRVIRLVRVFRIFKLSRHSKGLQILGQTLKASMRELGLLI
FFLFIGVILFSSAVYFAEAEEAESHFSSIPDAFWWAVVSMTTVGYGDMYPVTIGGKIVGSLCAIAG
VLTVALPVPVIVSNFNYFYHRETEGEEQAQLLHVSSPNLASDSDLSRRSSSTMSKSEYMEIEEDMN
NSIAHYRQVNIRTANCTTANQNCVNKSKLLTDV Nucleotide sequence of an exemplary human CAMK2A promoter (SEQ ID
NO: 3)
TAAATAAATAAATAAATAATATAAATAATAAATGTCCAGGAATCAGAGCTCAAACTCAGATCCTTA
GTCTTAAACTCCAGTCCCTTTTCTTCCTAACTCCAAGACCTTGGAGTAAGATCTTGTGGCTGTAGG
TATGCTGATGCCCTGAAGAGTTGAAGTTGGCAGGGAAGGTGCCCAGAAAATTTTGGATTGAAGAT
TTCATGGCAAGTCTCTGGCCAGTGGCCTAGCCCGGGTAAGCCATGCTATGCTCACCTCCCCACAGC
CCCCTCTCGCCTTTTTTTTTTTTTTTTTTACCTTGACTGGAAGCACAAGCAGAAACTGGGACATG
AGCACCAGGAGACCAGATTTCCATGGTCCCGTTGGGGGCATGGGGTTGGGGAGAGGTTGCAGAGGA
```

-continued

Sequence Annex

GGGCTCTGGAGGGGAGCAACTGTCACAGCTGTGAGAGGTGGGGGTGAGCAGGCAGTCAGGGCTGTT
CCCTCCAGAATCCTGGGGTGTCCTCTGCACTTCTGCGCCAAGCTGGAGTGCTAGTGTGATGGACAA
GGTGGTAAGAGAGCTGAAAGAGCACGAGCATAACAAGAAAGACAGAGGCAGAAGCAAAAAAAAAAA
AAAAAAAAAACAGAGGGCAACAGAGAGACAGTTACAGAGACTACAGTGATCCACAGAGGGAGAGCC
ATCCCTGTGAATTAGCCATCATTTCCCTGTAAACCTTAGAACCCAGCTGTTGCCAGGGCAACGGGG
CAATACCTGTCTCTCTAGAGATGAAGTTGCCAGGGTAACTGCATCCTGTCATTCGTTCCTGGGGAC
CATCCGGAATGCGGCACCCACTGGCTGTTACCATGGCAACTGCCTTTTTGCCCCACTTAATCCCAT
CCCGTCTGCTACAAGGGCCCCACAGTTGGAGGTGGGGGAGGTGGGAAGAGAAAAGATCACTTGTGG
ACAAAGTTTGCTCTATTCCACCTCCTCCAGGCCCTCCTTGGGTCCATCACCCCAGGGGTGCTGGGT
CCATCCCACCCCCAGGCCCACACAGGCTTGCAGTATTGTGTGCGGTATGGTCAGGGCGTCCGAGAG
CAGGTTTCGCAGTGGAAGGCAGGCAGGTGTTGGGGAGGCAGTTACCGGGGCAACGGGAACAGGGCG
TTTTGGAGGTGGTTGCCATGGGGACCTGGATGCTGACGAAGGCTCGCGAGGCTGTGAGCAGCCACA
GTGCCCTGCTCAGAAGCCCCGGGCTCGTCAGTCAAACCGGTTCTCTGTTTGCACTCGGCAGCACGG
GCAGGCAAGTGGTCCCTAGGTTCGGGAGCAGAGCAGCAGCGCC

Nucleotide sequence of wild-type KCNA1 coding sequence, comprising an adenine at nucleotide position 1998 (underlined) (SEQ ID NO: 4)
ATGACGGTGATGTCTGGGGAGAACGTGGACGAGGCTTCGGCCGCCCCGGGCCACCCCCAGGATGGC
AGCTACCCCCGGCAGGCCGACCACGACGACCACGAGTGCTGCGAGCGCGTGGTGATCAACATCTCC
GGGCTGCGCTTCGAGACGCAGCTCAAGACCCTGGCGCAGTTCCCCAACACGCTGCTGGGCAACCCT
AAGAAACGCATGCGCTACTTCGACCCCCTGAGGAACGAGTACTTCTTCGACCGCAACCGGCCCAGC
TTCGACGCCATCCTCTACTACTACCAGTCCGGCGGCCGCCTGCGGAGGCCGGTCAACGTGCCCCTG
GACATGTTCTCCGAGGAGATCAAGTTTTACGAGTTGGGCGAGGAGGCCATGGAGAAGTTCCGGGAG
GACGAGGGCTTCATCAAGGAGGAGGAGCGCCCTCTGCCCGAGAAGGAGTACCAGCGCCAGGTGTGG
CTGCTCTTCGAGTACCCCGAGAGCTCGGGGCCCGCCAGGGTCATCGCCATCGTCTCCGTCATGGTC
ATCCTCATCTCCATCGTCATCTTTTGCCTGGAGACGCTCCCCGAGCTGAAGGATGACAAGGACTTC
ACGGGCACCGTCCACCGCATCGACAACACCACGGTCATCTACAATTCCAACATCTTCACAGACCCC
TTCTTCATCGTGGAAACGCTGTGTATCATCTGGTTCTCCTTCGAGCTGGTGGTGCGCTTCTTCGCC
TGCCCCAGCAAGACGGACTTCTTCAAAAACATCATGAACTTCATAGACATTGTGGCCATCATTCCT
TATTTCATCACGCTGGGCACCGAGATAGCTGAGCAGGAAGGAAACCAGAAGGGCGAGCAGGCCACC
TCCCTGGCCATCCTCAGGGTCATCCGCTTGGTAAGGGTTTTTAGAATCTTCAAGCTCTCCCGCCAC
TCTAAGGGCCTCCAGATCCTGGGCCAGACCCTCAAAGCTAGTATGAGAGAGCTAGGGCTGCTCATC
TTTTTCCTCTTCATCGGGGTCATCCTGTTTTCTAGTGCAGTGTACTTTGCCGAGGCGGAAGAAGCT
GAGTCGCACTTCTCCAGTATCCCCGATGCTTTCTGGTGGGCGGTGGTGTCCATGACCACTGTAGGA
TACGGTGACATGTACCCTGTGACAATTGGAGGCAAGATCGTGGGCTCCTTGTGTGCCATCGCTGGT
GTGCTAACAATTGCCCTGCCCGTACCTGTCATTGTGTCCAATTTCAACTATTTCTACCACCGAGAA
ACTGAGGGGGAAGAGCAGGCTCAGTTGCTCCACGTCAGTTCCCCTAACTTAGCCTCTGACAGTGAC
CTCAGTCGCCGCAGTTCCTCTACTATGAGCAAGTCTGAGTACATGGAGATCGAAGAGGATATGAAT
AATAGCATAGCCCATTATAGACAGGTCAATATCAGAACTGCCAATTGCACCACTGCTAACCAAAAC
TGCGTTAATAAGAGCAAGCTACTGACCGATGTTTAA Amino acid sequence of wild-type human Kv1.1, comprising a isoleucine at position 400 (underlined) (SEQ ID NO: 5)
MTVMSGENVDEASAAPGHPQDGSYPRQADHDDHECCERVVINISGLRFETQLKTLAQFPNTLLGNP
KKRMRYFDPLRNEYFFDRNRPSFDAILYYYQSGGRLRRPVNVPLDMFSEEIKFYELGEEAMEKFRE
DEGFIKEEERPLPEKEYQRQVWLLFEYPESSGPARVIAIVSVMVILISIVIFCLETLPELKDDKDF
TGTVHRIDNTTVIYNSNIFTDPFFIVETLCIIWFSFELVVRFFACPSKTDFFKNIMNFIDIVAIIP
YFITLGTEIAEQEGNQKGEQATSLAILRVIRLVRVFRIFKLSRHSKGLQILGQTLKASMRELGLLI
FFLFIGVILFSSAVYFAEAEEAESHFSSIPDAFWWAVVSMTTVGYGDMYPVTIGGKIVGSLCAIAG
VLTIALPVPVIVSNFNYFYHRETEGEEQAQLLHVSSPNLASDSDLSRRSSSTMSKSEYMEIEEDMN
NSIAHYRQVNIRTANCTTANQNCVNKSKLLTDV Nucleotide sequence of an exemplary engineered KCNA1 gene viral vector lacking a reporter (without bacterial plasmid portion) (SEQ ID NO: 9)
GACATTGATTATTGACTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAAT
GGGTGGAGTATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGACG
TCAATGGGAGTTTGTTTTGGCACCAAAATCAACGGGACTTTCCAAAATGTCGTAACAACTCCGCCC
CATTGACGCAAATGGGCGGTAGGCGTGTACGGTGGGAGGTCTATATAAGCAGAGCTCGTTTAGTGA
ACCGGGGTCTCTCTGGTTAGACCAGATCTGAGCCTGGGAGCTCTCTGGCTAACTAGGGAACCCACT
GCTTAAGCCTCAATAAAGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTAGCAGTGGCGCCCGAAC
AGGGACTTGAAAGCGAAAGGGAAACCAGAGGAGCTCTCTCGACGCAGGACTCGGCTTGCTGAAGCG
CGCACGGCAAGAGGCGAGGGGCGGCGACTGGTGAGTACGCCAAAAATTTTGACTAGCGGAGGCTAG
AAGGAGAGAGATGGGTGCGAGAGCGTCAGTATTAAGCGGGGGAGAATTAGATCGCGATGGGAAAAA
ATTCGGTTAAGGCCAGGGGGAAAGAAAAAATATAAATTAAAACATATAGTATGGGCAAGCAGGGAG
CTAGAACGATTCGCAGTTAATCCTGGCCTGTTAGAAACATCAGAAGGCTGTAGACAAATACTGGGA
CAGCTACAACCATCCCTTCAGACAGGATCAGAAGAACTTAGATCATTATATAATACAGTAGCAACC
CTCTATTGTGTGCATCAAAGGATAGAGATAAAAGACACCAAGGAAGCTTTAGACAAGATAGAGGAA
GAGCAAAACAAAAGTAAGACCACCGCACAGCAAGCGGCCGCTGATCTTCAGACCTGGAGGAGGAGA
TATGAGGGACAATTGGAGAAGTGAATTATATAAATATAAAGTAGTAAAAATTGAACCATTAGGAGT
AGCACCCACCAAGGCAAAGAGAAGAGTGGTGCAGAGAGAAAAAAGAGCAGTGGGAATAGGAGCTTT
GTTCCTTGGGTTCTTGGGAGCAGCAGGAAGCACTATGGGCGCAGCGTCAATGACGCTGACGGTACA

Sequence Annex

```
GGCCAGACAATTATTGTCTGGTATAGTGCAGCAGCAGAACAATTTGCTGAGGGCTATTGAGGCGCA
ACAGCATCTGTTGCAACTCACAGTCTGGGCATCAAGCAGCTCCAGGCAAGAATCCTGGCTGTGGA
AAGATACCTAAAGGATCAACAGCTCCTGGGGATTTGGGGTTGCTCTGGAAAACTCATTTGCACCAC
TGCTGTGCCTTGGAATGCTAGTTGGAGTAATAAATCTCTGGAACAGATTTGGAATCACACGACCTG
GATGGAGTGGGACAGAGAAATTAACAATTACACAAGCTTAATACACTCCTTAATTGAAGAATCGCA
AAACCAGCAAGAAAGAATGAACAAGAATTATTGGAATTAGATAAATGGGCAAGTTTGTGGAATTG
GTTTAACATAACAAATTGGCTGTGGTATATAAAATTATTCATAATGATAGTAGGAGGCTTGGTAGG
TTTAAGAATAGTTTTTGCTGTACTTTCTATAGTGAATAGAGTTAGGCAGGGATATTCACCATTATC
GTTTCAGACCCACCTCCCAACCCCGAGGGGACCCGACAGGCCCGAAGGAATAGAAGAAGAAGGTGG
AGAGAGAGACAGAGACAGATCCATTCGATTAGTGAACGGATCTCGACGGTATCGGTTAACTTTTAA
AAGAAAAGGGGGGATTGGGGGGTACAGTGCAGGGGAAAGAATAGTAGACATAATAGCAACAGCAT
ACAAACTAAAGAATTACAAAAACAAATTACAAAATTCAAAATTTTATCGAATTCCACGGGGTTAAT
CGAATAAATAAATAAATAAATAATATAAATAATAAATGTCCAGGAATCAGAGCTCAAACTCAGATC
CTTAGTCTTAAACTCCAGTCCCTTTCTTCCTAACTCCAAGACCTTGGAGTAAGATCTTGTGGCTG
TAGGTATGGCTGATGCCCTGAAGAGTTGAAGTTGGCAGGGAAGGTGCCCAGAAAATTTTGGATTGA
AGATTTCATGGCAAGTCTCTGGCCAGTGGCCTAGCCCGGGTAAGCCATGCTATGCTCACCTCCCCA
CAGCCCCCTCTCGCCTTTTTTTTTTTTTTTTTTACCTTGACTGGAAGCACAAGCAGAAACTGGGA
CATGAGCACCAGGAGACCAGATTTCCATGGTCCCGTTGGGGGCATGGGGTTGGGGAGAGGTTGCAG
AGGAGGGCTCTGGAGGGGAGCAACTGTCACAGCTGTGAGAGGTGGGGGTGAGCAGGCAGTCAGGGC
TGTTCCCTCCAGAATCCTGGGGTGTCCTCTGCACTTCTGCGCCAAGCTGGAGTGCTAGTGTGATGG
ACAAGGTGGTAAGAGAGCTGAAAGAGCACGAGCATAACAAGAAAGACAGAGGCAGAAGCAAAAAAA
AAAAAAAAAAAAACAGAGGGCAACAGAGAGACAGTTACAGAGACTACAGTGATCCACAGAGGGAG
AGCCATCCTGTGAATTAGCCATCATTTCCCTGTAAACCTTAGAACCCAGCTGTTGCCAGGGCAAC
GGGGCAATACCTGTCTCTCTAGAGATGAAGTTGCCAGGGTAACTGCATCCTGTCATTCGTTCCTGG
GGACCATCCGGAATGCGGCACCCACTGGCTGTTACCATGGCAACTGCCTTTTTGCCCCACTTAATC
CCATCCCGTCTGCTACAAGGGCCCCACAGTTGGAGGTGGGGGAGGTGGGAAGAGAAAAGATCACTT
GTGGACAAAGTTTGCTCTATTCCACCTCCTCCAGGCCCTCCTTGGGTCCATCACCCCAGGGGTGCT
GGGTCCATCCCACCCCCAGGCCCACACAGGCTTGCAGTATTGTGTGCGGTATGGTCAGGGCGTCCG
AGAGCAGGTTTCGCAGTGGAAGGCAGGCAGGTGTTGGGGAGGCAGTTACCGGGGCAACGGGAACAG
GGCGTTTTGGAGGTGGTTGCCATGGGGACCTGGATGCTGACGAAGGCTCGCGAGGCTGTGAGCAGC
CACAGTGCCCTGCTCAGAAGCCCCGGGCTCGTCAGTCAAACCGGTTCTCTGTTTGCACTCGGCAGC
ACGGGCAGGCAAGTGGTCCCTAGGTTCGGGAGCAGAGCAGCAGCGCCGGATCCGCCACCATGACCG
TGATGAGCGGCGAGAACGTGGACGAGGCCTCTGCCGCTCCTGGACACCCTCAGGATGGCAGCTATC
CCAGACAGGCCGACCACGACGATCACGAGTGCTGCGAGCGGGTCGTGATCAACATCAGCGGCCTGA
GATTCGAGACACAGCTGAAAACCCTGGCCCAGTTCCCCAACACCCTGCTGGGCAACCCCAAGAAAC
GGATGCGGTACTTCGACCCCCTGCGGAACGAGTACTTCTTCGACCGGAACCGGCCCAGCTTCGACG
CCATCCTGTACTACTACCAGAGCGGCGGCAGACTGCGGAGGCCCGTGAATGTGCCCCTGGACATGT
TCAGCGAGGAAATCAAGTTCTACGAGCTGGGCGAGGAAGCCATGGAAAAGTTCAGAGAGGACGAGG
GCTTCATCAAAGAGGAAGAGAGGCCCCTGCCCGAGAAAGAATACCAGAGACAAGTGTGGCTGCTGT
TCGAGTACCCCGAGTCTAGCGGCCCTGCCAGAGTGATCGCCATCGTGTCCGTGATGGTCATCCTGA
TCTCTATCGTGATCTTCTGCCTGGAAACCCTGCCTGAGCTGAAGGACGACAAGGACTTCACCGGCA
CCGTGCACCGGATCGACAACACCACCGTGATCTACAACAGCAATATCTTCACCGACCCATTCTTCA
TCGTGGAAACACTGTGCATCATCTGGTTCAGCTTCGAGCTGGTCGTGCGGTTCTTCGCCTGCCCCA
GCAAGACCGACTTCTTCAAGAACATCATGAACTTCATTGATATCGTGGCCATCATCCCCTACTTCA
TCACCCTGGGCACCGAGATCGCCGAGCAGGAAGGCAATCAGAAGGGCGAGCAGGCCACCAGCCTGG
CCATTCTGAGAGTGATCAGACTCGTGCGGGTGTTCCGGATCTTCAAGCTGAGCCGGCACAGCAAGG
GCCTGCAGATCCTGGGCCAGACACTGAAGGCCAGCATGAGAGAGCTGGGCCTGCTGATCTTCTTTC
TGTTCATCGGCGTGATCCTGTTCAGCAGCGCCGTGTACTTCGCCGAGGCCGAAGAAGCCGAGAGCC
ACTTCAGCTCTATCCCCGACGCCTTTTGGTGGGCCGTGGTGTCCATGACCACAGTGGGCTACGGCG
ACATGTAnCCCGTGACAATCGGCGGCAAGATCGTGGGCAGCCTGTGTGCCATTGCCGGCGTGCTGA
CAGTCGCCCTGCCTGTGCCTGTGATCGTGTCCAACTTCAACTACTTCTACCACCGGGAAACCGAGG
GGGAGGAACAGGCTCAGCTGCTGCACGTGTCCAGCCCCAATCTGGCCAGCGACAGCGACCTGAGCA
GACGGTCTAGCAGCACCATGAGCAAGAGCGAGTACATGGAAATCGAAGAGGACATGAACAACTCTA
TCGCCCACTACCGCCAAGTGAACATCCGGACCGCCAACTGCACCACCGCCAACCAGAACTGCGTGA
ACAAGAGCAAGCTGCTGACCGATGTCTGAGTCGACAATCAACCTCTGGATTACAAAATTTGTGAAA
GATTGACTGGTATTCTTAACTATGTTGCTCCTTTTACGCTATGTGGATACGCTGCTTTAATGCCTT
TGTATCATGCTATTGCTTCCCGTATGCTTTCATTTTCTCCTCCTTGTATAAATCCTGGTTGCTGT
CTCTTTATGAGGAGTTGTGGCCCGTTGTCAGGCAACGTGGCTGGTGTGCACTGTGTTTGCTGACG
CAACCCCCACTGGTTGGGGCATTGCCACCACCTGTCAGCTCCTTTCCGGGACTTTCGCTTTCCCC
TCCCTATTGCCACGGCGGAACTCATCGCCGCCTGCCTTGCCCGCTGCTGGACAGGGGCTCGGCTGT
TGGGCACTGACAATTCCGTGGTGTTGTCGGGGAAATCATCGTCCTTTCCTTGGCTGCTCGCCTGTG
TTGCCACCTGGATTCTGCGCGGGACGTCCTTCTGCTACGTCCCTTCGGCCCTCAATCCAGCGGACC
TTCCTTCCCGCGGCCTGCTGCCGGCTCTGCGGCCTCTTCCGCGTCTTCGCCTTCGCCCTCAGACGA
GTCGGATCTCCCTTTGGGCCGCCTCCCCGCCTGGAATTCGAGCTCGGTACCTTTAAGACCAATGAC
TTACAAGGCAGCTGTAGATCTTAGCCACTTTTTAAAAGAAAAGGGGGGACTGGAAGGGCTAATTCA
CTCCCAACGAAGACAAGATCTGCTTTTTGCTTGTACTGGGTCTCTCTGGTTAGACCAGATCTGAGC
CTGGGAGCTCTCTGGCTAACTAGGGAACCCACTGCTTAAGCCTCAATAAAGCTTGCCTTGAGTGCT
TCAAGTAGTGTGTGCCCGTCTGTTGTGTGACTCTGGTAACTAGAGATCCCTCAGACCCTTTTAGTC
AGTGTGGAAAATCTCTAGCA
```
wherein n is T or C Amino acid sequence of an edited human Kv1.1 comprising a valine at
position 400 (under Sequence Annex TGTVHRIDNTTVIYNSNIFTDPFFIVETLCIIWFSFELVVRFFACPSKTDFFKNIMNFIDIVAIIP
YFITLGTEIAEQEGNQKGEQATSLAILRVIRLVRVFRIFKLSRHSKGLQILGQTLKASMRELGLLI
FFLFIGVILFSSAVYFAEAEEAESHFSSIPDAFWWAVVSMTTVGYGDMVPVTIGGKIVGSLCAIAG
VLTVALPVPVIVSNFNYFYHRETEGEEQAQLLHVSSPNLASDSDLSRRSSSTMSKSEYMEIEEDMN
NSIAHYRQVNIRTANCTTANQNCVNKSKLLTDV

The invention claimed is:

1. An expression vector comprising an engineered KCNA1 gene encoding an edited Kv1.1 potassium channel operably linked to a promoter suitable to drive expression of the edited Kv1.1 potassium channel in human cells,
wherein the engineered KCNA1 gene has a nucleotide sequence comprising or consisting of the nucleotide sequence of SEQ ID NO: 1.

2. The expression vector of claim 1, wherein the promoter is a cell type specific promoter, which is optionally a promoter specific for neurons.

3. The expression vector of claim 2, wherein the cell type specific promoter is specific for pyramidal neurons.

4. The expression vector of claim 2, wherein the cell type specific promoter comprises a human CAMK2A promoter.

5. The expression vector of claim 4, wherein the human CAMK2A promoter has a nucleotide sequence comprising or consisting of the nucleotide sequence of SEQ ID NO: 3.

6. The expression vector of claim 1, wherein the vector is a viral vector.

7. The expression vector of claim 6, wherein the viral vector is a lentiviral vector, optionally wherein the lentiviral vector is a non-integrating lentiviral vector.

8. An in vitro method of making viral particles comprising transducing mammalian cells with the lentiviral vector according to claim 7 and expressing viral packaging and envelope proteins necessary for particle formation in the cells; and
culturing the transduced cells in a culture medium, such that the cells produce lentiviral particles that are released into the medium.

9. The in vitro method of claim 8, wherein the method comprises transducing the mammalian cells with one or more viral packaging and envelope expression vectors that encode the viral packaging and envelope proteins necessary for particle formation.

10. The in vitro method of claim 8, wherein the packaging proteins include a non-functional integrase enzyme such that the lentiviral vector is unable to incorporate its viral genome into the genome of the cells.

11. The in vitro method of claim 8, further comprising separating the viral particles from the culture medium and optionally concentrating the viral particles.

12. A viral particle derived from the lentiviral vector of claim 7.

13. A method of treatment of a neurological disorder associated with neuronal hyperexcitability comprising administering to an individual with the neurological disorder the viral particle of claim 12.

14. The method of treatment of claim 13, wherein the neurological disorder is a seizure disorder.

15. The method of treatment according to claim 14, wherein the seizure disorder is epilepsy, which is optionally neocortical epilepsy.

16. The method of treatment of claim 13, wherein the neurological disorder is Parkinson's disease or chronic pain.

17. An in vitro or ex vivo method of confirming the presence of engineered KCNA1 mRNA in a cell that has been obtained from a subject administered the viral particle of claim 12, the method comprising:
detecting the presence of engineered KCNA1 mRNA in the cell using a hybridisation assay.

18. A kit comprising the expression vector of claim 7 and a viral packaging and envelope expression vector that encodes viral packaging and envelope proteins necessary for particle formation when expressed in a cell, wherein the viral packaging expression vector is optionally an integrase-deficient viral packaging expression vector.

19. A method of confirming the presence of engineered KCNA1 mRNA in a cell, the method comprising:
transducing a cell with the expression vector of claim 1 under conditions that permit expression of engineered KCNA1 mRNA; and
detecting the presence of the engineered KCNA1 mRNA in the cell using a hybridisation assay.

20. A cell comprising the expression vector of claim 1, wherein the cell is optionally a mammalian cell, which is optionally a human cell, which is optionally a human embryonic kidney cell.

21. An expression vector, which is a lentiviral vector, comprising an engineered KCNA1 gene encoding an edited Kv1.1 potassium channel operably linked to a promoter suitable to drive expression of the edited Kv1.1 potassium channel in human cells, wherein the edited Kv1.1 potassium channel has an amino acid sequence comprising or consisting of the amino acid sequence of SEQ ID NO: 2, and wherein the lentiviral vector comprises a nucleotide sequence having at least 95% identity to the nucleotide sequence of SEQ ID NO: 9.

22. The expression vector of claim 21, wherein the promoter is a cell type specific promoter, wherein the promoter is specific for neurons.

23. The expression vector of claim 22, wherein the cell type specific promoter is specific for pyramidal neurons.

24. The expression vector of claim 22, wherein the cell type specific promoter comprises a human CAMK2A promoter, wherein the human CAMK2A promoter has a nucleotide sequence comprising or consisting of the nucleotide sequence of SEQ ID NO: 3.

25. A nucleic acid comprising an engineered KCNA1 gene encoding an edited Kv1.1 potassium channel, wherein the engineered KCNA1 gene has a nucleotide sequence comprising or consisting of the nucleotide sequence of SEQ ID NO: 1.

* * * * *

SEQUENCE LISTING

<160> NUMBER OF SEQ ID NOS: 14

<210> SEQ ID NO 1
<211> LENGTH: 1488
<212> TYPE: DNA
<213> ORGANISM: Artificial Sequence
<220> FEATURE:
<223> OTHER INFORMATION: Human KCNA1 gene
<220> FEATURE:
<221> NAME/KEY: misc_feature
<222> LOCATION: (1137)..(1137)
<223> OTHER INFORMATION: N = T or C

<400> SEQUENCE: 1

```
atgaccgtga tgagcggcga gaacgtggac gaggcctctg ccgctcctgg acaccctcag      60
gatggcagct atcccagaca ggccgaccac gacgatcacg agtgctgcga gcgggtcgtg     120
atcaacatca gcggcctgag attcgagaca cagctgaaaa ccctggccca gttccccaac     180
accctgctgg caaccccaa gaacggatg cggtacttcg accccctgcg gaacgagtac       240
ttcttcgacc ggaaccggcc cagcttcgac gccatcctgt actactacca gagcggcggc     300
agactgcgga ggcccgtgaa tgtgcccctg acatgttca gcgaggaaat caagttctac      360
gagctgggcg aggaagccat ggaaaagttc agagaggacg agggcttcat caaagaggaa     420
gagaggcccc tgcccgagaa agaataccag agacaagtgt ggctgctgtt cgagtacccc     480
gagtctagcg gccctgccag agtgatcgcc atcgtgtccg tgatggtcat cctgatctct     540
atcgtgatct tctgcctgga aaccctgcct gagctgaagg acgacaagga cttcaccggc     600
accgtgcacc ggatcgacaa caccaccgtg atctacaaca gcaatatctt caccgaccca     660
ttcttcatcg tggaaacact gtgcatcatc tggttcagct tcgagctggt cgtgcggttc     720
ttcgcctgcc ccagcaagac cgacttcttc aagaacatca tgaacttcat tgatatcgtg     780
gccatcatcc cctacttcat cacccctgggc accgagatcg ccgagcagga aggcaatcag     840
aagggcgagc aggccaccag cctggccatt ctgagagtga tcagactcgt gcgggtgttc     900
cggatcttca gctgagccg gcacagcaag ggcctgcaga tcctgggcca gacactgaag     960
gccagcatga gagctgggg cctgctgatc ttctttctgt tcatcggcgt gatcctgttc    1020
agcagcgccg tgtacttcgc cgaggccgaa gaagccgaga gccacttcag ctctatcccc    1080
gacgcctttt ggtgggccgt ggtgtccatg accacagtgg gctacggcga catgtanccc    1140
gtgacaatcg gcggcaagat cgtgggcagc ctgtgtgcca ttgccggcgt gctgacagtc    1200
gccctgcctg tgcctgtgat cgtgtccaac ttcaactact ctaccaccg ggaaaccgag     1260 ggggaggaac aggctcagct gctgcacgtg tccagcccca atctggccag cgacagcgac    1320
ctgagcagac ggtctagcag caccatgagc aagagcgagt acatggaaat cgaagaggac    1380
atgaacaact ctatcgccca ctaccgccaa gtgaacatcc ggaccgccaa ctgcaccacc    1440
gccaaccaga actgcgtgaa caagagcaag ctgctgaccg atgtctga                1488
```

```
<210> SEQ ID NO 2
<211> LENGTH: 495
<212> TYPE: PRT
<213> ORGANISM: Artificial Sequence
<220> FEATURE:
<223> OTHER INFORMATION: edited human Kv1.1

<400> SEQUENCE: 2
```

| | | | | | | | | | | | | | | |
|---|---|---|---|---|---|---|---|---|---|---|---|---|---|---|
| Met | Thr | Val | Met | Ser | Gly | Glu | Asn | Val | Asp | Glu | Ala | Ser | Ala | Pro |
| 1 | | | | 5 | | | | | 10 | | | | | 15 |
| Gly | His | Pro | Gln | Asp | Gly | Ser | Tyr | Pro | Arg | Gln | Ala | Asp | His | Asp |
| | | | 20 | | | | | 25 | | | | | 30 | |
| His | Glu | Cys | Cys | Glu | Arg | Val | Val | Ile | Asn | Ile | Ser | Gly | Leu | Arg | Phe |
| | | 35 | | | | | 40 | | | | | 45 | | |
| Glu | Thr | Gln | Leu | Lys | Thr | Leu | Ala | Gln | Phe | Pro | Asn | Thr | Leu | Leu | Gly |
| | 50 | | | | | 55 | | | | | 60 | | | | |
| Asn | Pro | Lys | Lys | Arg | Met | Arg | Tyr | Phe | Asp | Pro | Leu | Arg | Asn | Glu | Tyr |
| 65 | | | | | 70 | | | | | 75 | | | | | 80 |
| Phe | Phe | Asp | Arg | Asn | Arg | Pro | Ser | Phe | Asp | Ala | Ile | Leu | Tyr | Tyr | Tyr |
| | | | | 85 | | | | | 90 | | | | | 95 | |
| Gln | Ser | Gly | Gly | Arg | Leu | Arg | Arg | Pro | Val | Asn | Val | Pro | Leu | Asp | Met |
| | | | 100 | | | | | 105 | | | | | 110 | | |
| Phe | Ser | Glu | Glu | Ile | Lys | Phe | Tyr | Glu | Leu | Gly | Glu | Glu | Ala | Met | Glu |
| | | 115 | | | | | 120 | | | | | 125 | | | |
| Lys | Phe | Arg | Glu | Asp | Glu | Gly | Phe | Ile | Lys | Glu | Glu | Arg | Pro | Leu |
| 130 | | | | | 135 | | | | | 140 | | | | | |
| Pro | Glu | Lys | Glu | Tyr | Gln | Arg | Gln | Val | Trp | Leu | Leu | Phe | Glu | Tyr | Pro |
| 145 | | | | | 150 | | | | | 155 | | | | | 160 |
| Glu | Ser | Ser | Gly | Pro | Ala | Arg | Val | Ile | Ala | Ile | Val | Ser | Val | Met | Val |
| | | | | 165 | | | | | 170 | | | | | 175 | |
| Ile | Leu | Ile | Ser | Ile | Val | Ile | Phe | Cys | Leu | Glu | Thr | Leu | Pro | Glu | Leu |
| | | | 180 | | | | | 185 | | | | | 190 | | |
| Lys | Asp | Asp | Lys | Asp | Phe | Thr | Gly | Thr | Val | His | Arg | Ile | Asp | Asn | Thr |
| | | 195 | | | | | 200 | | | | | 205 | | | |
| Thr | Val | Ile | Tyr | Asn | Ser | Asn | Ile | Phe | Thr | Asp | Pro | Phe | Phe | Ile | Val |
| | 210 | | | | | 215 | | | | | 220 | | | | |
| Glu | Thr | Leu | Cys | Ile | Ile | Trp | Phe | Ser | Phe | Glu | Leu | Val | Val | Arg | Phe |
| 225 | | | | | 230 | | | | | 235 | | | | | 240 |
| Phe | Ala | Cys | Pro | Ser | Lys | Thr | Asp | Phe | Phe | Lys | Asn | Ile | Met | Asn | Phe |
| | | | | 245 | | | | | 250 | | | | | 255 | |
| Ile | Asp | Ile | Val | Ala | Ile | Ile | Pro | Tyr | Phe | Ile | Thr | Leu | Gly | Thr | Glu |
| | | | 260 | | | | | 265 | | | | | 270 | | |
| Ile | Ala | Glu | Gln | Glu | Gly | Asn | Gln | Lys | Gly | Glu | Gln | Ala | Thr | Ser | Leu |
| | | 275 | | | | | 280 | | | | | 285 | | | |
| Ala | Ile | Leu | Arg | Val | Ile | Arg | Leu | Val | Arg | Val | Phe | Arg | Ile | Phe | Lys |
| | 290 | | | | | 295 | | | | | 300 | | | | |
| Leu | Ser | Arg | His | Ser | Lys | Gly | Leu | Gln | Ile | Leu | Gly | Gln | Thr | Leu | Lys |
| 305 | | | | | 310 | | | | | 315 | | | | | 320 |
| Ala | Ser | Met | Arg | Glu | Leu | Gly | Leu | Leu | Ile | Phe | Phe | Leu | Phe | Ile | Gly |
| | | | | 325 | | | | | 330 | | | | | 335 | |
| Val | Ile | Leu | Phe | Ser | Ser | Ala | Val | Tyr | Phe | Ala | Glu | Ala | Glu | Glu | Ala |
| | | | 340 | | | | | 345 | | | | | 350 | | |
| Glu | Ser | His | Phe | Ser | Ser | Ile | Pro | Asp | Ala | Phe | Trp | Trp | Ala | Val | Val |
| | | 355 | | | | | 360 | | | | | 365 | | | |

```
Ser Met Thr Thr Val Gly Tyr Gly Asp Met Tyr Pro Val Thr Ile Gly
    370                 375                 380

Gly Lys Ile Val Gly Ser Leu Cys Ala Ile Ala Gly Val Leu Thr Val
385                 390                 395                 400

Ala Leu Pro Val Pro Val Ile Val Ser Asn Phe Asn Tyr Phe Tyr His
                405                 410                 415

Arg Glu Thr Glu Gly Glu Gln Ala Gln Leu Leu His Val Ser Ser
                420                 425                 430

Pro Asn Leu Ala Ser Asp Ser Asp Leu Ser Arg Arg Ser Ser Ser Thr
            435                 440                 445

Met Ser Lys Ser Glu Tyr Met Glu Ile Glu Glu Asp Met Asn Asn Ser
    450                 455                 460

Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
                485                 490                 495

<210> SEQ ID NO 3
<211> LENGTH: 1297
<212> TYPE: DNA
<213> ORGANISM: Homo sapiens

<400> SEQUENCE: 3
taaataaata aataaataat ataaataata aatgtccagg aatcagagct caaactcaga      60
tccttagtct taaactccag tcccttttct tcctaactcc aagaccttgg agtaagatct    120
tgtggctgta ggtatggctg atgccctgaa gagttgaagt tggcagggaa ggtgcccaga    180
aaattttgga ttgaagattt catggcaagt ctctggccag tggcctagcc cgggtaagcc    240
atgctatgct cacctcccca cagccccctc tcgccttttt ttttttttt ttttaccttg    300 actggaagca caagcagaaa ctgggacatg agcaccagga gaccagattt ccatggtccc    360 gttggggca tggggttggg gagaggttgc agaggagggc tctggagggg agcaactgtc    420
acagctgtga gaggtggggg tgagcaggca gtcaggctg ttccctccag aatcctgggg    480
tgtcctctgc acttctgcgc caagctggag tgctagtgtg atggacaagg tggtaagaga    540
gctgaaagag cacgagcata caagaaaga cagaggcaga agcaaaaaaa aaaaaaaaa    600 aaaacagagg gcaacagaga gacagttaca gagactacag tgatccacag agggagagcc    660
atccctgtga attagccatc atttccctgt aaaccttaga acccagctgt tgccagggca    720
acggggcaat acctgtctct ctagagatga agttgccagg gtaactgcat cctgtcattc    780
gttcctgggg accatccgga atgcggcacc cactggctgt taccatggca actgccttt    840 tgccccactt aatcccatcc cgtctgctac aagggcccca cagttggagg tgggggaggt    900
gggaagagaa aagatcactt gtggacaaag tttgctctat tccacctcct ccaggccctc    960
cttgggtcca tcaccccagg ggtgctgggt ccatcccacc cccaggccca cacaggcttg   1020
cagtattgtg tgcggtatgg tcagggcgtc cgagagcagg tttcgcagtg gaaggcaggc   1080
aggtgttggg gaggcagtta ccggggcaac gggaacaggg cgttttggag gtggttgcca   1140 tgggacctg gatgctgacg aaggctcgcg aggctgtgag cagccacagt gccctgctca   1200 gaagcccgg gctcgtcagt caaaccggtt ctctgtttgc actcggcagc acgggcaggc   1260
aagtggtccc taggttcggg agcagagcag cagcgcc                             1297

<210> SEQ ID NO 4
<211> LENGTH: 1488
```

<212> TYPE: DNA
<213> ORGANISM: Artificial Sequence
<220> FEATURE:
<223> OTHER INFORMATION: wild-type KCNA1 coding sequence

<400> SEQUENCE: 4

```
atgacggtga tgtctgggga gaacgtggac gaggcttcgg ccgccccggg ccaccccag      60
gatggcagct accccccggca ggccgaccac gacgaccacg agtgctgcga gcgcgtggtg    120
atcaacatct ccgggctgcg cttcgagacg cagctcaaga ccctggcgca gttccccaac    180
acgctgctgg gcaaccctaa gaaacgcatg cgctacttcg accccctgag gaacgagtac    240
ttcttcgacc gcaaccggcc cagcttcgac gccatcctct actactacca gtccggcggc    300
cgcctgcgga ggccggtcaa cgtgccctg gacatgttcc tccgaggagat caagttttac    360
gagttgggcg aggaggccat ggagaagttc cgggaggacg agggcttcat caaggaggag    420
gagcgccctc tgcccgagaa ggagtaccag cgccaggtgt ggctgctctt cgagtacccc    480
gagagctcgg gcccgccag gtcatcgcc atcgtctccg tcatggtcat cctcatctcc    540
atcgtcatct tttgcctgga gacgctcccc gagctgaagg atgacaagga cttcacgggc    600
accgtccacc gcatcgacaa caccacggtc atctacaatt ccaacatctt cacagacccc    660
ttcttcatcg tggaaacgct gtgtatcatc tggttctcct tcgagctggt ggtgcgcttc    720
ttcgcctgcc ccagcaagac ggacttcttc aaaaacatca tgaacttcat agacattgtg    780
gccatcattc cttatttcat cacgctgggc accgagatag ctgagcagga aggaaaccag    840
aagggcgagc aggccaccct cctggccatc ctcagggtca tccgcttggt aaggggttttt    900
agaatcttca agctctcccg ccactctaag ggcctccaga tcctgggcca gaccctcaaa    960
gctagtatga gagagctagg gctgctcatc ttttttcctct tcatcggggt catcctgttt   1020
tctagtgcag tgtactttgc cgaggcggaa gaagctgagt cgcacttctc cagtatcccc   1080
gatgctttct ggtgggcggt ggtgtccatg accactgtag gatacggtga catgtaccct   1140
gtgacaattg gaggcaagat cgtgggctcc ttgtgtgcca tcgctggtgt gctaacaatt   1200
gccctgccg tacctgtcat tgtgtccaat ttcaactatt tctaccaccg agaaactgag   1260
ggggaagagc aggctcagtt gctccacgtc agttcccctta acttagcctc tgacagtgac   1320
ctcagtcgcc gcagttcctc tactatgagc aagtctgagt acatggagat cgaagaggat   1380
atgaataata gcatagccca ttatagacag gtcaatatca gaactgccaa ttgcaccact   1440
gctaaccaaa actgcgttaa taagagcaag ctactgaccg atgtttaa                1488
```

<210> SEQ ID NO 5
<211> LENGTH: 495
<212> TYPE: PRT
<213> ORGANISM: Artificial Sequence
<220> FEATURE:
<223> OTHER INFORMATION: wild-type human Kv1.1

<400> SEQUENCE: 5

```
Met Thr Val Met Ser Gly Glu Asn Val Asp Glu Ala Ser Ala Ala Pro
1               5                   10                  15

Gly His Pro Gln Asp Gly Ser Tyr Pro Arg Gln Ala Asp His Asp Asp
            20                  25                  30

His Glu Cys Cys Glu Arg Val Val Ile Asn Ile Ser Gly Leu Arg Phe
        35                  40                  45

Glu Thr Gln Leu Lys Thr Leu Ala Gln Phe Pro Asn Thr Leu Leu Gly
    50                  55                  60
```

```
Asn Pro Lys Lys Arg Met Arg Tyr Phe Asp Pro Leu Arg Asn Glu Tyr
 65                  70                  75                  80

Phe Phe Asp Arg Asn Arg Pro Ser Phe Asp Ala Ile Leu Tyr Tyr Tyr
                 85                  90                  95

Gln Ser Gly Gly Arg Leu Arg Arg Pro Val Asn Val Pro Leu Asp Met
            100                 105                 110

Phe Ser Glu Glu Ile Lys Phe Tyr Glu Leu Gly Glu Ala Met Glu
        115                 120                 125

Lys Phe Arg Glu Asp Glu Gly Phe Ile Lys Glu Glu Arg Pro Leu
    130                 135                 140

Pro Glu Lys Glu Tyr Gln Arg Gln Val Trp Leu Leu Phe Glu Tyr Pro
145                 150                 155                 160

Glu Ser Ser Gly Pro Ala Arg Val Ile Ala Ile Val Ser Val Met Val
                165                 170                 175

Ile Leu Ile Ser Ile Val Ile Phe Cys Leu Glu Thr Leu Pro Glu Leu
                180                 185                 190

Lys Asp Asp Lys Asp Phe Thr Gly Thr Val His Arg Ile Asp Asn Thr
                195                 200                 205

Thr Val Ile Tyr Asn Ser Asn Ile Phe Thr Asp Pro Phe Phe Ile Val
    210                 215                 220

Glu Thr Leu Cys Ile Ile Trp Phe Ser Phe Glu Leu Val Val Arg Phe
225                 230                 235                 240

Phe Ala Cys Pro Ser Lys Thr Asp Phe Phe Lys Asn Ile Met Asn Phe
                245                 250                 255

Ile Asp Ile Val Ala Ile Ile Pro Tyr Phe Ile Thr Leu Gly Thr Glu
                260                 265                 270

Ile Ala Glu Gln Glu Gly Asn Gln Lys Gly Glu Gln Ala Thr Ser Leu
            275                 280                 285

Ala Ile Leu Arg Val Ile Arg Leu Val Arg Val Phe Arg Ile Phe Lys
            290                 295                 300

Leu Ser Arg His Ser Lys Gly Leu Gln Ile Leu Gly Gln Thr Leu Lys
305                 310                 315                 320

Ala Ser Met Arg Glu Leu Gly Leu Leu Ile Phe Phe Leu Phe Ile Gly
                325                 330                 335

Val Ile Leu Phe Ser Ser Ala Val Tyr Phe Ala Glu Ala Glu Glu Ala
            340                 345                 350

Glu Ser His Phe Ser Ser Ile Pro Asp Ala Phe Trp Trp Ala Val Val
            355                 360                 365

Ser Met Thr Thr Val Gly Tyr Gly Asp Met Tyr Pro Val Thr Ile Gly
    370                 375                 380

Gly Lys Ile Val Gly Ser Leu Cys Ala Ile Ala Gly Val Leu Thr Ile
385                 390                 395                 400

Ala Leu Pro Val Pro Val Ile Val Ser Asn Phe Asn Tyr Phe Tyr His
                405                 410                 415

Arg Glu Thr Glu Gly Glu Glu Gln Ala Gln Leu Leu His Val Ser Ser
                420                 425                 430

Pro Asn Leu Ala Ser Asp Ser Asp Leu Ser Arg Arg Ser Ser Ser Thr
            435                 440                 445

Met Ser Lys Ser Glu Tyr Met Glu Ile Glu Glu Asp Met Asn Asn Ser
    450                 455                 460

Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
```

<210> SEQ ID NO 6
<211> LENGTH: 9010
<212> TYPE: DNA
<213> ORGANISM: Artificial Sequence
<220> FEATURE:
<223> OTHER INFORMATION: CMV-KCNA1 pilot transfer plasmid

<400> SEQUENCE: 6

| | | | | | |
|---|---|---|---|---|---|
| tgtagtctta | tgcaatactc | ttgtagtctt | gcaacatggt | aacgatgagt tagcaacatg | 60 |
| ccttacaagg | agagaaaaag | caccgtgcat | gccgattggt | ggaagtaagg tggtacgatc | 120 |
| gtgccttatt | aggaaggcaa | cagacgggtc | tgacatggat | tggacgaacc actgaattgc | 180 |
| cgcattgcag | agatattgta | tttaagtgcc | tagctcgata | caataaacgg gtctctctgg | 240 |
| ttagaccaga | tctgagcctg | ggagctctct | ggctaactag | gaacccact gcttaagcct | 300 |
| caataaagct | tgccttgagt | gcttcaagta | gtgtgtgccc | gtctgttgtg tgactctggt | 360 |
| aactagagat | ccctcagacc | cttttagtca | gtgtggaaaa | tctctagcag tggcgcccga | 420 |
| acagggacct | gaaagcgaaa | gggaaaccag | agctctctcg | acgcaggact cggcttgctg | 480 |
| aagcgcgcac | ggcaagaggc | gaggggcggc | gactggtgag | tacgccaaaa attttgacta | 540 |
| gcggaggcta | aaggagaga | gatgggtgcg | agagcgtcag | tattaagcgg gggagaatta | 600 |
| gatcgcgatg | ggaaaaaatt | cggttaaggc | caggggggaaa | gaaaaaatat aaattaaaac | 660 |
| atatagtatg | ggcaagcagg | gagctagaac | gattcgcagt | taatcctggc ctgttagaaa | 720 |
| catcagaagg | ctgtagacaa | atactgggac | agctacaacc | atcccttcag acaggatcag | 780 |
| aagaacttag | atcattatat | aatacagtag | caaccctcta | ttgtgtgcat caaaggatag | 840 |
| agataaaaga | caccaaggaa | gctttagaca | agatagagga | gagcaaaac aaaagtaaga | 900 |
| ccaccgcaca | gcaagcggcc | actgatcttc | agacctggag | gaggagatat gagggacaat | 960 |
| tggagaagtg | aattatataa | atataaagta | gtaaaaattg | aaccattagg agtagcaccc | 1020 |
| accaaggcaa | agagaagagt | ggtgcagaga | gaaaaagag | cagtgggaat aggagctttg | 1080 |
| ttccttgggt | tcttgggagc | agcaggaagc | actatgggcg | cagcctcaat gacgctgacg | 1140 |
| gtacaggcca | gacaattatt | gtctggtata | gtgcagcagc | agaacaattt gctgagggct | 1200 |
| attgaggcgc | aacagcatct | gttgcaactc | acagtctggg | gcatcaagca gctccaggca | 1260 |
| agaatcctgg | ctgtggaaag | atacctaaag | gatcaacagc | tcctggggat ttggggttgc | 1320 |
| tctggaaaac | tcatttgcac | cactgctgtg | ccttggaatg | ctagttggag taataaatct | 1380 |
| ctggaacaga | ttggaatcac | acgacctgga | tggagtggga | cagagaaatt aacaattaca | 1440 |
| caagcttaat | acactcctta | attgaagaat | cgcaaaacca | gcaagaaaag aatgaacaag | 1500 |
| aattattgga | attagataaa | tgggcaagtt | tgtggaattg | gtttaacata acaaattggc | 1560 |
| tgtggtatat | aaaattattc | ataatgatag | taggaggctt | ggtaggttta agaatagttt | 1620 |
| ttgctgtact | ttctatagtg | aatagagtta | ggcaggata | ttcaccatta tcgtttcaga | 1680 |
| cccacctccc | aaccccgagg | ggacccgaca | ggcccgaagg | aatagaagaa gaaggtggag | 1740 |
| agagagacag | agacagatcc | attcgattag | tgaacggatc | tcgacggtta acttttaaaa | 1800 |
| gaaaaggggg | gattgggggg | tacagtgcag | gggaaagaat | agtagacata atagcaacag | 1860 |
| acatacaaac | taagaatta | caaaaacaaa | ttacaaaaat | tcaaaatttt atcgatacta | 1920 |
| gtattatgcc | cagtacatga | ccttatggga | ctttcctact | ggcagtaca tctacgtatt | 1980 |
| agtcatcgct | attaccatgg | tgatgcggtt | ttggcagtac | atcaatgggc gtggatagcg | 2040 |

```
gtttgactca cggggatttc caagtctcca ccccattgac gtcaatggga gtttgttttg    2100
gcaccaaaat caacgggact ttccaaaatg tcgtaacaac tccgcCccat tgacgcaaat    2160
gggcggtagg cgtgtacggt gggaggtcta tataagcaga gctcgtttag tgaaccgtca    2220
gatcgcctgg agacgccatc cacgctgttt tgacctccat agaagattct agagctagca    2280
tgacggtgat gtctggggag aacgtggacg aggcttcggc cgccccgggc caccccCagg    2340
atggcagcta cccccggcag gccgaccacg acgaccacga tgctgcgag cgcgtggtga    2400
tcaacatctc cgggctgcgc ttcgagacgc agctcaagac cctggcgcag ttccccaaca    2460
cgctgctggg caaccctaag aaacgcatgc gctacttcga cccCctgagg aacgagtact    2520
tcttcgaccg caaccggccc agcttcgacg ccatcctcta ctactaccag tccggcggcc    2580
gcctgcggag gccggtcaac gtgccCctgg acatgttctc cgaggagatc aagttttacg    2640
agttgggcga ggaggccatg gagaagttcc gggaggacga gggcttcatc aaggaggagg    2700
agcgccctct gcccgagaag gagtaccagc gccaggtgtg gctgctcttc gagtaccccg    2760
agagctcggg gcccgccagg gtcatcgcca tcgtctccgt catggtcatc ctcatctcca    2820
tcgtcatctt ttgcctggag acgctccccg agctgaagga tgacaaggac ttcacgggca    2880
ccgtccaccg catcgacaac accacggtca tctacaattc caacatcttc acagacccct    2940
tcttcatcgt ggaaacgctg tgtatcatct ggttctcctt cgagctggtg gtgcgcttct    3000
tcgcctgccc cagcaagacg gacttcttca aaaacatcat gaacttcata gacattgtgg    3060
ccatcattcc ttatttcatc acgctgggca ccgagatagc tgagcaggaa ggaaaccaga    3120
agggcgagca ggccacctcc ctggccatcc tcagggtcat ccgcttggta agggttttta    3180
gaatcttcaa gctctcccgc cactctaagg gcctccagat cctgggccag accctcaaag    3240
ctagtatgag agagctaggg ctgctcatct ttttcctctt catcggggtc atcctgtttt    3300
ctagtgcagt gtactttgcc gaggcggaag aagctgagtc gcacttctcc agtatccccg    3360
atgctttctg gtgggcggtg gtgtccatga ccactgtagg atacggtgac atgtaccctg    3420
tgacaattgg aggcaagatc gtgggctcct tgtgtgccat cgctggtgtg ctaacaattg    3480
ccctgccCgt acctgtcatt gtgtccaatt tcaactattt ctaccaccga gaaactgagg    3540
gggaagagca ggctcagttg ctccacgtca gttcccctaa cttagcctct gacagtgacc    3600
tcagtcgccg cagttcctct actatgagca agtctgagta catggagatc gaagaggata    3660
tgaataatag catagcccat tatagacagg tcaatatcag aactgccaat tgcaccactg    3720
ctaaccaaaa ctgcgttaat aagagcaagc tactgaccga tgtttaagcg gccgcaagga    3780
tctgcgatcg ctccggtgcc cgtcagtggg cagagcgcac atcgcccaca gtccccgaga    3840
agttggggga aggggtcggc aattgaacgg gtgcctagaa aggtggcgc ggggtaaact    3900
gggaaagtga tgtcgtgtac tggctccgcc ttttttccga gggtggggga aaccgtata    3960
taagtgcagt agtcgccgtg aacgttcttt ttcgcaacgg gtttgccgcc agaacacagc    4020
tgaagcttcg aggggctcgc atctctcctt cacgcgcccg ccgccctacc tgaggccgcc    4080
atccacgccg gttgagtcgc gttctgccgc ctccCgcctg tggtgcctcc tgaactgcgt    4140
ccgccgtcta ggtaagttta agctcaggt cgagaccggg cctttgtccg gcgctccctt    4200
ggagcctacc tagactcagc cggctctcca cgctttgcct gaccctgctt gctcaactct    4260
acgtctttgt ttcgttttct gttctgcgcc gttacagatc caagctgtga ccggcgccta    4320
cgctagacgc caccatggag agcgacgaga gcggcctgcc cgcaatggag atcgagtgcc    4380
```

```
gcatcaccgg cacccctgaac ggcgtggagt tcgagctggt gggcggcgga gagggcaccc      4440
ccaagcaggg ccgcatgacc aacaagatga agagcaccaa aggcgccctg accttcagcc      4500
cctacctgct gagccacgtg atgggctacg gcttctacca cttcggcacc taccccagcg      4560
gctacgagaa ccccttcctg cacgccatca acaacggcgg ctacaccaac acccgcatcg      4620
agaagtacga ggacggcggc gtgctgcacg tgagcttcag ctaccgctac gaggccggcc      4680
gcgtgatcgg cgacttcaag gtggtgggca ccggcttccc cgaggacagc gtgatcttca      4740
ccgacaagat catccgcagc aacgccaccg tggagcacct gcaccccatg ggcgataacg      4800
tgctggtggg cagcttcgcc cgcaccttca gcctgcgcga cggcggctac tacagcttcg      4860
tggtggacag ccacatgcac ttcaagagcg ccatccaccc cagcatcctg cagaacgggg      4920
gccccatgtt cgccttccgc cgcgtggagg agctgcacag caacaccgag ctgggcatcg      4980
tggagtacca gcacgccttc aagaccccca tcgccttcgc cagatcccgc gctcagtcgt      5040
ccaattctgc cgtggacggc accgccggac ccggctccac cggatctcgc taagtcgaca      5100
atcaacctct ggattacaaa atttgtgaaa gattgactgg tattcttaac tatgttgctc      5160
cttttacgct atgtggatac gctgctttaa tgcctttgta tcatgctatt gcttcccgta      5220
tggctttcat tttctcctcc ttgtataaat cctggttgct gtctctttat gaggagttgt      5280
ggcccgttgt caggcaacgt ggcgtggtgt gcactgtgtt tgctgacgca accccactg      5340 gttgggcat tgccaccacc tgtcagctcc tttccgggac tttcgctttc cctccccta     5400 ttgccacggc ggaactcatc gccgcctgcc ttgcccgctg ctggacaggg gctcggctgt      5460
tgggcactga caattccgtg gtgttgtcgg ggaaatcatc gtcctttcct ggctgctcg      5520 cctgtgttgc cacctggatt ctgcgcggga cgtccttctg ctacgtccct tcggccctca      5580
atccagcgga ccttccttcc cgcggcctgc tgccggctct gcggcctctt ccgcgtcttc      5640
gccttcgccc tcagacgagt cggatctccc tttgggccgc ctccccgcct ggtacctta      5700 agaccaatga cttacaaggc agctgtagat cttagccact tttttaaaga aaagggggga      5760
ctggaagggc taattcactc ccaacgaaaa taagatctgc tttttgcttg tactgggtct      5820
ctctggttag accagatctg agcctgggag ctctctggct aactagggaa cccactgctt      5880
aagcctcaat aaagcttgcc ttgagtgctt caagtagtgt gtgcccgtct gttgtgtgac      5940
tctggtaact agagatccct cagacccttt tagtcagtgt ggaaaatctc tagcagtagt      6000
agttcatgtc atcttattat tcagtattta aacttgcaa agaaatgaat atcagagagt      6060
gagaggaact tgtttattgc agcttataat ggttacaaat aaagcaatag catcacaaat      6120
ttcacaaata aagcattttt ttcactgcat tctagttgtg gtttgtccaa actcatcaat      6180
gtatcttatc atgtctggct ctagctatcc cgccccctaac tccgcccagt tccgcccatt      6240
ctccgcccca tggctgacta attttttta tttatgcaga ggccgaggcc gcctcggcct      6300
ctgagctatt ccagaagtag tgaggaggct tttttggagg cctagacttt tgcagagacg      6360
gcccaaattc gtaatcatgg tcatagctgt ttcctgtgtg aaattgttat ccgctcacaa      6420
ttccacacaa catacgagcc ggaagcataa agtgtaaagc ctggggtgcc taatgagtga      6480
gctaactcac attaattgcg ttgcgctcac tgcccgcttt ccagtcggga aacctgtcgt      6540
gccagctgca ttaatgaatc ggccaacgcg cggggagagg cggtttgcgt attgggcgct      6600
cttccgcttc ctcgctcact gactcgctgc gctcggtcgt tcggctgcgg cgagcggtat      6660
cagctcactc aaaggcggta atacggttat ccacagaatc aggggataac gcaggaaaga      6720
acatgtgagc aaaaggccag caaaaggcca ggaaccgtaa aaaggccgcg ttgctggcgt      6780
```

```
ttttccatag gctccgcccc cctgacgagc atcacaaaaa tcgacgctca agtcagaggt    6840
ggcgaaaccc gacaggacta taagatacc aggcgtttcc ccctggaagc tccctcgtgc    6900
gctctcctgt tccgaccctg ccgcttaccg gatacctgtc cgcctttctc ccttcgggaa    6960
gcgtggcgct ttctcatagc tcacgctgta ggtatctcag ttcggtgtag gtcgttcgct    7020
ccaagctggg ctgtgtgcac gaaccccccg ttcagcccga ccgctgcgcc ttatccggta    7080
actatcgtct tgagtccaac ccggtaagac acgacttatc gccactggca gcagccactg    7140
gtaacaggat tagcagagcg aggtatgtag gcggtgctac agagttcttg aagtggtggc    7200
ctaactacgg ctacactaga aggacagtat ttggtatctg cgctctgctg aagccagtta    7260
ccttcggaaa aagagttggt agctcttgat ccggcaaaca accaccgct ggtagcggtg    7320 gtttttttgt ttgcaagcag cagattacgc gcagaaaaaa aggatctcaa gaagatcctt    7380
tgatcttttc tacggggtct gacgctcagt ggaacgaaaa ctcacgttaa gggattttgg    7440
tcatgagatt atcaaaaagg atcttcacct agatcctttt aaattaaaaa tgaagtttta    7500
aatcaatcta agtatatat gagtaaactt ggtctgacag ttaccaatgc ttaatcagtg    7560
aggcacctat ctcagcgatc tgtctatttc gttcatccat agttgcctga ctccccgtcg    7620
tgtagataac tacgatacgg gagggcttac catctggccc cagtgctgca atgataccgc    7680
gagacccacg ctcaccggct ccagatttat cagcaataaa ccagccagcc ggaagggccg    7740
agcgcagaag tggtcctgca actttatccg cctccatcca gtctattaat tgttgccggg    7800
aagctagagt aagtagttcg ccagttaata gtttgcgcaa cgttgttgcc attgctacag    7860
gcatcgtggt gtcacgctcg tcgtttggta tggcttcatt cagctccggt tcccaacgat    7920
caaggcgagt tacatgatcc cccatgttgt gcaaaaaagc ggttagctcc ttcggtcctc    7980
cgatcgttgt cagaagtaag ttggccgcag tgttatcact catggttatg gcagcactgc    8040
ataattctct tactgtcatg ccatccgtaa gatgcttttc tgtgactggt gagtactcaa    8100
ccaagtcatt ctgagaatag tgtatgcggc gaccgagttg ctcttgcccg gcgtcaatac    8160
gggataatac cgcgccacat agcagaactt taaaagtgct catcattgga aaacgttctt    8220
cggggcgaaa actctcaagg atcttaccgc tgttgagatc cagttcgatg taacccactc    8280
gtgcacccaa ctgatcttca gcatctttta ctttcaccag cgtttctggg tgagcaaaaa    8340
caggaaggca aaatgccgca aaaaagggaa taagggcgac acggaaatgt tgaatactca    8400
tactcttcct ttttcaatat tattgaagca tttatcaggg ttattgtctc atgagcggat    8460
acatatttga atgtatttag aaaaataaac aaataggggt tccgcgcaca tttccccgaa    8520
aagtgccacc tgacgtctaa gaaaccatta ttatcatgac attaacctat aaaaataggc    8580
gtatcacgag gccctttcgt ctcgcgcgtt tcggtgatga cggtgaaaac ctctgacaca    8640
tgcagctccc ggagacggtc acagcttgtc tgtaagcgga tgccgggagc agacaagccc    8700
gtcagggcgc gtcagcgggt gttggcgggt gtcgggctg gcttaactat gcggcatcag    8760
agcagattgt actgagagtg caccatatgc ggtgtgaaat accgcacaga tgcgtaagga    8820
gaaaataccg catcaggcgc cattcgccat tcaggctgcg caactgttgg gaagggcgat    8880
cggtgcgggc ctcttcgcta ttacgccagc tggcgaaagg gggatgtgct gcaaggcgat    8940
taagttgggt aacgccaggg ttttcccagt cacgacgttg taaaacgacg gccagtgcca    9000
agctgacgcg                                                          9010
```

<210> SEQ ID NO 7

<211> LENGTH: 10245
<212> TYPE: DNA
<213> ORGANISM: Artificial Sequence
<220> FEATURE:
<223> OTHER INFORMATION: EKC lentiviral transfer plasmid

<400> SEQUENCE: 7

| | | | | | |
|---|---|---|---|---|---|
| taaataaata | aataaataat | ataaataata | aatgtccagg | aatcagagct | caaactcaga | 60 |
| tccttagtct | taaactccag | tcccttttct | tcctaactcc | aagaccttgg | agtaagatct | 120 |
| tgtggctgta | ggtatggctg | atgccctgaa | gagttgaagt | tggcagggaa | ggtgcccaga | 180 |
| aaattttgga | ttgaagattt | catggcaagt | ctctggccag | tggcctagcc | cgggtaagcc | 240 |
| atgctatgct | cacctcccca | cagccccctc | tcgcctttt | ttttttttt | ttttaccttg | 300 |
| actggaagca | caagcagaaa | ctgggacatg | agcaccagga | gaccagattt | ccatggtccc | 360 |
| gttggggca | tggggttggg | gagaggttgc | agaggagggc | tctggagggg | agcaactgtc | 420 |
| acagctgtga | gaggtggggg | tgagcaggca | gtcagggctg | ttccctccag | aatcctgggg | 480 |
| tgtcctctgc | acttctgcgc | caagctggag | tgctagtgtg | atggacaagg | tggtaagaga | 540 |
| gctgaaagag | cacgagcata | acaagaaaga | cagaggcaga | agcaaaaaaa | aaaaaaaaa | 600 |
| aaaacagagg | gcaacagaga | gacagttaca | gagactacag | tgatccacag | agggagagcc | 660 |
| atccctgtga | attagccatc | atttccctgt | aaaccttaga | acccagctgt | tgccagggca | 720 |
| acggggcaat | acctgtctct | ctagagatga | agttgccagg | gtaactgcat | cctgtcattc | 780 |
| gttcctgggg | accatccgga | atgcggcacc | cactggctgt | taccatggca | actgcctttt | 840 |
| tgccccactt | aatcccatcc | cgtctgctac | aagggcccca | cagttggagg | tggggaggt | 900 |
| gggaagagaa | aagatcactt | gtggacaaag | tttgctctat | tccacctcct | ccaggccctc | 960 |
| cttgggtcca | tcaccccagg | ggtgctgggt | ccatcccacc | cccaggccca | cacaggcttg | 1020 |
| cagtattgtg | tgcggtatgg | tcagggcgtc | cgagagcagg | tttcgcagtg | gaaggcaggc | 1080 |
| aggtgttggg | gaggcagtta | ccggggcaac | gggaacaggg | cgttttggag | gtggttgcca | 1140 |
| tggggacctg | gatgctgacg | aaggctcgcg | aggctgtgag | cagccacagt | gccctgctca | 1200 |
| gaagccccgg | gctcgtcagt | caaaccggtt | ctctgtttgc | actcggcagc | acgggcaggc | 1260 |
| aagtggtccc | taggttcggg | agcagagcag | cagcgccgga | tccgccacca | tgcccgccat | 1320 |
| gaagatcgag | tgccgcatca | ccggcaccct | gaacggcgtg | gagttcgagc | tggtgggcgg | 1380 |
| cggagagggc | acccccgagc | agggccgcat | gaccaacaag | atgaagagca | ccaaaggcgc | 1440 |
| cctgaccttc | agcccctacc | tgctgagcca | cgtgatgggc | tacggcttct | accacttcgg | 1500 |
| cacctacccc | agcggctacg | agaacccctt | cctgcacgcc | atcaacaacg | gcggctacac | 1560 |
| caacacccgc | atcgagaagt | acgaggacgg | cggcgtgctg | cacgtgagct | tcagctaccg | 1620 |
| ctacgaggcc | ggccgcgtga | tcggcgactt | caaggtggtg | ggcaccggct | tccccgagga | 1680 |
| cagcgtgatc | ttcaccgaca | agatcatccg | cagcaacgcc | accgtggagc | acctgcaccc | 1740 |
| catgggcgat | aacgtgctgg | tgggcagctt | cgcccgcacc | ttcagcctgc | gcgacggcgg | 1800 |
| ctactacagc | ttcgtggtgg | acagccacat | gcacttcaag | agcgccatcc | accccagcat | 1860 |
| cctgcagaac | gggggcccca | tgttcgcctt | ccgccgcgtg | gaggagctgc | acagcaacac | 1920 |
| cgagctgggc | atcgtggagt | accagcacgc | cttcaagacc | cccatcgcct | tcgccagatc | 1980 |
| tcgagatatc | agccatggct | tcccgccggc | ggtggcggcg | caggatgatg | gcacgctgcc | 2040 |
| catgtcttgt | gcccaggaga | gcgggatgga | ccgtcaccct | gcagcctgtg | cttctgctag | 2100 |
| gatcaatgtg | accggtgagg | gcagaggaag | tcttctaaca | tgcggtgacg | tggaggagaa | 2160 |

```
tcccggccct tccggttgta cagattctag agctagcatg accgtgatga gcggcgagaa    2220
cgtggacgag gcctctgccg ctcctggaca ccctcaggat ggcagctatc ccagacaggc    2280
cgaccacgac gatcacgagt gctgcgagcg ggtcgtgatc aacatcagcg gcctgagatt    2340
cgagacacag ctgaaaaccc tggcccagtt ccccaacacc ctgctgggca ccccaagaa    2400 acggatgcgg tacttcgacc ccctgcggaa cgagtacttc ttcgaccgga accggcccag    2460
cttcgacgcc atcctgtact actaccgagc ggcggcaga ctgcggaggc ccgtgaatgt    2520 gccctggac atgttcagcg aggaaatcaa gttctacgag ctgggcgagg aagccatgga    2580
aaagttcaga gaggacgagg gcttcatcaa agaggaagag aggcccctgc ccgagaaaga    2640
ataccagaga caagtgtggc tgctgttcga gtaccccgag tctagcggcc ctgccagagt    2700
gatcgccatc gtgtccgtga tggtcatcct gatctctatc gtgatcttct gcctggaaac    2760
cctgcctgag ctgaaggacg acaaggactt caccggcacc gtgcaccgga tcgacaacac    2820
caccgtgatc tacaacagca atatcttcac cgacccattc ttcatcgtgg aaacactgtg    2880
catcatctgg ttcagcttcg agctggtcgt gcggttcttc gcctgcccca gcaagaccga    2940
cttcttcaag aacatcatga acttcattga tatcgtggcc atcatcccct acttcatcac    3000
cctgggcacc gagatcgccg agcaggaagg caatcagaag ggcgagcagg ccaccagcct    3060
ggccattctg agagtgatca gactcgtgcg ggtgttccgg atcttcaagc tgagccggca    3120
cagcaagggc ctgcagatcc tgggccagac actgaaggcc agcatgagag agctgggcct    3180
gctgatcttc tttctgttca tcggcgtgat cctgttcagc agcgccgtgt acttcgccga    3240
ggccgaagaa gccgagagcc acttcagctc tatccccgac gccttttggt gggccgtggt    3300
gtccatgacc acagtgggct acggcgacat ggtgcccgtg acaatcggcg gcaagatcgt    3360
gggcagcctg tgtgccattg ccggcgtgct gacagtcgcc ctgcctgtgc ctgtgatcgt    3420
gtccaacttc aactacttct accaccggga aaccgagggg gaggaacagg ctcagctgct    3480
gcacgtgtcc agccccaatc tggccagcga cagcgacctg agcagacggt ctagcagcac    3540
catgagcaag agcgagtaca tggaaatcga agaggacatg aacaactcta tcgcccacta    3600
ccgccaagtg aacatccgga ccgccaactg caccaccgcc aaccagaact gcgtgaacaa    3660
gagcaagctg ctgaccgatg tctgagtcga caatcaacct ctggattaca aaatttgtga    3720
aagattgact ggtattctta actatgttgc tccttttacg ctatgtggat acgctgcttt    3780
aatgcctttg tatcatgcta ttgcttcccg tatggctttc attttctcct ccttgtataa    3840
atcctggttg ctgtctcttt atgaggagtt gtggcccgtt gtcaggcaac gtggcgtggt    3900
gtgcactgtg tttgctgacg caaccccac tggttgggc attgccacca cctgtcagct    3960
cctttccggg actttcgctt tccccctccc tattgccacg gcggaactca tcgccgcctg    4020
ccttgcccgc tgctggacag gggctcggct gttgggcact gacaattccg tggtgttgtc    4080
ggggaaatca tcgtcctttc cttggctgct cgcctgtgtt gccacctgga ttctgcgcgg    4140
gacgtccttc tgctacgtcc cttcggccct caatccagcg gaccttcctt cccgcggcct    4200
gctgccggct ctgcggcctc ttccgcgtct tcgccttcgc cctcagacga gtcggatctc    4260
cctttgggcc gcctccccgc ctggaattcg agctcggtac ctttaagacc aatgacttac    4320
aaggcagctg tagatcttag ccactttta aaagaaaagg ggggactgga agggctaatt    4380
cactcccaac gaagacaaga tctgcttttt gcttgtactg ggtctctctg gttagaccag    4440
atctgagcct gggagctctc tggctaacta gggaacccac tgcttaagcc tcaataaagc    4500
```

-continued

```
ttgccttgag tgcttcaagt agtgtgtgcc cgtctgttgt gtgactctgg taactagaga    4560
tccctcagac ccttttagtc agtgtggaaa atctctagca gtagtagttc atgtcatctt    4620
attattcagt atttataact tgcaaagaaa tgaatatcag agagtgagag gaacttgttt    4680
attgcagctt ataatggtta caaataaagc aatagcatca caaatttcac aaataaagca    4740 ttttttcac tgcattctag ttgtggtttg tccaaactca tcaatgtatc ttatcatgtc    4800
tggctctagc tatcccgccc ctaactccgc ccatcccgcc cctaactccg cccagttccg    4860
cccattctcc gccccatggc tgactaattt tttttattta tgcagaggcc gaggccgcct    4920
cggcctctga gctattccag aagtagtgag gaggcttttt tggaggccta gggacgtacc    4980
caattcgccc tatagtgagt cgtattacgc gcgctcactg gccgtcgttt tacaacgtcg    5040
tgactgggaa aaccctggcg ttacccaact aatcgccttg cagcacatc cccctttcgc    5100 cagctggcgt aatagcgaag aggcccgcac cgatcgccct tcccaacagt tgcgcagcct    5160
gaatggcgaa tgggacgcgc cctgtagcgg cgcattaagc gcggcgggtg tggtggttac    5220
gcgcagcgtg accgctacac ttgccagcgc cctagcgccc gctcctttcg ctttcttccc    5280
ttcctttctc gccacgttcg ccggctttcc ccgtcaagct ctaaatcggg gctccctttt    5340
agggttccga tttagtgctt tacggcacct cgaccccaaa aaacttgatt agggtgatgg    5400
ttcacgtagt gggccatcgc cctgatagac ggtttttcgc cctttgacgt tggagtccac    5460
gttctttaat agtggactct tgttccaaac tggaacaaca ctcaaccta tctcggtcta    5520 ttctttgat ttataaggga ttttgccgat ttcggcctat tggttaaaaa atgagctgat    5580
ttaacaaaaa tttaacgcga attttaacaa aatattaacg cttacaattt aggtggcact    5640
tttcggggaa atgtgcgcgg aaccctatt tgtttatttt tctaaataca ttcaaatatg    5700
tatccgctca tgagacaata accctgataa atgcttcaat aatagcacct agatcaagag    5760
acaggatgag gatcgtttcg catgattgaa caagatggat tgcacgcagg ttctccggcc    5820
gcttgggtgg agaggctatt cggctatgac tgggcacaac agacaatcgg ctgctctgat    5880
gccgccgtgt tccggctgtc agcgcagggg cgcccggttc ttttttgtcaa gaccgacctg    5940 tccggtgccc tgaatgaact gcaagacgag gcagcgcggc tatcgtggct ggccacgacg    6000
ggcgttcctt gcgcagctgt gctcgacgtt gtcactgaag cgggaaggga ctggctgcta    6060
ttgggcgaag tgccggggca ggatctcctg tcatctcacc ttgctcctgc cgagaaagta    6120
tccatcatgg ctgatgcaat gcggcggctg catacgcttg atccggctac ctgcccattc    6180
gaccaccaag cgaaacatcg catcgagcga gcacgtactc ggatggaagc cggtcttgtc    6240
gatcaggatg atctggacga agagcatcag gggctcgcgc cagccgaact gttcgccagg    6300
ctcaaggcga gcatgcccga cggcgaggat ctcgtcgtga cccatggcga tgcctgcttg    6360
ccgaatatca tggtggaaaa tggccgcttt tctggattca tcgactgtgg ccggctgggt    6420
gtggcggacc gctatcagga catagcgttg gctacccgtg atattgctga agagcttggc    6480
ggcgaatggg ctgaccgctt cctcgtgctt tacggtatcg ccgctcccga ttcgcagcgc    6540
atcgccttct atcgccttct tgacgagttc ttctgaatta ttaacgctta caatttcctg    6600
atgcggtatt ttctccttac gcatctgtgc ggtatttcac accgcatcag gtggcacttt    6660
tcggggaaat gtgcgcggaa cccctatttg tttatttttc taaatacatt caaatatgta    6720
tccgctcatg accaaaatcc cttaacgtga gttttcgttc cactgagcgt cagacccgt    6780 agaaaagatc aaaggatctt cttgagatcc ttttttctg cgcgtaatct gctgcttgca    6840
aacaaaaaaa ccaccgctac cagcggtggt ttgtttgccg gatcaagagc taccaactct    6900
```

```
ttttccgaag gtaactggct tcagcagagc gcagatacca aatactgttc ttctagtgta   6960
gccgtagtta ggccaccact tcaagaactc tgtagcaccg cctacatacc tcgctctgct   7020
aatcctgtta ccagtggctg ctgccagtgg cgataagtcg tgtcttaccg ggttggactc   7080
aagacgatag ttaccggata aggcgcagcg gtcgggctga acgggggggt cgtgcacaca   7140
gcccagcttg gagcgaacga cctacaccga actgagatac ctacagcgtg agctatgaga   7200
aagcgccacg cttcccgaag ggagaaaggc ggacaggtat ccgtaagcg gcagggtcgg    7260
aacaggagag cgcacgaggg agcttccagg gggaaacgcc tggtatcttt atagtcctgt   7320
cgggtttcgc cacctctgac ttgagcgtcg attttgtga tgctcgtcag ggggcggag    7380
cctatggaaa aacgccagca acgcggcctt tttacggttc ctggccttt gctggccttt    7440
tgctcacatg ttctttcctg cgttatcccc tgattctgtg gataaccgta ttaccgcctt   7500
tgagtgagct gataccgctc gccgcagccg aacgaccgag cgcagcgagt cagtgagcga   7560
ggaagcggaa gagcgcccaa tacgcaaacc gcctctcccc gcgcgttggc cgattcatta   7620
atgcagctgg cacgacaggt ttcccgactg gaaagcgggc agtgagcgca acgcaattaa   7680
tgtgagttag ctcactcatt aggcacccca ggctttacac tttatgcttc cggctcgtat   7740
gttgtgtgga attgtgagcg gataacaatt tcacacagga aacagctatg accatgatta   7800
cgccaagcgc gcaattaacc ctcactaaag ggaacaaaag ctggagctgc aagcttggcc   7860
attgcatacg ttgtatccat atcataatat gtacatttat attggctcat gtccaacatt   7920
accgccatgt tgacattgat tattgactag ttattaatag taatcaatta cggggtcatt   7980
agttcatagc ccatatatgg agttccgcgt tacataactt acggtaaatg gcccgcctgg   8040
ctgaccgccc aacgaccccc gcccattgac gtcaataatg acgtatgttc ccatagtaac   8100
gccaataggg actttccatt gacgtcaatg ggtggagtat ttacggtaaa ctgcccactt   8160
ggcagtacat caagtgtatc atatgccaag tacgccccct attgacgtca atgacggtaa   8220
atggcccgcc tggcattatg cccagtacat gaccttatgg gactttccta cttggcagta   8280
catctacgta ttagtcatcg ctattaccat ggtgatgcgg ttttggcagt acatcaatgg   8340
gcgtggatag cggtttgact cacggggatt tccaagtctc cacccattg acgtcaatgg    8400
gagtttgttt tggcaccaaa atcaacggga ctttccaaaa tgtcgtaaca actccgcccc   8460
attgacgcaa atgggcggta ggcgtgtacg gtgggaggtc tatataagca gagctcgttt   8520
agtgaaccgg ggtctctctg gttagaccag atctgagcct gggagctctc tggctaacta   8580
gggaacccac tgcttaagcc tcaataaagc ttgccttgag tgcttcaagt agtgtgtgcc   8640
cgtctgttgt gtgactctgg taactagaga tccctcagac cctttagtc agtgtggaaa    8700
atctctagca gtggcgcccg aacagggact tgaaagcgaa agggaaacca gaggagctct   8760
ctcgacgcag gactcggctt gctgaagcgc gcacggcaag aggcgagggg cggcgactgg   8820
tgagtacgcc aaaattttg actagcggag gctagaagga gagagatggg tgcgagagcg   8880
tcagtattaa gcgggggaga attagatcgc gatgggaaaa aattcggtta aggccagggg   8940
gaaagaaaaa atataaatta aaacatatag tatgggcaag cagggagcta aacgattcg    9000
cagttaatcc tggcctgtta gaaacatcag aaggctgtag acaaatactg ggacagctac   9060
aaccatccct tcagacagga tcagaagaac ttagatcatt atataataca gtagcaaccc   9120
tctattgtgt gcatcaaagg atagagataa aagcaccaa ggaagcttta gacaagatag    9180
aggaagagca aaacaaaagt aagaccaccg cacagcaagc ggccgctgat cttcagacct   9240
```

| | | | | |
|---|---|---|---|---|
| ggaggaggag | atatgaggga | caattggaga | agtgaattat | ataaatataa agtagtaaaa | 9300 |
| attgaaccat | taggagtagc | acccaccaag | gcaaagagaa | gagtggtgca gagagaaaaa | 9360 |
| agagcagtgg | gaataggagc | tttgttcctt | gggttcttgg | gagcagcagg aagcactatg | 9420 |
| ggcgcagcgt | caatgacgct | gacggtacag | gccagacaat | tattgtctgg tatagtgcag | 9480 |
| cagcagaaca | atttgctgag | ggctattgag | gcgcaacagc | atctgttgca actcacagtc | 9540 |
| tggggcatca | agcagctcca | ggcaagaatc | ctggctgtgg | aaagatacct aaaggatcaa | 9600 |
| cagctcctgg | ggatttgggg | ttgctctgga | aaactcattt | gcaccactgc tgtgccttgg | 9660 |
| aatgctagtt | ggagtaataa | atctctggaa | cagatttgga | atcacacgac ctggatggag | 9720 |
| tgggacagag | aaattaacaa | ttacacaagc | ttaatacact | ccttaattga agaatcgcaa | 9780 |
| aaccagcaag | aaaagaatga | acaagaatta | ttggaattag | ataaatgggc aagtttgtgg | 9840 |
| aattggttta | acataacaaa | ttggctgtgg | tatataaaat | tattcataat gatagtagga | 9900 |
| ggcttggtag | gtttaagaat | agttttgct | gtactttcta | tagtgaatag agttaggcag | 9960 |
| ggatattcac | cattatcgtt | tcagacccac | ctcccaaccc | cgaggggacc cgacaggccc | 10020 |
| gaaggaatag | aagaagaagg | tggagagaga | gacagagaca | gatccattcg attagtgaac | 10080 |
| ggatctcgac | ggtatcggtt | aacttttaaa | agaaaagggg | ggattggggg gtacagtgca | 10140 |
| ggggaaagaa | tagtagacat | aatagcaaca | gacatacaaa | ctaaagaatt acaaaaacaa | 10200 |
| attacaaaat | tcaaaatttt | atcgaattcc | acggggttaa | tcgaa | 10245 |

<210> SEQ ID NO 8
<211> LENGTH: 8676
<212> TYPE: DNA
<213> ORGANISM: Artificial Sequence
<220> FEATURE:
<223> OTHER INFORMATION: dscGFP-only control transfer plasmid

<400> SEQUENCE: 8

| | | | | |
|---|---|---|---|---|
| taaataaata | aataaataat | ataaataata | aatgtccagg | aatcagagct caaactcaga | 60 |
| tccttagtct | taaactccag | tcccttttct | tcctaactcc | aagaccttgg agtaagatct | 120 |
| tgtggctgta | ggtatggctg | atgccctgaa | gagttgaagt | tggcagggaa ggtgcccaga | 180 |
| aaattttgga | ttgaagattt | catggcaagt | ctctggccag | tggcctagcc cgggtaagcc | 240 |
| atgctatgct | cacctcccca | cagccccctc | tcgccttttt | ttttttttt tttttttacct | 300 |
| tgactggaag | cacaagcaga | aactgggaca | tgagcaccag | gagaccagat ttccatggtc | 360 |
| ccgttggggg | catggggttg | gggagaggtt | gcagaggagg | gctctggagg ggagcaactg | 420 |
| tcacagctgt | gagaggtggg | ggtgagcagg | cagtcagggc | tgttccctcc agaatcctgg | 480 |
| ggtgtcctct | gcacttctgc | gccaagctgg | agtgctagtg | tgatggacaa ggtggtaaga | 540 |
| gagctgaaag | agcacgagca | taacaagaaa | gacagaggca | gaagcaaaaa aaaaaaaaaa | 600 |
| aaaaaaacag | agggcaacag | agagacagtt | acagagacta | cagtgatcca cagagggaga | 660 |
| gccatccctg | tgaattagcc | atcatttccc | tgtaaacctt | agaacccagc tgttgccagg | 720 |
| gcaacggggc | aatacctgtc | tctctagaga | tgaagttgcc | agggtaactg catcctgtca | 780 |
| ttcgttcctg | ggaccatcc | ggaatgcggc | acccactggc | tgttaccatg gcaactgcct | 840 |
| ttttgcccca | cttaatccca | tcccgtctgc | tacaagggcc | ccacagttgg aggtggggga | 900 |
| ggtgggaaga | gaaaagatca | cttgtggaca | aagtttgctc | tattccacct cctccaggcc | 960 |
| ctccttgggt | ccatcacccc | aggggtgctg | ggtccatccc | accccaggc ccacacaggc | 1020 |
| ttgcagtatt | gtgtgcggta | tggtcagggc | gtccgagagc | aggtttcgca gtggaaggca | 1080 |

```
ggcaggtgtt ggggaggcag ttaccggggc aacgggaaca gggcgttttg gaggtggttg   1140
ccatggggac ctggatgctg acgaaggctc gcgaggctgt gagcagccac agtgccctgc   1200
tcagaagccc cgggctcgtc agtcaaaccg gttctctgtt tgcactcggc agcacgggca   1260
ggcaagtggt ccctaggttc gggagcagag cagcagcgcc ggatccgcca ccatgcccgc   1320
catgaagatc gagtgccgca tcaccggcac cctgaacggc gtggagttcg agctggtggg   1380
cggcggagag ggcaccccc g agcagggccg catgaccaac aagatgaaga gcaccaaagg   1440
cgccctgacc ttcagcccct acctgctgag ccacgtgatg ggctacggct tctaccactt   1500
cggcacctac cccagcggct acgagaaccc cttcctgcac gccatcaaca cggcggcta   1560 caccaacacc cgcatcgaga agtacgagga cggcggcgtg ctgcacgtga gcttcagcta   1620
ccgctacgag gccggccgcg tgatcggcga cttcaaggtg gtgggcaccg gcttccccga   1680
ggacagcgtg atcttcaccg acaagatcat ccgcagcaac gccaccgtgg agcacctgca   1740
ccccatgggc gataacgtgc tggtgggcag cttcgcccgc accttcagcc tgcgcgacgg   1800
cggctactac agcttcgtgg tggacagcca catgcacttc aagagcgcca tccacccag   1860 catcctgcag aacggggggcc ccatgttcgc cttccgccgc gtggaggagc tgcacagcaa   1920
caccgagctg ggcatcgtgg agtaccagca cgccttcaag acccccatcg ccttcgccag   1980
atctcgagat atcagccatg gcttcccgcc ggcggtggcg cgcaggatg atggcacgct   2040 gcccatgtct tgtgcccagg agagcgggat ggaccgtcac cctgcagcct gtgcttctgc   2100
taggatcaat gtgtgagtcg acaatcaacc tctggattac aaaatttgtg aaagattgac   2160
tggtattctt aactatgttg ctccttttac gctatgtgga tacgctgctt taatgccttt   2220
gtatcatgct attgcttccc gtatggcttt cattttctcc tccttgtata atcctggtt   2280 gctgtctctt tatgaggagt tgtggcccgt tgtcaggcaa cgtggcgtgg tgtgcactgt   2340
gtttgctgac gcaaccccca ctggttgggg cattgccacc acctgtcagc tcctttccgg   2400
gactttcgct ttccccctcc ctattgccac ggcggaactc atcgccgcct gccttgcccg   2460
ctgctggaca ggggctcggc tgttgggcac tgacaattcc gtggtgttgt cggggaaatc   2520
atcgtccttt ccttggctgc tcgcctgtgt tgccacctgg attctgcgcg gacgtcctt   2580 ctgctacgtc ccttcggccc tcaatccagc ggaccttcct tcccgcggcc tgctgccggc   2640
tctgcggcct cttccgcgtc ttcgccttcg ccctcagacg agtcggatct ccctttgggc   2700
cgcctccccg cctggaattc gagctcggta cctttaagac caatgactta caaggcagct   2760
gtagatctta gccactttt aaaagaaaag ggggactgg aagggctaat tcactccca   2820 cgaagacaag atctgctttt tgcttgtact gggtctctct ggttagacca gatctgagcc   2880
tgggagctct ctggctaact agggaaccca ctgcttaagc ctcaataaag cttgccttga   2940
gtgcttcaag tagtgtgtgc ccgtctgttg tgtgactctg gtaactagag atccctcaga   3000 ccctttagt cagtgtggaa aatctctagc agtagtagtt catgtcatct tattattcag   3060
tatttataac ttgcaaagaa atgaatatca gagagtgaga ggaacttgtt tattgcagct   3120
tataatggtt acaaataaag caatagcatc acaaatttca caaataaagc attttttca   3180 ctgcattcta gttgtggttt gtccaaactc atcaatgtat cttatcatgt ctggctctag   3240
ctatcccgcc cctaactccg cccatcccgc cctaactccg cccagttcc gcccattctc   3300 cgccccatgg ctgactaatt tttttattt atgcagaggc cgaggccgcc tcggcctctg   3360
agctattcca gaagtagtga ggaggctttt ttggaggcct agggacgtac ccaattcgcc   3420
```

```
ctatagtgag tcgtattacg cgcgctcact ggccgtcgtt ttacaacgtc gtgactggga   3480
aaaccctggc gttacccaac ttaatcgcct tgcagcacat ccccctttcg ccagctggcg   3540
taatagcgaa gaggcccgca ccgatcgccc ttcccaacag ttgcgcagcc tgaatggcga   3600
atgggacgcg ccctgtagcg gcgcattaag cgcggcgggt gtggtggtta cgcgcagcgt   3660
gaccgctaca cttgccagcg ccctagcgcc cgctcctttc gctttcttcc cttcctttct   3720
cgccacgttc gccggctttc cccgtcaagc tctaaatcgg gggctccctt agggttccg   3780
atttagtgct ttacggcacc tcgaccccaa aaaacttgat tagggtgatg gttcacgtag   3840
tgggccatcg ccctgataga cggttttttcg ccctttgacg ttggagtcca cgttctttaa   3900
tagtggactc ttgttccaaa ctggaacaac actcaaccct atctcggtct attcttttga   3960
tttataaggg attttgccga tttcggccta ttggttaaaa aatgagctga tttaacaaaa   4020
atttaacgcg aattttaaca aaatattaac gcttacaatt taggtggcac ttttcgggga   4080
aatgtgcgcg gaaccccctat ttgtttattt ttctaaatac attcaaatat gtatccgctc   4140
atgagacaat aaccctgata aatgcttcaa taatagcacc tagatcaaga gacaggatga   4200
ggatcgtttc gcatgattga acaagatgga ttgcacgcag gttctccggc cgcttgggtg   4260
gagaggctat tcggctatga ctgggcacaa cagacaatcg gctgctctga tgccgccgtg   4320
ttccggctgt cagcgcaggg gcgcccggtt ctttttgtca agaccgacct gtccggtgcc   4380
ctgaatgaac tgcaagacga ggcagcgcgg ctatcgtggc tggccacgac gggcgttcct   4440
tgcgcagctg tgctcgacgt tgtcactgaa gcgggaaggg actggctgct attgggcgaa   4500
gtgccggggc aggatctcct gtcatctcac cttgctcctg ccgagaaagt atccatcatg   4560
gctgatgcaa tgcggcggct gcatacgctt gatccggcta cctgcccatt cgaccaccaa   4620
gcgaaacatc gcatcgagcg agcacgtact cggatggaag ccggtcttgt cgatcaggat   4680
gatctggacg aagagcatca ggggctcgcg ccagccgaac tgttcgccag gctcaaggcg   4740
agcatgcccg acgcgagga tctcgtcgtg acccatggcg atgcctgctt gccgaatatc   4800
atggtggaaa atggccgctt ttctggattc atcgactgtg gccggctggg tgtggcggac   4860
cgctatcagg acatagcgtt ggctacccgt gatattgctg aagagcttgg cggcgaatgg   4920
gctgaccgct tcctcgtgct ttacggtatc gccgctcccg attcgcagcg catcgccttc   4980
tatcgccttc ttgacgagtt cttctgaatt attaacgctt acaatttcct gatgcggtat   5040
tttctcctta cgcatctgtg cggtatttca caccgcatca ggtggcactt ttcggggaaa   5100
tgtgcgcgga acccctattt gtttattttt ctaaatacat tcaaatatgt atccgctcat   5160
gaccaaaatc ccttaacgtg agttttcgtt ccactgagcg tcagaccccg tagaaaagat   5220
caaaggatct tcttgagatc cttttttttct gcgcgtaatc tgctgcttgc aaacaaaaaa   5280
accaccgcta ccagcggtgg tttgtttgcc ggatcaagag ctaccaactc tttttccgaa   5340
ggtaactggc ttcagcagag cgcagatacc aaatactgtt cttctagtgt agccgtagtt   5400
aggccaccac ttcaagaact ctgtagcacc gcctacatac ctcgctctgc taatcctgtt   5460
accagtggct gctgccagtg gcgataagtc gtgtcttacc gggttggact caagacgata   5520
gttaccggat aaggcgcagc ggtcgggctg aacggggggt tcgtgcacac agcccagctt   5580
ggagcgaacg acctacaccg aactgagata cctacagcgt gagctatgag aaagcgccac   5640
gcttcccgaa gggagaaagg cggacaggta tccggtaagc ggcagggtcg aacaggaga   5700
gcgcacgagg gagcttccag ggggaaacgc ctggtatctt tatagtcctg tcgggtttcg   5760
ccacctctga cttgagcgtc gatttttgtg atgctcgtca ggggggcgga gcctatggaa   5820
```

```
aaacgccagc aacgcggcct ttttacggtt cctggccttt tgctggcctt ttgctcacat    5880
gttctttcct gcgttatccc ctgattctgt ggataaccgt attaccgcct ttgagtgagc    5940
tgataccgct cgccgcagcc gaacgaccga gcgcagcgag tcagtgagcg aggaagcgga    6000
agagcgccca atacgcaaac cgcctctccc cgcgcgttgg ccgattcatt aatgcagctg    6060
gcacgacagg tttcccgact ggaaagcggg cagtgagcgc aacgcaatta atgtgagtta    6120
gctcactcat taggcacccc aggctttaca ctttatgctt ccggctcgta tgttgtgtgg    6180
aattgtgagc ggataacaat ttcacacagg aaacagctat gaccatgatt acgccaagcg    6240
cgcaattaac cctcactaaa gggaacaaaa gctggagctg caagcttggc cattgcatac    6300
gttgtatcca tatcataata tgtacattta tattggctca tgtccaacat taccgccatg    6360
ttgacattga ttattgacta gttattaata gtaatcaatt acgggtcat tagttcatag     6420 cccatatatg gagttccgcg ttacataact tacggtaaat ggcccgcctg gctgaccgcc    6480
caacgacccc cgcccattga cgtcaataat gacgtatgtt cccatagtaa cgccaatagg    6540
gactttccat tgacgtcaat gggtggagta tttacggtaa actgcccact tggcagtaca    6600
tcaagtgtat catatgccaa gtacgccccc tattgacgtc aatgacggta atggcccgc     6660 ctggcattat gcccagtaca tgaccttatg gactttcct acttggcagt acatctacgt     6720
attagtcatc gctattacca tggtgatgcg gttttggcag tacatcaatg ggcgtggata    6780
gcggtttgac tcacggggat ttccaagtct ccaccccatt gacgtcaatg ggagtttgtt    6840
ttggcaccaa aatcaacggg actttccaaa atgtcgtaac aactccgccc cattgacgca    6900
aatgggcggt aggcgtgtac ggtgggaggt ctatataagc agagctcgtt tagtgaaccg    6960
gggtctctct ggttagacca gatctgagcc tgggagctct ctggctaact agggaaccca    7020
ctgcttaagc ctcaataaag cttgccttga gtgcttcaag tagtgtgtgc ccgtctgttg    7080
tgtgactctg gtaactagag atccctcaga cccttttagt cagtgtggaa aatctctagc    7140
agtggcgccc gaacagggac ttgaaagcga aagggaaacc agaggagctc tctcgacgca    7200
ggactcggct tgctgaagcg cgcacggcaa gaggcgaggg gcggcgactg gtgagtacgc    7260
caaaattttt gactagcgga ggctagaagg agagagatgg gtgcgagagc gtcagtatta    7320 agcggggggag aattagatcg cgatgggaaa aaattcggtt aaggccaggg ggaaagaaaa    7380
aatataaatt aaaacatata gtatgggcaa gcagggagct agaacgattc gcagttaatc    7440
ctggcctgtt agaaacatca gaaggctgta gacaaatact gggacagcta caaccatccc    7500
ttcagacagg atcagaagaa cttagatcat tatataatac agtagcaacc ctctattgtg    7560
tgcatcaaag gatagagata aaagacacca aggaagcttt agacaagata gaggaagagc    7620
aaaacaaaag taagaccacc gcacagcaag cggccgctga tcttcagacc tggaggagga    7680
gatatgaggg acaattggag aagtgaatta tataaatata agtagtaaa aattgaacca     7740 ttaggagtag cacccaccaa ggcaaagaga agagtggtgc agagagaaaa aagagcagtg    7800
ggaataggag ctttgttcct tgggttcttg ggagcagcag gaagcactat gggcgcagcg    7860
tcaatgacgc tgacggtaca ggccagacaa ttattgtctg gtatagtgca gcagcagaac    7920
aatttgctga gggctattga ggcgcaacag catctgttgc aactcacagt ctggggcatc    7980
aagcagctcc aggcaagaat cctggctgtg aaagatacc taaggatca acagctcctg     8040 gggatttggg gttgctctgg aaaactcatt tgcaccactg ctgtgccttg gaatgctagt    8100
tggagtaata aatctctgga acagatttgg aatcacacga cctggatgga gtgggacaga    8160
```

```
gaaattaaca attacacaag cttaatacac tccttaattg aagaatcgca aaaccagcaa    8220
gaaaagaatg aacaagaatt attggaatta gataaatggg caagtttgtg gaattggttt    8280
aacataacaa attggctgtg gtatataaaa ttattcataa tgatagtagg aggcttggta    8340
ggtttaagaa tagttttttgc tgtactttct atagtgaata gagttaggca gggatattca    8400
ccattatcgt ttcagaccca cctcccaacc ccgaggggac ccgacaggcc cgaaggaata    8460
gaagaagaag gtggagagag agacagagac agatccattc gattagtgaa cggatctcga    8520
cggtatcggt taacttttaa agaaaaggg gggattgggg ggtacagtgc aggggaaaga    8580 atagtgagaca taatagcaac agacatacaa actaaagaat tacaaaaaca aattacaaaa    8640
ttcaaaattt tatcgaattc cacggggtta atcgaa                              8676
```

<210> SEQ ID NO 9
<211> LENGTH: 6026
<212> TYPE: DNA
<213> ORGANISM: Artificial Sequence
<220> FEATURE:
<223> OTHER INFORMATION: Nucleotide sequence of an exemplary engineered
      KCNA1 gene viral vector lacking a reporter (without bacterial
      plasmid portion
<220> FEATURE:
<221> NAME/KEY: misc_feature
<222> LOCATION: (4760)..(4760)
<223> OTHER INFORMATION: N = T or C

<400> SEQUENCE: 9

```
gacattgatt attgactagt tattaatagt aatcaattac ggggtcatta gttcatagcc      60
catatatgga gttccgcgtt acataactta cggtaaatgg cccgcctggc tgaccgccca    120
acgacccccg cccattgacg tcaataatga cgtatgttcc catagtaacg ccaatagggga   180 ctttccattg acgtcaatgg gtggagtatt tacggtaaac tgcccacttg gcagtacatc    240
aagtgtatca tatgccaagt acgccccta ttgacgtcaa tgacggtaaa tggcccgcct     300
ggcattatgc ccagtacatg accttatggg actttcctac ttggcagtac atctacgtat    360
tagtcatcgc tattaccatg gtgatgcggt tttggcagta catcaatggg cgtggatagc    420
ggtttgactc acggggattt ccaagtctcc accccattga cgtcaatggg agtttgtttt    480
ggcaccaaaa tcaacgggac tttccaaaat gtcgtaacaa ctccgcccca ttgacgcaaa    540
tgggcggtag cgtgtacgg tgggaggtct atataagcag agctcgttta gtgaaccggg    600
gtctctctgg ttagaccaga tctgagcctg ggagctctct ggctaactag ggaacccact    660
gcttaagcct caataaagct tgccttgagt gcttcaagta gtgtgtgccc gtctgttgtg    720
tgactctggt aactagagat ccctcagacc ctttttagtca gtgtggaaaa tctctagcag    780
tggcgcccga acagggactt gaaagcgaaa gggaaaccag aggagctctc tcgacgcagg    840
actcggcttg ctgaagcgcg cacggcaaga ggcgaggggc ggcgactggt gagtacgcca    900
aaaattttga ctagcggagg ctagaaggag agagatgggt gcgagagcgt cagtattaag    960
cgggggagaa ttagatcgcg atgggaaaaa attcggttaa ggccaggggg aaagaaaaaa   1020
tataaattaa aacatatagt atgggcaagc agggagctag aacgattcgc agttaatcct   1080
ggcctgttag aaacatcaga aggctgtaga caaatactgg gacagctaca accatccctt   1140
cagacaggat cagaagaact tagatcatta tataatacag tagcaacccct ctattgtgtg   1200 catcaaagga tagagataaa agacaccaag gaagctttag acaagataga ggaagagcaa   1260
aacaaaagta agaccaccgc acagcaagcg gccgctgatc ttcagacctg gaggaggaga   1320
tatgagggac aattggagaa gtgaattata taaatataaa gtagtaaaaa ttgaaccatt   1380
```

```
aggagtagca cccaccaagg caaagagaag agtggtgcag agagaaaaaa gagcagtggg    1440
aataggagct ttgttccttg ggttcttggg agcagcagga agcactatgg gcgcagcgtc    1500
aatgacgctg acggtacagg ccagacaatt attgtctggt atagtgcagc agcagaacaa    1560
tttgctgagg gctattgagg cgcaacagca tctgttgcaa ctcacagtct ggggcatcaa    1620
gcagctccag gcaagaatcc tggctgtgga agataccta aaggatcaac agctcctggg    1680
gatttggggt tgctctggaa aactcatttg caccactgct gtgccttgga atgctagttg    1740
gagtaataaa tctctggaac agatttggaa tcacacgacc tggatggagt gggacagaga    1800
aattaacaat tacacaagct taatacactc cttaattgaa gaatcgcaaa accagcaaga    1860
aaagaatgaa caagaattat tggaattaga taaatgggca agtttgtgga attggtttaa    1920
cataacaaat tggctgtggt atataaaatt attcataatg atagtaggag gcttggtagg    1980
tttaagaata gtttttgctg tactttctat agtgaataga gttaggcagg gatattcacc    2040
attatcgttt cagacccacc tcccaacccc gaggggaccc gacaggcccg aaggaataga    2100
agaagaaggt ggagagagag acagagacag atccattcga ttagtgaacg gatctcgacg    2160
gtatcggtta acttttaaaa gaaaggggg gattgggggg tacagtgcag gggaaagaat    2220
agtagacata atagcaacag acatacaaac taaagaatta caaaaacaaa ttacaaaatt    2280
caaaatttta tcgaattcca cggggttaat cgaataaata aataaataaa taatataaat    2340
aataaatgtc caggaatcag agctcaaact cagatcctta gtcttaaact ccagtccctt    2400
ttcttcctaa ctccaagacc ttggagtaag atcttgtggc tgtaggtatg gctgatgccc    2460
tgaagagttg aagttggcag ggaaggtgcc cagaaaattt tggattgaag atttcatggc    2520
aagtctctgg ccagtggcct agcccgggta agccatgcta tgctcacctc cccacagccc    2580
cctctcgcct tttttttttt tttttttac cttgactgga agcacaagca gaaactggga    2640
catgagcacc aggagaccag atttccatgg tcccgttggg ggcatggggt tggggagagg    2700
ttgcagagga gggctctgga ggggagcaac tgtcacagct gtgagaggtg ggggtgagca    2760
ggcagtcagg gctgttccct ccagaatcct ggggtgtcct ctgcacttct gcgccaagct    2820
ggagtgctag tgtgatggac aaggtggtaa gagagctgaa agagcacgag cataacaaga    2880
aagacagagg cagaagcaaa aaaaaaaaaa aaaaaaaaca gagggcaaca gagagacagt    2940
tacagagact acagtgatcc acagagggag agccatccct gtgaattagc catcatttcc    3000 ctgtaaaacct tagaacccag ctgttgccag ggcaacgggg caatacctgt ctctctagag    3060
atgaagttgc cagggtaact gcatcctgtc attcgttcct ggggaccatc cggaatgcgg    3120
cacccactgg ctgttaccat ggcaactgcc tttttgcccc acttaatccc atcccgtctg    3180
ctacaagggc cccacagttg gaggtggggg aggtgggaag agaaaagatc acttgtggac    3240
aaagtttgct ctattccacc tcctccaggc cctccttggg tccatcaccc cagggggtgct    3300 gggtccatcc caccccagg cccacacagg cttgcagtat tgtgtgcggt atggtcaggg    3360
cgtccgagag caggtttcgc agtggaaggc aggcaggtgt tggggaggca gttaccgggg    3420
caacgggaac agggcgtttt ggaggtggtt gccatgggga cctggatgct gacgaaggct    3480
cgcgaggctg tgagcagcca cagtgccctg ctcagaagcc ccgggctcgt cagtcaaacc    3540
ggttctctgt ttgcactcgg cagcacgggc aggcaagtgg tccctaggtt cgggagcaga    3600
gcagcagcgc cggatccgcc accatgaccg tgatgagcgg cgagaacgtg gacgaggcct    3660
ctgccgctcc tggacaccct caggatggca gctatcccag acaggccgac cacgacgatc    3720
```

```
acgagtgctg cgagcgggtc gtgatcaaca tcagcggcct gagattcgag acacagctga    3780
aaaccctggc ccagttcccc aacaccctgc tgggcaaccc caagaaacgg atgcggtact    3840
tcgaccccct gcggaacgag tacttcttcg accggaaccg gcccagcttc gacgccatcc    3900
tgtactacta ccagagcggc ggcagactgc ggaggcccgt gaatgtgccc ctggacatgt    3960
tcagcgagga aatcaagttc tacgagctgg gcgaggaagc catggaaaag ttcagagagg    4020
acgagggctt catcaaagag gaagagaggc ccctgcccga aaagaatac cagagacaag     4080
tgtggctgct gttcgagtac cccgagtcta gcggccctgc cagagtgatc gccatcgtgt    4140
ccgtgatggt catcctgatc tctatcgtga tcttctgcct ggaaaccctg cctgagctga    4200
aggacgacaa ggacttcacc ggcaccgtgc accggatcga caacaccacc gtgatctaca    4260
acagcaatat cttcaccgac ccattcttca tcgtggaaac actgtgcatc atctggttca    4320
gcttcgagct ggtcgtgcgg ttcttcgcct gccccagcaa gaccgacttc ttcaagaaca    4380
tcatgaactt cattgatatc gtggccatca tcccctactt catcaccctg gcaccgaga     4440
tcgccgagca ggaaggcaat cagaagggcg agcaggccac cagcctggcc attctgagag    4500
tgatcagact cgtgcgggtg ttccggatct tcaagctgag ccggcacagc aagggcctgc    4560
agatcctggg ccagacactg aaggccagca tgagagagct gggcctgctg atcttctttc    4620
tgttcatcgg cgtgatcctg ttcagcagcg ccgtgtactt cgccgaggcc gaagaagccg    4680
agagccactt cagctctatc cccgacgcct tttggtgggc cgtggtgtcc atgaccacag    4740
tgggctacgg cgacatgtan cccgtgacaa tcggcggcaa gatcgtgggc agcctgtgtg    4800
ccattgccgg cgtgctgaca gtcgccctgc ctgtgcctgt gatcgtgtcc aacttcaact    4860
acttctacca ccgggaaacc gaggggagg aacaggctca gctgctgcac gtgtccagcc      4920
ccaatcggc cagcgacagc gacctgagca gacggtctag cagcaccatg agcaagagcg     4980
agtacatgga aatcgaagag gacatgaaca actctatcgc ccactaccgc caagtgaaca    5040
tccggaccgc caactgcacc accgccaacc agaactgcgt gaacaagagc aagctgctga    5100
ccgatgtctg agtcgacaat caacctctgg attacaaaat ttgtgaaaga ttgactggta    5160
ttcttaacta tgttgctcct tttacgctat gtggatacgc tgctttaatg cctttgtatc    5220
atgctattgc ttcccgtatg gctttcattt tctcctcctt gtataaatcc tggttgctgt    5280
ctctttatga ggagttgtgg cccgttgtca ggcaacgtgg cgtggtgtgc actgtgtttg    5340
ctgacgcaac ccccactggt tggggcattg ccaccacctg tcagctcctt tccgggactt    5400
tcgctttccc cctccctatt gccacggcgg aactcatcgc cgcctgcctt gcccgctgct    5460
ggacagggc tcggctgttg ggcactgaca attccgtggt gttgtcgggg aaatcatcgt     5520
cctttccttg gctgctcgcc tgtgttgcca cctggattct gcgcgggacg tccttctgct    5580
acgtcccttc ggccctcaat ccagcggacc ttccttcccg cggcctgctg ccggctctgc    5640
ggcctcttcc gcgtcttcgc cttcgccctc agacgagtcg atctcccttt gggccgcct    5700
cccccgcctgg aattcgagct cggtaccttt aagaccaatg acttacaagg cagctgtaga   5760
tcttagccac ttttaaaag aaaaggggg actggaaggg ctaattcact cccaacgaag      5820
acaagatctg cttttgcttg tactgggtc tctctggtta gaccagatct gagcctggga     5880
gctctctggc taactaggga acccactgct taagcctcaa taaagcttgc cttgagtgct    5940
tcaagtagtg tgtgcccgtc tgttgtgtga ctctggtaac tagagatccc tcagaccctt    6000
ttagtcagtg tggaaaatct ctagca                                         6026
```

```
<210> SEQ ID NO 10
<211> LENGTH: 9357
<212> TYPE: DNA
<213> ORGANISM: Artificial Sequence
<220> FEATURE:
<223> OTHER INFORMATION: exemplary engineered KCNA1 gene viral vector
      lacking a reporter (with bacterial plasmid portion)
<220> FEATURE:
<221> NAME/KEY: misc_feature
<222> LOCATION: (2446)..(2446)
<223> OTHER INFORMATION: N = T or C

<400> SEQUENCE: 10
```

| | | | | | |
|---|---|---|---|---|---|
| taaataaata | aataaataat | ataaataata | aatgtccagg | aatcagagct | caaactcaga | 60 |
| tccttagtct | taaactccag | tcccttttct | tcctaactcc | aagaccttgg | agtaagatct | 120 |
| tgtggctgta | ggtatggctg | atgccctgaa | gagttgaagt | tggcagggaa | ggtgcccaga | 180 |
| aaattttgga | ttgaagattt | catggcaagt | ctctggccag | tggcctagcc | cgggtaagcc | 240 |
| atgctatgct | cacctcccca | cagcccctc | tcgccttttt | tttttttttt | ttttaccttg | 300 |
| actgaaagca | caagcagaaa | ctgggacatg | agcaccagga | gaccagattt | ccatggtccc | 360 |
| gttgggggca | tggggttggg | gagaggttgc | agaggagggc | tctggagggg | agcaactgtc | 420 |
| acagctgtga | gaggtggggg | tgagcaggca | gtcaggctg | ttccctccag | aatcctgggg | 480 |
| tgtcctctgc | acttctgcgc | caagctggag | tgctagtgtg | atggacaagg | tggtaagaga | 540 |
| gctgaaagag | cacgagcata | caagaaaga | cagaggcaga | agcaaaaaa | aaaaaaaaa | 600 |
| aaaacagagg | gcaacagaga | gacagttaca | gagactacag | tgatccacag | agggagagcc | 660 |
| atccctgtga | attagccatc | atttccctgt | aaaccttaga | acccagctgt | tgccagggca | 720 |
| acggggcaat | acctgtctct | ctagagatga | agttgccagg | gtaactgcat | cctgtcattc | 780 |
| gttcctgggg | accatccgga | atgcggcacc | cactggctgt | taccatggca | actgccttt | 840 |
| tgccccactt | aatcccatcc | cgtctgctac | aagggcccca | cagttggagg | tgggggaggt | 900 |
| gggaagagaa | aagatcactt | gtggacaaag | tttgctctat | tccacctcct | ccaggccctc | 960 |
| cttgggtcca | tcaccccagg | ggtgctgggt | ccatcccacc | cccaggccca | cacaggcttg | 1020 |
| cagtattgtg | tgcggtatgg | tcagggcgtc | cgagagcagg | tttcgcagtg | gaaggcaggc | 1080 |
| aggtgttggg | gaggcagtta | ccggggcaac | gggaacaggg | cgttttggag | gtggttgcca | 1140 |
| tggggacctg | gatgctgacg | aaggctcgcg | aggctgtgag | cagccacagt | gccctgctca | 1200 |
| gaagccccgg | gctcgtcagt | caaaccggtt | ctctgtttgc | actcggcagc | acgggcaggc | 1260 |
| aagtggtccc | taggttcggg | agcagagcag | cagcgccgga | tccgccacca | tgaccgtgat | 1320 |
| gagcggcgag | aacgtggacg | aggcctctgc | cgctcctgga | caccctcagg | atggcagcta | 1380 |
| tcccagacag | gccgaccacg | acgatcacga | gtgctgcgag | cgggtcgtga | tcaacatcag | 1440 |
| cggcctgaga | ttcgagacac | agctgaaaac | cctggcccag | ttccccaaca | ccctgctggg | 1500 |
| caaccccaag | aaacgatgc | ggtacttcga | ccccctgcgg | aacgagtact | tcttcgaccg | 1560 |
| gaaccggccc | agcttcgacg | ccatcctgta | ctactaccag | agcggcggca | gactgcggag | 1620 |
| gcccgtgaat | gtgcccctgg | acatgttcag | cgaggaaatc | aagttctacg | agctgggcga | 1680 |
| ggaagccatg | gaaaagttca | gagaggacga | gggcttcatc | aaagaggaag | agaggcccct | 1740 |
| gcccgagaaa | gaataccaga | gacaagtgtg | gctgctgttc | gagtaccccg | agtctagcgg | 1800 |
| ccctgccaga | gtgatcgcca | tcgtgtccgt | gatggtcatc | ctgatctcta | tcgtgatctt | 1860 |
| ctgcctggaa | accctgcctg | agctgaagga | cgacaaggac | ttcaccggca | ccgtgcaccg | 1920 |
| gatcgacaac | accaccgtga | tctacaacag | caatatcttc | accgacccat | tcttcatcgt | 1980 |

```
ggaaacactg tgcatcatct ggttcagctt cgagctggtc gtgcggttct tcgcctgccc    2040
cagcaagacc gacttcttca agaacatcat gaacttcatt gatatcgtgg ccatcatccc    2100
ctacttcatc accctgggca ccgagatcgc cgagcaggaa ggcaatcaga agggcgagca    2160
ggccaccagc ctggccattc tgagagtgat cagactcgtg cgggtgttcc ggatcttcaa    2220
gctgagccgg cacagcaagg gcctgcagat cctgggccag acactgaagg ccagcatgag    2280
agagctgggc ctgctgatct tctttctgtt catcggcgtg atcctgttca gcagcgccgt    2340
gtacttcgcc gaggccgaag aagccgagag ccacttcagc tctatccccg acgccttttg    2400
gtgggccgtg gtgtccatga ccacagtggg ctacggcgac atgtancccg tgacaatcgg    2460
cggcaagatc gtgggcagcc tgtgtgccat tgccggcgtg ctgacagtcg ccctgcctgt    2520
gcctgtgatc gtgtccaact tcaactactt ctaccaccgg gaaaccgagg gggaggaaca    2580
ggctcagctg ctgcacgtgt ccagccccaa tctggccagc gacagcgacc tgagcagacg    2640
gtctagcagc accatgagca agagcgagta catggaaatc gaagaggaca tgaacaactc    2700
tatcgcccac taccgccaag tgaacatccg gaccgccaac tgcaccaccg ccaaccagaa    2760
ctgcgtgaac aagagcaagc tgctgaccga tgtctgagtc gacaatcaac ctctggatta    2820
caaaatttgt gaaagattga ctggtattct taactatgtt gctccttta cgctatgtgg    2880 atacgctgct ttaatgcctt tgtatcatgc tattgcttcc cgtatggctt tcattttctc    2940
ctccttgtat aaatcctggt tgctgtctct ttatgaggag ttgtggcccg ttgtcaggca    3000
acgtggcgtg gtgtgcactg tgtttgctga cgcaaccccc actggttggg gcattgccac    3060
cacctgtcag ctcctttccg ggactttcgc tttccccctc cctattgcca cggcggaact    3120
catcgccgcc tgccttgccc gctgctggac aggggctcgg ctgttgggca ctgacaattc    3180
cgtggtgttg tcggggaaat catcgtcctt tccttggctg ctcgcctgtg ttgccacctg    3240
gattctgcgc gggacgtcct tctgctacgt ccccttcggc ctcaatccag cggaccttcc    3300
ttcccgcggc ctgctgccgg ctctgcggcc tcttccgcgt cttcgccttc gccctcagac    3360
gagtcggatc tccctttggg ccgcctcccc gcctggaatt cgagctcggt acctttaaga    3420
ccaatgactt acaaggcagc tgtagatctt agccactttt aaaagaaaaa gggggggactg    3480 gaagggctaa ttcactccca acgaagacaa gatctgcttt ttgcttgtac tgggtctctc    3540
tggttagacc agatctgagc ctgggagctc tctggctaac tagggaaccc actgcttaag    3600
cctcaataaa gcttgccttg agtgcttcaa gtagtgtgtg cccgtctgtt gtgtgactct    3660
ggtaactaga gatccctcag acccttttag tcagtgtgga aaatctctag cagtagtagt    3720
tcatgtcatc ttattattca gtatttataa cttgcaaaga atgaatatc agagagtgag    3780 aggaacttgt ttattgcagc ttataatggt tacaaataaa gcaatagcat cacaaatttc    3840
acaaataaag cattttttc actgcattct agttgtggtt tgtccaaact catcaatgta    3900
tcttatcatg tctggctcta gctatcccgc ccctaactcc gcccatcccg ccctaactc    3960 cgcccagttc cgcccattct ccgccccatg gctgactaat tttttttatt tatgcagagg    4020
ccgaggccgc ctcggcctct gagctattcc agaagtagtg aggaggcttt tttggaggcc    4080
tagggacgta cccaattcgc cctatagtga gtcgtattac gcgcgctcac tggccgtcgt    4140
tttacaacgt cgtgactggg aaaaccctgg cgttacccaa cttaatcgcc ttgcagcaca    4200
tccccctttc gccagctggc gtaatagcga agaggcccgc accgatcgcc cttcccaaca    4260
gttgcgcagc ctgaatggcg aatgggacgc gccctgtagc ggcgcattaa gcgcggcggg    4320
```

```
tgtggtggtt acgcgcagcg tgaccgctac acttgccagc gccctagcgc ccgctccttt      4380
cgctttcttc ccttcctttc tcgccacgtt cgccggcttt ccccgtcaag ctctaaatcg      4440
ggggctccct ttagggttcc gatttagtgc tttacggcac ctcgacccca aaaaacttga      4500
ttagggtgat ggttcacgta gtgggccatc gccctgatag acggttttc gccctttgac       4560 gttggagtcc acgttcttta atagtggact cttgttccaa actggaacaa cactcaaccc      4620
tatctcggtc tattcttttg atttataagg gattttgccg atttcggcct attggttaaa      4680
aaatgagctg atttaacaaa aatttaacgc gaattttaac aaaatattaa cgcttacaat      4740
ttaggtggca cttttcgggg aaatgtgcgc ggaacccta tttgtttatt tttctaaata       4800
cattcaaata tgtatccgct catgagacaa taaccctgat aaatgcttca ataatagcac      4860
ctagatcaag agacaggatg aggatcgttt cgcatgattg aacaagatgg attgcacgca      4920
ggttctccgg ccgcttgggt ggagaggcta ttcggctatg actgggcaca acagacaatc      4980
ggctgctctg atgccgccgt gttccggctg tcagcgcagg ggcgcccggt tcttttgtc       5040 aagaccgacc tgtccggtgc cctgaatgaa ctgcaagacg aggcagcgcg gctatcgtgg      5100
ctggccacga cgggcgttcc ttgcgcagct gtgctcgacg ttgtcactga agcgggaagg      5160
gactggctgc tattgggcga agtgccgggg caggatctcc tgtcatctca ccttgctcct      5220
gccgagaaag tatccatcat ggctgatgca atgcggcggc tgcatacgct tgatccggct      5280
acctgcccat tcgaccacca agcgaaacat cgcatcgagc gagcacgtac tcggatggaa      5340
gccggtcttg tcgatcagga tgatctggac gaagagcatc aggggctcgc gccagccgaa      5400
ctgttcgcca ggctcaaggc gagcatgccc gacggcgagg atctcgtcgt gacccatggc      5460
gatgcctgct tgccgaatat catggtggaa aatggccgct tttctggatt catcgactgt      5520
ggccggctgg gtgtggcgga ccgctatcag gacatagcgt tggctacccg tgatattgct      5580
gaagagcttg gcggcgaatg ggctgaccgc ttcctcgtgc tttacggtat cgccgctccc      5640
gattcgcagc gcatcgcctt ctatcgcctt cttgacgagt tcttctgaat tattaacgct      5700
tacaatttcc tgatgcggta ttttctcctt acgcatctgt gcggtatttc acaccgcatc      5760
aggtggcact tttcggggaa atgtgcgcgg aaccccta tt tgtttattttt tctaaataca     5820 ttcaaatatg tatccgctca tgaccaaaat cccttaacgt gagttttcgt tccactgagc      5880
gtcagacccc gtagaaaaga tcaaaggatc ttcttgagat cctttttttc tgcgcgtaat      5940
ctgctgcttg caaacaaaaa aaccaccgct accagcggtg gtttgtttgc cggatcaaga      6000
gctaccaact cttttccga aggtaactgg cttcagcaga gcgcagatac caaatactgt       6060
tcttctagtg tagccgtagt taggccacca cttcaagaac tctgtagcac cgcctacata      6120
cctcgctctg ctaatcctgt taccagtggc tgctgccagt ggcgataagt cgtgtcttac      6180
cgggttggac tcaagacgat agttaccgga taaggcgcag cggtcgggct gaacggggg      6240 gtcgtgcaca gcccagct tggagcgaac gacctacacc gaactgagat acctacagcg       6300
tgagctatga gaaagcgcca cgcttcccga agggagaaag gcggacaggt atccggtaag      6360
cggcagggtc ggaacaggag agcgcacgag ggagcttcca gggggaaacg cctggtatct      6420
ttatagtcct gtcgggtttc gccacctctg acttgagcgt cgatttttgt gatgctcgtc      6480
aggggggcgg agcctatgga aaaacgccag caacgcggcc ttttacggt tcctggcctt       6540 ttgctggcct tttgctcaca tgttctttcc tgcgttatcc cctgattctg tggataaccg      6600
tattaccgcc tttgagtgag ctgataccgc tcgccgcagc cgaacgaccg agcgcagcga      6660
gtcagtgagc gaggaagcgg aagagcgccc aatacgcaaa ccgcctctcc ccgcgcgttg      6720
```

```
gccgattcat taatgcagct ggcacgacag gtttcccgac tggaaagcgg gcagtgagcg    6780
caacgcaatt aatgtgagtt agctcactca ttaggcaccc caggctttac actttatgct    6840
tccggctcgt atgttgtgtg gaattgtgag cggataacaa tttcacacag gaaacagcta    6900
tgaccatgat tacgccaagc gcgcaattaa ccctcactaa agggaacaaa agctggagct    6960
gcaagcttgg ccattgcata cgttgtatcc atatcataat atgtacattt atattggctc    7020
atgtccaaca ttaccgccat gttgacattg attattgact agttattaat agtaatcaat    7080
tacggggtca ttagttcata gcccatatat ggagttccgc gttacataac ttacggtaaa    7140
tggcccgcct ggctgaccgc ccaacgaccc ccgcccattg acgtcaataa tgacgtatgt    7200
tcccatagta acgccaatag ggactttcca ttgacgtcaa tgggtggagt atttacggta    7260
aactgcccac ttggcagtac atcaagtgta tcatatgcca gtacgccccc tattgacgt    7320 caatgacggt aaatggcccg cctggcatta tgcccagtac atgaccttat gggactttcc    7380
tacttggcag tacatctacg tattagtcat cgctattacc atggtgatgc ggttttggca    7440
gtacatcaat gggcgtggat agcggtttga ctcacgggga tttccaagtc tccaccccat    7500
tgacgtcaat gggagtttgt tttggcacca aaatcaacgg gactttccaa aatgtcgtaa    7560
caactccgcc ccattgacgc aaatgggcgg taggcgtgta cggtgggagg tctatataag    7620
cagagctcgt ttagtgaacc ggggtctctc tggttagacc agatctgagc ctgggagctc    7680
tctggctaac tagggaaccc actgcttaag cctcaataaa gcttgccttg agtgcttcaa    7740
gtagtgtgtg cccgtctgtt gtgtgactct ggtaactaga gatccctcag acccttttag    7800
tcagtgtgga aaatctctag cagtggcgcc cgaacaggga cttgaaagcg aaagggaaac    7860
cagaggagct ctctcgacgc aggactcggc ttgctgaagc gcgcacggca agaggcgagg    7920
ggcggcgact ggtgagtacg ccaaaaattt tgactagcgg aggctagaag gagagagatg    7980
ggtgcgagag cgtcagtatt aagcggggga gaattagatc gcgatgggaa aaaattcggt    8040
taaggccagg gggaaagaaa aaatataaat taaaacatat agtatgggca agcagggagc    8100
tagaacgatt cgcagttaat cctggcctgt tagaaacatc agaaggctgt agacaaatac    8160
tgggacagct acaaccatcc cttcagacag gatcagaaga acttagatca ttatataata    8220
cagtagcaac cctctattgt gtgcatcaaa ggatagagat aaaagacacc aaggaagctt    8280
tagacaagat agaggaagag caaaacaaaa gtaagaccac cgcacagcaa gcggccgctg    8340
atcttcagac ctggaggagg agatatgagg gacaattgga gaagtgaatt atataaatat    8400
aaagtagtaa aaattgaacc attaggagta gcacccacca aggcaaagag aagagtggtg    8460
cagagagaaa aaagagcagt gggaatagga gctttgttcc ttgggttctt gggagcagca    8520
ggaagcacta tgggcgcagc gtcaatgacg ctgacggtac aggccagaca attattgtct    8580
ggtatagtgc agcagcagaa caatttgctg agggctattg aggcgcaaca gcatctgttg    8640
caactcacag tctggggcat caagcagctc caggcaagaa tcctggctgt ggaaagatac    8700
ctaaaggatc aacagctcct ggggatttgg ggttgctctg gaaaactcat ttgcaccact    8760
gctgtgcctt ggaatgctag ttggagtaat aaatctctgg aacagatttg gaatcacacg    8820
acctggatgg agtgggacag agaaattaac aattacacaa gcttaataca ctccttaatt    8880
gaagaatcgc aaaaccagca agaaaagaat gaacaagaat tattggaatt agataaatgg    8940
gcaagtttgt ggaattggtt taacataaca aattggctgt ggtatataaa attattcata    9000
atgatagtag gaggcttggt aggtttaaga atagtttttg ctgtactttc tatagtgaat    9060
```

| | |
|---|---|
| agagttaggc agggatattc accattatcg tttcagaccc acctcccaac cccgagggga | 9120 |
| cccgacaggc ccgaaggaat agaagaagaa ggtggagaga gagacagaga cagatccatt | 9180 |
| cgattagtga acggatctcg acggtatcgg ttaacttta aaagaaaagg ggggattggg | 9240 |
| gggtacagtg caggggaaag aatagtagac ataatagcaa cagacataca aactaaagaa | 9300 |
| ttacaaaaac aaattacaaa attcaaaatt ttatcgaatt ccacggggtt aatcgaa | 9357 |

<210> SEQ ID NO 11
<211> LENGTH: 6026
<212> TYPE: DNA
<213> ORGANISM: Artificial Sequence
<220> FEATURE:
<223> OTHER INFORMATION: exemplary engineered KCNA1 gene viral vector lacking a reporter (without bacterial plasmid portion) encoding an edited Kv1.1 potassium channel with Y379V mutation

<400> SEQUENCE: 11

| | |
|---|---|
| gacattgatt attgactagt tattaatagt aatcaattac ggggtcatta gttcatagcc | 60 |
| catatatgga gttccgcgtt acataactta cggtaaatgg cccgcctggc tgaccgccca | 120 |
| acgaccccg cccattgacg tcaataatga cgtatgttcc catagtaacg ccaatagga | 180 |
| ctttccattg acgtcaatgg gtggagtatt tacggtaaac tgcccacttg gcagtacatc | 240 |
| aagtgtatca tatgccaagt acgccccta ttgacgtcaa tgacggtaaa tggcccgcct | 300 |
| ggcattatgc ccagtacatg accttatggg actttcctac ttggcagtac atctacgtat | 360 |
| tagtcatcgc tattaccatg gtgatgcggt tttggcagta catcaatggg cgtggatagc | 420 |
| ggtttgactc acggggattt ccaagtctcc accccattga cgtcaatggg agtttgtttt | 480 |
| ggcaccaaaa tcaacgggac tttccaaaat gtcgtaacaa ctccgcccca ttgacgcaaa | 540 |
| tgggcggtag gcgtgtacgg tgggaggtct atataagcag agctcgttta gtgaaccggg | 600 |
| gtctctctgg ttagaccaga tctgagcctg ggagctctct ggctaactag ggaacccact | 660 |
| gcttaagcct caataaagct tgccttgagt gcttcaagta gtgtgtgccc gtctgttgtg | 720 |
| tgactctggt aactagagat ccctcagacc cttttagtca gtgtggaaaa tctctagcag | 780 |
| tggcgcccga acagggactt gaaagcgaaa gggaaaccag aggagctctc tcgacgcagg | 840 |
| actcggcttg ctgaagcgcg cacggcaaga ggcgaggggc ggcgactggt gagtacgcca | 900 |
| aaaattttga ctagcggagg ctagaaggag agagatgggt gcgagagcgt cagtattaag | 960 |
| cgggggagaa ttagatcgcg atgggaaaaa attcggttaa ggccaggggg aaagaaaaaa | 1020 |
| tataaattaa aacatatagt atgggcaagc agggagctag aacgattcgc agttaatcct | 1080 |
| ggcctgttag aaacatcaga aggctgtaga caaatactgg gacagctaca accatccctt | 1140 |
| cagacaggat cagaagaact tagatcatta tataatacag tagcaacccct ctattgtgtg | 1200 |
| catcaaagga tagagataaa agacaccaag gaagctttag acaagataga ggaagagcaa | 1260 |
| aacaaaagta agaccaccgc acagcaagcg gccgctgatc ttcagacctg gaggaggaga | 1320 |
| tatgagggac aattggagaa gtgaattata taaatataaa gtagtaaaaa ttgaaccatt | 1380 |
| aggagtagca cccaccaagg caaagagaag agtggtgcag agagaaaaaa gagcagtggg | 1440 |
| aataggagct ttgttccttg ggttcttggg agcagcagga agcactatgg gcgcagcgtc | 1500 |
| aatgacgctg acggtacagg ccagacaatt attgtctggt atagtgcagc agcagaacaa | 1560 |
| tttgctgagg gctattgagg cgcaacagca tctgttgcaa ctcacagtct ggggcatcaa | 1620 |
| gcagctccag gcaagaatcc tggctgtgga aagataccta aaggatcaac agctcctggg | 1680 |
| gatttggggt tgctctggaa aactcatttg caccactgct gtgccttgga atgctagttg | 1740 |

```
gagtaataaa tctctggaac agatttggaa tcacacgacc tggatggagt gggacagaga    1800
aattaacaat tacacaagct taatacactc cttaattgaa gaatcgcaaa accagcaaga    1860
aaagaatgaa caagaattat tggaattaga taaatgggca agtttgtgga attggtttaa    1920
cataacaaat tggctgtggt atataaaatt attcataatg atagtaggag gcttggtagg    1980
tttaagaata gttttgctg tactttctat agtgaataga gttaggcagg atattcacc     2040 attatcgttt cagacccacc tcccaacccc gaggggaccc gacaggcccg aaggaataga    2100
agaagaaggt ggagagagag acagagacag atccattcga ttagtgaacg gatctcgacg    2160
gtatcggtta acttttaaaa gaaaggggg gattggggg tacagtgcag gggaaagaat     2220
agtagacata atagcaacag acatacaaac taagaatta caaaacaaa ttacaaaatt     2280 caaaatttta tcgaattcca cggggttaat cgaataaata aataaataaa taatataaat    2340
aataaatgtc caggaatcag agctcaaact cagatcctta gtcttaaact ccagtccctt    2400
ttcttcctaa ctccaagacc ttggagtaag atcttgtggc tgtaggtatg gctgatgccc    2460
tgaagagttg aagttggcag ggaaggtgcc cagaaaattt tggattgaag atttcatggc    2520
aagtctctgg ccagtggcct agcccgggta agccatgcta tgctcacctc cccacagccc    2580
cctctcgcct tttttttt tttttttac cttgactgga agcacaagca gaaactggga      2640
catgagcacc aggagaccag atttccatgg tcccgttggg ggcatgggggt tggggagagg   2700 ttgcagagga gggctctgga ggggagcaac tgtcacagct gtgagaggtg ggggtgagca    2760
ggcagtcagg gctgttccct ccagaatcct ggggtgtcct ctgcacttct gcgccaagct    2820
ggagtgctag tgtgatggac aaggtggtaa gagagctgaa agagcacgag cataacaaga    2880
aagacagagg cagaagcaaa aaaaaaaaa aaaaaaaca gagggcaaca gagagacagt    2940
tacagagact acagtgatcc acagagggag agccatccct gtgaattagc catcatttcc    3000
ctgtaaacct tagaacccag ctgttgccag ggcaacgggg caatacctgt ctctctagag    3060
atgaagttgc cagggtaact gcatcctgtc attcgttcct ggggaccatc cggaatgcgg    3120
cacccactgg ctgttaccat ggcaactgcc tttttgcccc acttaatccc atcccgtctg    3180
ctacaagggc cccacagttg gaggtggggg aagtgggaag agaaaagatc acttgtggac    3240
aaagtttgct ctattccacc tcctccaggc cctccttggg tccatcaccc caggggtgct    3300
gggtccatcc caccccagg cccacacagg cttgcagtat tgtgtgcggt atggtcaggg    3360
cgtccgagag caggtttcgc agtggaaggc aggcaggtgt tggggaggca gttaccgggg    3420
caacgggaac agggcgtttt ggaggtggtt gccatgggga cctggatgct gacgaaggct    3480
cgcgaggctg tgagcagcca cagtgccctg ctcagaagcc ccgggctcgt cagtcaaacc    3540
ggttctctgt ttgcactcgg cagcacgggc aggcaagtgg tccctaggtt cgggagcaga    3600
gcagcagcgc cggatccgcc accatgaccg tgatgagcgg cgagaacgtg gacgaggcct    3660
ctgccgctcc tggacaccct caggatggca gctatcccag acaggccgac cacgacgatc    3720
acgagtgctg cgagcgggtc gtgatcaaca tcagcggcct gagattcgag acacagctga    3780 aaacccctggc ccagttcccc aacaccctgc tgggcaaccc caagaaacgg atgcggtact    3840 tcgacccct gcggaacgag tacttcttcg accggaaccg gcccagcttc gacgccatcc    3900
tgtactacta ccagagcggc ggcagactgc ggaggcccgt gaatgtgccc ctggacatgt    3960
tcagcgagga aatcaagttc tacgagctgg gcgaggaagc catggaaaag ttcagagagg    4020
acgagggctt catcaaagag gaagagaggc ccctgcccga gaaagaatac cagagacaag    4080
```

```
tgtggctgct gttcgagtac cccgagtcta gcggccctgc cagagtgatc gccatcgtgt    4140
ccgtgatggt catcctgatc tctatcgtga tcttctgcct ggaaaccctg cctgagctga    4200
aggacgacaa ggacttcacc ggcaccgtgc accggatcga caacaccacc gtgatctaca    4260
acagcaatat cttcaccgac ccattcttca tcgtggaaac actgtgcatc atctggttca    4320
gcttcgagct ggtcgtgcgg ttcttcgcct gccccagcaa gaccgacttc ttcaagaaca    4380
tcatgaactt cattgatatc gtggccatca tcccctactt catcaccctg gcaccgaga     4440 tcgccgagca ggaaggcaat cagaagggcg agcaggccac cagcctggcc attctgagag    4500
tgatcagact cgtgcgggtg ttccggatct caagctgag ccggcacagc aagggcctgc     4560
agatcctggg ccagacactg aaggccagca tgagagagct gggcctgctg atcttctttc    4620
tgttcatcgg cgtgatcctg ttcagcagcc cgtgtactt cgccgaggcc gaagaagccg     4680
agagccactt cagctctatc cccgacgcct tttggtgggc cgtggtgtcc atgaccacag    4740
tgggctacgg cgacatggtg cccgtgacaa tcggcggcaa gatcgtgggc agcctgtgtg    4800
ccattgccgg cgtgctgaca gtcgccctgc ctgtgcctgt gatcgtgtcc aacttcaact    4860
acttctacca ccgggaaacc gagggggagg aacaggctca gctgctgcac gtgtccagcc    4920
ccaatctggc cagcgacagc gacctgagca gacggtctag cagcaccatg agcaagagcg    4980
agtacatgga aatcgaagag gacatgaaca actctatcgc ccactaccgc caagtgaaca    5040
tccggaccgc caactgcacc accgccaacc agaactgcgt gaacaagagc aagctgctga    5100
ccgatgtctg agtcgacaat caacctctgg attacaaaat tgtgaaaga ttgactggta     5160 ttcttaacta tgttgctcct tttacgctat gtggatacgc tgctttaatg cctttgtatc    5220
atgctattgc ttcccgtatg gctttcattt tctcctcctt gtataaatcc tggttgctgt    5280
ctctttatga ggagttgtgg cccgttgtca ggcaacgtgg cgtggtgtgc actgtgtttg    5340
ctgacgcaac ccccactggt tggggcattg ccaccacctg tcagctcctt tccgggactt    5400
tcgctttccc cctccctatt gccacggcgg aactcatcgc cgcctgcctt gcccgctgct    5460 ggacagggc tcggctgttg ggcactgaca attccgtggt gttgtcgggg aaatcatcgt     5520
cctttccttg gctgctcgcc tgtgttgcca cctggattct gcgcgggacg tccttctgct    5580
acgtcccttc ggccctcaat ccagcggacc ttccttcccg cggcctgctg ccggctctgc    5640
ggcctcttcc gcgtcttcgc cttcgccctc agacgagtcg atctcccctt gggccgcct   5700 ccccgcctgg aattcgagct cggtaccttt aagaccaatg acttacaagg cagctgtaga    5760
tcttagccac ttttttaaaag aaaaggggg actggaaggg ctaattcact cccaacgaag    5820
acaagatctg cttttttgctt gtactgggtc tctctggtta gaccagatct gagcctggga   5880
gctctctggc taactaggga acccactgct taagcctcaa taaagcttgc cttgagtgct    5940
tcaagtagtg tgtgcccgtc tgttgtgtga ctctggtaac tagagatccc tcagaccctt    6000
ttagtcagtg tggaaaatct ctagca                                         6026
```

<210> SEQ ID NO 12
<211> LENGTH: 9357
<212> TYPE: DNA
<213> ORGANISM: Artificial Sequence
<220> FEATURE:
<223> OTHER INFORMATION: exemplary engineered KCNA1 gene viral vector lacking a reporter (with bacterial plasmid portion) encoding an edited Kv1.1 potassium channel with Y379V mutation

<400> SEQUENCE: 12

```
taaataaata aataaataat ataaataata aatgtccagg aatcagagct caaactcaga     60
```

```
tccttagtct taaactccag tcccttttct tcctaactcc aagaccttgg agtaagatct      120
tgtggctgta ggtatggctg atgccctgaa gagttgaagt tggcagggaa ggtgcccaga      180
aaattttgga ttgaagattt catggcaagt ctctggccag tggcctagcc cgggtaagcc      240
atgctatgct caccccccca cagcccccct tcgcctttt tttttttttt ttttaccttg      300
actggaagca caagcagaaa ctgggacatg agcaccagga gaccagattt ccatggtccc      360 gttggggca tggggttggg gagaggttgc agaggagggc tctggagggg agcaactgtc       420
acagctgtga gaggtgggggg tgagcaggca gtcagggctg ttccctccag aatcctgggg     480
tgtcctctgc acttctgcgc caagctggag tgctagtgtg atggacaagg tggtaagaga      540
gctgaaagag cacgagcata caagaaaga cagaggcaga agcaaaaaaa aaaaaaaaaa       600
aaaacagagg gcaacagaga gacagttaca gagactacag tgatccacag agggagagcc      660
atccctgtga attagccatc atttccctgt aaaccttaga acccagctgt tgccagggca      720
acggggcaat acctgtctct ctagagatga agttgccagg gtaactgcat cctgtcattc      780
gttcctgggg accatccgga atgcggcacc cactggctgt taccatggca actgcctttt     840
tgccccactt aatcccatcc cgtctgctac aagggcccca cagttggagg tgggggaggt      900
gggaagagaa aagatcactt gtggacaaag tttgctctat tccacctcct ccaggccctc      960
cttgggtcca tcaccccagg ggtgctgggt ccatcccacc cccaggccca cacaggcttg     1020
cagtattgtg tgcggtatgg tcagggcgtc cgagagcagg tttcgcagtg gaaggcaggc    1080
aggtgttggg gaggcagtta ccggggcaac gggaacaggg cgttttggag gtggttgcca    1140
tggggacctg gatgctgacg aaggctcgcg aggctgtgag cagccacagt gccctgctca    1200
gaagccccgg gctcgtcagt caaaccggtt ctctgtttgc actcggcagc acgggcaggc    1260
aagtggtccc taggttcggg agcagagcag cagcgccgga tccgccacca tgaccgtgat    1320
gagcggcgag aacgtggacg aggcctctgc cgctcctgga cacctcagg atggcagcta    1380 tcccagacag gccgaccacg acgatcacga gtgctgcgag cgggtcgtga tcaacatcag    1440
cggcctgaga ttcgagacac agctgaaaac cctggcccag ttcccaaca ccctgctggg    1500 caaccccaag aaacggatgc ggtacttcga ccccctgcgg aacgagtact tcttcgaccg    1560
gaaccggccc agcttcgacg ccatcctgta ctactaccag agcggcggca gactgcggag    1620
gcccgtgaat gtgcccctgg acatgttcag cgaggaaatc aagttctacg agctgggcga    1680
ggaagccatg gaaaagttca gagaggacga gggcttcatc aaagaggaag agaggcccct    1740
gcccgagaaa gaataccaga gacaagtgtg gctgctgttc gagtaccccg agtctagcgg    1800
ccctgccaga gtgatcgcca tcgtgtccgt gatggtcatc ctgatctcta tcgtgatctt    1860
ctgcctggaa accctgcctg agctgaagga cgacaaggac ttcaccggca ccgtgcaccg    1920
gatcgacaac accaccgtga tctacaacag caatatcttc accgacccat tcttcatcgt    1980
ggaaacactg tgcatcatct ggttcagctt cgagctggtc gtgcggttct tcgcctgccc    2040
cagcaagacc gacttcttca gaacatcat gaacttcatt gatatcgtgg ccatcatccc    2100
ctacttcatc accctgggca ccgagatcgc cgagcaggaa ggcaatcaga agggcgagca    2160
ggccaccagc ctggccattc tgagagtgat cagactcgtg cgggtgttcc ggatcttcaa    2220
gctgagccgg cacagcaagg gcctgcagat cctgggccag acactgaagg ccagcatgag    2280
agagctgggc ctgctgatct tctttctgtt catcggcgtg atcctgttca gcagcgccgt    2340
gtacttcgcc gaggccgaag aagccgagag ccacttcagc tctatccccg acgccttttg    2400
```

```
gtgggccgtg gtgtccatga ccacagtggg ctacggcgac atggtgcccg tgacaatcgg   2460
cggcaagatc gtgggcagcc tgtgtgccat tgccggcgtg ctgacagtcg ccctgcctgt   2520
gcctgtgatc gtgtccaact tcaactactt ctaccaccgg gaaaccgagg gggaggaaca   2580
ggctcagctg ctgcacgtgt ccagccccaa tctggccagc gacagcgacc tgagcagacg   2640
gtctagcagc accatgagca agagcgagta catggaaatc gaagaggaca tgaacaactc   2700
tatcgcccac taccgccaag tgaacatccg gaccgccaac tgcaccaccg ccaaccagaa   2760
ctgcgtgaac aagagcaagc tgctgaccga tgtctgagtc gacaatcaac ctctggatta   2820
caaaatttgt gaaagattga ctggtattct taactatgtt gctcctttta cgctatgtgg   2880
atacgctgct ttaatgcctt tgtatcatgc tattgcttcc cgtatggctt tcattttctc   2940
ctccttgtat aaatcctggt tgctgtctct ttatgaggag ttgtggcccg ttgtcaggca   3000
acgtggcgtg gtgtgcactg tgtttgctga cgcaaccccc actggttggg gcattgccac   3060
cacctgtcag ctcctttccg ggactttcgc tttcccccctс cctattgcca cggcggaact   3120
catcgccgcc tgccttgccc gctgctggac agggggctcgg ctgttgggca ctgacaattc   3180
cgtggtgttg tcggggaaat catcgtcctt tccttggctg ctcgcctgtg ttgccacctg   3240
gattctgcgc gggacgtcct tctgctacgt cccttcggcc ctcaatccag cggaccttcc   3300
ttcccgcggc ctgctgccgg ctctgcggcc tcttccgcgt cttcgccttc gccctcagac   3360
gagtcggatc tccctttggg ccgcctcccc gcctggaatt cgagctcggt acctttaaga   3420
ccaatgactt acaaggcagc tgtagatctt agccactttt taaagaaaaa gggggggactg   3480 gaagggctaa ttcactccca acgaagacaa gatctgcttt ttgcttgtac tgggtctctc   3540
tggttagacc agatctgagc ctgggagctc tctggctaac tagggaaccc actgcttaag   3600
cctcaataaa gcttgccttg agtgcttcaa gtagtgtgtg cccgtctgtt gtgtgactct   3660
ggtaactaga gatccctcag accctttttag tcagtgtgga aaatctctag cagtagtagt   3720
tcatgtcatc ttattattca gtatttataa cttgcaaaga aatgaatatc agagagtgag   3780
aggaacttgt ttattgcagc ttataatggt tacaaataaa gcaatagcat cacaaatttc   3840
acaaataaag cattttttttс actgcattct agttgtggtt tgtccaaact catcaatgta   3900
tcttatcatg tctggctcta gctatcccgc ccctaactcc gcccatcccg cccctaactc   3960
cgcccagttc cgcccattct ccgccccatg gctgactaat ttttttttатt tatgcagagg   4020 ccgaggccgc ctcggcctct gagctattcc agaagtagtg aggaggcttt tttggaggcc   4080
tagggacgta cccaattcgc cctatagtga gtcgtattac gcgcgctcac tggccgtcgt   4140
tttacaacgt cgtgactggg aaaaccctgg cgttacccaa cttaatcgcc ttgcagcaca   4200
tccccctttc gccagctggc gtaatagcga agaggcccgc accgatcgcc cttcccaaca   4260
gttgcgcagc ctgaatggcg aatgggacgc gccctgtagc ggcgcattaa gcgcggcggg   4320
tgtggtggtt acgcgcagcg tgaccgctac acttgccagc gccctagcgc ccgctccttt   4380
cgctttcttc ccttcctttc tcgccacgtt cgccggcttt ccccgtcaag ctctaaatcg   4440
ggggctccct ttagggttcc gatttagtgc tttacggcac ctcgacccca aaaaacttga   4500
ttagggtgat ggttcacgta gtgggccatc gccctgatag acggtttttc gccctttgac   4560
gttggagtcc acgttcttta atagtggact cttgttccaa actggaacaa cactcaaccc   4620
tatctcggtc tattcttttg atttataagg gattttgccg atttcggcct attggttaaa   4680
aaatgagctg atttaacaaa aatttaacgc gaattttaac aaaatattaa cgcttacaat   4740
ttaggtggca cttttcgggg aaatgtgcgc ggaaccccta tttgtttatt tttctaaata   4800
```

```
cattcaaata tgtatccgct catgagacaa taaccctgat aaatgcttca ataatagcac   4860
ctagatcaag agacaggatg aggatcgttt cgcatgattg aacaagatgg attgcacgca   4920
ggttctccgg ccgcttgggt ggagaggcta ttcggctatg actgggcaca acagacaatc   4980
ggctgctctg atgccgccgt gttccggctg tcagcgcagg ggcgcccggt tcttttgtc    5040 aagaccgacc tgtccggtgc cctgaatgaa ctgcaagacg aggcagcgcg gctatcgtgg   5100
ctggccacga cgggcgttcc ttgcgcagct gtgctcgacg ttgtcactga agcgggaagg   5160
gactggctgc tattgggcga agtgccgggg caggatctcc tgtcatctca ccttgctcct   5220
gccgagaaag tatccatcat ggctgatgca atgcggcggc tgcatacgct tgatccggct   5280
acctgcccat tcgaccacca agcgaaacat cgcatcgagc gagcacgtac tcggatggaa   5340
gccggtcttg tcgatcagga tgatctggac gaagagcatc aggggctcgc gccagccgaa   5400
ctgttcgcca ggctcaaggc gagcatgccc gacggcgagg atctcgtcgt gacccatggc   5460
gatgcctgct tgccgaatat catggtggaa aatggccgct tttctggatt catcgactgt   5520
ggccggctgg gtgtggcgga ccgctatcag gacatagcgt tggctacccg tgatattgct   5580
gaagagcttg gcggcgaatg ggctgaccgc ttcctcgtgc tttacggtat cgccgctccc   5640
gattcgcagc gcatcgcctt ctatcgcctt cttgacgagt tcttctgaat tattaacgct   5700
tacaatttcc tgatgcggta ttttctcctt acgcatctgt gcggtatttc acaccgcatc   5760
aggtggcact tttcggggaa atgtgcgcgg aacccctatt tgtttatttt tctaaataca   5820
ttcaaatatg tatccgctca tgaccaaaat cccttaacgt gagttttcgt tccactgagc   5880
gtcagacccc gtagaaaaga tcaaaggatc ttcttgagat cctttttttc tgcgcgtaat   5940
ctgctgcttg caaacaaaaa aaccaccgct accagcggtg gtttgtttgc cggatcaaga   6000
gctaccaact ctttttccga aggtaactgg cttcagcaga gcgcagatac caaatactgt   6060
tcttctagtg tagccgtagt taggccacca cttcaagaac tctgtagcac cgcctacata   6120
cctcgctctg ctaatcctgt taccagtggc tgctgccagt ggcgataagt cgtgtcttac   6180
cgggttggac tcaagacgat agttaccgga taaggcgcag cggtcgggct gaacggggggg   6240 gtcgtgcaca cagcccagct tggagcgaac gacctacacc gaactgagat acctacagcg   6300
tgagctatga gaaagcgcca cgcttcccga agggagaaag gcggacaggt atccggtaag   6360
cggcagggtc ggaacaggag agcgcacgag ggagcttcca gggggaaacg cctggtatct   6420
ttatagtcct gtcgggtttc gccacctctg acttgagcgt cgatttttgt gatgctcgtc   6480
aggggggcgg agcctatgga aaaacgccag caacgcggcc ttttacggt tcctggcctt    6540 ttgctggcct tttgctcaca tgttctttcc tgcgttatcc cctgattctg tggataaccg   6600
tattaccgcc tttgagtgag ctgataccgc tcgccgcagc cgaacgaccg agcgcagcga   6660
gtcagtgagc gaggaagcgg aagagcgccc aatacgcaaa ccgcctctcc ccgcgcgttg   6720
gccgattcat taatgcagct ggcacgacag gtttcccgac tggaaagcgg gcagtgagcg   6780
caacgcaatt aatgtgagtt agctcactca ttaggcaccc caggctttac actttatgct   6840
tccggctcgt atgttgtgtg gaattgtgag cggataacaa tttcacacag gaaacagcta   6900
tgaccatgat tacgccaagc gcgcaattaa ccctcactaa agggaacaaa agctggagct   6960
gcaagcttgg ccattgcata cgttgtatcc atatcataat atgtacattt atattggctc   7020
atgtccaaca ttaccgccat gttgacattg attattgact agttattaat agtaatcaat   7080
tacggggtca ttagttcata gcccatatat ggagttccgc gttacataac ttacggtaaa   7140
```

```
tggcccgcct ggctgaccgc ccaacgaccc ccgcccattg acgtcaataa tgacgtatgt   7200
tcccatagta acgccaatag ggactttcca ttgacgtcaa tgggtggagt atttacggta   7260
aactgcccac ttggcagtac atcaagtgta tcatatgcca agtacgcccc ctattgacgt   7320
caatgacggt aaatggcccg cctggcatta tgcccagtac atgaccttat gggactttcc   7380
tacttggcag tacatctacg tattagtcat cgctattacc atggtgatgc ggttttggca   7440
gtacatcaat gggcgtggat agcggtttga ctcacgggga tttccaagtc tccaccccat   7500
tgacgtcaat gggagtttgt tttggcacca aaatcaacgg gactttccaa aatgtcgtaa   7560
caactccgcc ccattgacgc aaatgggcgg taggcgtgta cggtgggagg tctatataag   7620
cagagctcgt ttagtgaacc ggggtctctc tggttagacc agatctgagc ctgggagctc   7680
tctggctaac tagggaaccc actgcttaag cctcaataaa gcttgccttg agtgcttcaa   7740
gtagtgtgtg cccgtctgtt gtgtgactct ggtaactaga gatccctcag accctttttag   7800 tcagtgtgga aaatctctag cagtggcgcc cgaacaggga cttgaaagcg aaagggaaac   7860
cagaggagct ctctcgacgc aggactcggc ttgctgaagc gcgcacggca agaggcgagg   7920
ggcggcgact ggtgagtacg ccaaaaattt tgactagcgg aggctagaag gagagagatg   7980
ggtgcgagag cgtcagtatt aagcggggga gaattagatc gcgatgggaa aaaattcggt   8040
taaggccagg gggaaagaaa aaatataaat taaaacatat agtatgggca agcagggagc   8100
tagaacgatt cgcagttaat cctggcctgt tagaaacatc agaaggctgt agacaaatac   8160
tgggacagct acaaccatcc cttcagacag gatcagaaga acttagatca ttatataata   8220
cagtagcaac cctctattgt gtgcatcaaa ggatagagat aaaagacacc aaggaagctt   8280
tagacaagat agaggaagag caaaacaaaa gtaagaccac cgcacagcaa gcggccgctg   8340
atcttcagac ctggaggagg agatatgagg gacaattgga gaagtgaatt atataaatat   8400
aaagtagtaa aaattgaacc attaggagta gcacccacca aggcaaagag aagagtggtg   8460
cagagagaaa aaagagcagt gggaatagga gctttgttcc ttgggttctt gggagcagca   8520
ggaagcacta tgggcgcagc gtcaatgacg ctgacggtac aggccagaca attattgtct   8580
ggtatagtgc agcagcagaa caatttgctg agggctattg aggcgcaaca gcatctgttg   8640
caactcacag tctggggcat caagcagctc caggcaagaa tcctggctgt ggaaagatac   8700
ctaaaggatc aacagctcct ggggatttgg ggttgctctg gaaaactcat ttgcaccact   8760
gctgtgcctt ggaatgctag ttggagtaat aaatctctgg aacagatttg gaatcacacg   8820
acctggatgg agtgggacag agaaattaac aattacacaa gcttaataca ctccttaatt   8880
gaagaatcgc aaaaccagca agaaaagaat gaacaagaat tattggaatt agataaatgg   8940
gcaagtttgt ggaattggtt taacataaca aattggctgt ggtatataaa attattcata   9000
atgatagtag gaggcttggt aggtttaaga atagtttttg ctgtactttc tatagtgaat   9060
agagttaggc agggatattc accattatcg tttcagaccc acctcccaac cccgagggga   9120
cccgacaggc ccgaaggaat agaagaagaa ggtggagaga gagacagaga cagatccatt   9180
cgattagtga acggatctcg acggtatcgg ttaacttttta aagaaaagg ggggattggg   9240 gggtacagtg caggggaaag aatagtagac ataatagcaa cagacataca aactaaagaa   9300
ttacaaaaac aaattacaaa attcaaaatt ttatcgaatt ccacgggggtt aatcgaa    9357
```

<210> SEQ ID NO 13
<211> LENGTH: 1488
<212> TYPE: DNA
<213> ORGANISM: Artificial Sequence
<220> FEATURE:
<223> OTHER INFORMATION: exemplary engineered human KCNA1 gene encoding
an edited Kv1.1 with a Y379V substitution

<400> SEQUENCE: 13

```
atgaccgtga tgagcggcga gaacgtggac gaggcctctg ccgctcctgg acaccctcag     60
gatggcagct atcccagaca ggccgaccac gacgatcacg agtgctgcga gcgggtcgtg    120
atcaacatca gcggcctgag attcgagaca cagctgaaaa ccctggccca gttccccaac    180
accctgctgg gcaaccccaa gaaacggatg cggtacttcg accccctgcg gaacgagtac    240
ttcttcgacc ggaaccggcc cagcttcgac gccatcctgt actactacca gagcggcggc    300
agactgcgga ggcccgtgaa tgtgcccctg gacatgttca gcgaggaaat caagttctac    360
gagctgggcg aggaagccat ggaaaagttc agagaggacg agggcttcat caaagaggaa    420
gagaggcccc tgcccgagaa agaataccag agacaagtgt ggctgctgtt cgagtacccc    480
gagtctagcg gccctgccag agtgatcgcc atcgtgtccg tgatggtcat cctgatctct    540
atcgtgatct tctgcctgga aaccctgcct gagctgaagg acgacaagga cttcaccggc    600
accgtgcacc ggatcgacaa caccaccgtg atctacaaca gcaatatctt caccgaccca    660
ttcttcatcg tggaaacact gtgcatcatc tggttcagct tcgagctggt cgtgcggttc    720
ttcgcctgcc ccagcaagac cgacttcttc aagaacatca tgaacttcat tgatatcgtg    780
gccatcatcc cctacttcat caccctgggc accgagatcg ccgagcagga aggcaatcag    840
aagggcgagc aggccaccag cctggccatt ctgagagtga tcagactcgt gcgggtgttc    900
cggatcttca agctgagccg gcacagcaag ggcctgcaga tcctgggcca gacactgaag    960
gccagcatga gagagctggg cctgctgatc ttctttctgt tcatcggcgt gatcctgttc   1020
agcagcgccg tgtacttcgc cgaggccgaa gaagccgaga gccacttcag ctctatcccc   1080
gacgcctttt ggtgggccgt ggtgtccatg accacagtgg gctacggcga catggtgccc   1140
gtgacaatcg gcggcaagat cgtgggcagc ctgtgtgcca ttgccggcgt gctgacagtc   1200
gccctgcctg tgcctgtgat cgtgtccaac ttcaactact tctaccaccg ggaaaccgag   1260
ggggaggaac aggctcagct gctgcacgtg tccagcccca atctggccag cgacagcgac   1320
ctgagcagac ggtctagcag caccatgagc aagagcgagt acatggaaat cgaagaggac   1380
atgaacaact ctatcgccca ctaccgccaa gtgaacatcc ggaccgccaa ctgcaccacc   1440
gccaaccaga actgcgtgaa caagagcaag ctgctgaccg atgtctga                1488
```

<210> SEQ ID NO 14
<211> LENGTH: 495
<212> TYPE: PRT
<213> ORGANISM: Artificial Sequence
<220> FEATURE:
<223> OTHER INFORMATION: edited human Kv1.1

<400> SEQUENCE: 14

```
Met Thr Val Met Ser Gly Glu Asn Val Asp Glu Ala Ser Ala Ala Pro
1               5                   10                  15

Gly His Pro Gln Asp Gly Ser Tyr Pro Arg Gln Ala Asp His Asp Asp
            20                  25                  30

His Glu Cys Cys Glu Arg Val Val Ile Asn Ile Ser Gly Leu Arg Phe
        35                  40                  45

Glu Thr Gln Leu Lys Thr Leu Ala Gln Phe Pro Asn Thr Leu Leu Gly
    50                  55                  60

Asn Pro Lys Lys Arg Met Arg Tyr Phe Asp Pro Leu Arg Asn Glu Tyr
```

```
               65                  70                  75                  80
        Phe Phe Asp Arg Asn Arg Pro Ser Phe Asp Ala Ile Leu Tyr Tyr Tyr
                            85                  90                  95

Gln Ser Gly Gly Arg Leu Arg Arg Pro Val Asn Val Pro Leu Asp Met
                        100                 105                 110

Phe Ser Glu Glu Ile Lys Phe Tyr Glu Leu Gly Glu Glu Ala Met Glu
                        115                 120                 125

Lys Phe Arg Glu Asp Glu Gly Phe Ile Lys Glu Glu Arg Pro Leu
                    130                 135                 140

Pro Glu Lys Glu Tyr Gln Arg Gln Val Trp Leu Leu Phe Glu Tyr Pro
        145                 150                 155                 160

Glu Ser Ser Gly Pro Ala Arg Val Ile Ala Ile Val Ser Val Met Val
                        165                 170                 175

Ile Leu Ile Ser Ile Val Ile Phe Cys Leu Glu Thr Leu Pro Glu Leu
                        180                 185                 190

Lys Asp Asp Lys Asp Phe Thr Gly Thr Val His Arg Ile Asp Asn Thr
                    195                 200                 205

Thr Val Ile Tyr Asn Ser Asn Ile Phe Thr Asp Pro Phe Phe Ile Val
                    210                 215                 220

Glu Thr Leu Cys Ile Ile Trp Phe Ser Phe Glu Leu Val Val Arg Phe
        225                 230                 235                 240

Phe Ala Cys Pro Ser Lys Thr Asp Phe Phe Lys Asn Ile Met Asn Phe
                        245                 250                 255

Ile Asp Ile Val Ala Ile Ile Pro Tyr Phe Ile Thr Leu Gly Thr Glu
                    260                 265                 270

Ile Ala Glu Gln Glu Gly Asn Gln Lys Gly Glu Gln Ala Thr Ser Leu
                    275                 280                 285

Ala Ile Leu Arg Val Ile Arg Leu Val Arg Val Phe Arg Ile Phe Lys
                    290                 295                 300

Leu Ser Arg His Ser Lys Gly Leu Gln Ile Leu Gly Gln Thr Leu Lys
        305                 310                 315                 320

Ala Ser Met Arg Glu Leu Gly Leu Leu Ile Phe Phe Leu Phe Ile Gly
                        325                 330                 335

Val Ile Leu Phe Ser Ser Ala Val Tyr Phe Ala Glu Ala Glu Ala
                        340                 345                 350

Glu Ser His Phe Ser Ser Ile Pro Asp Ala Phe Trp Trp Ala Val Val
                    355                 360                 365

Ser Met Thr Thr Val Gly Tyr Gly Asp Met Val Pro Thr Ile Gly
                    370                 375                 380

Gly Lys Ile Val Gly Ser Leu Cys Ala Ile Ala Gly Val Leu Thr Val
        385                 390                 395                 400

Ala Leu Pro Val Pro Val Ile Val Ser Asn Phe Asn Tyr Phe Tyr His
                        405                 410                 415

Arg Glu Thr Glu Gly Glu Glu Gln Ala Gln Leu Leu His Val Ser Ser
                        420                 425                 430

Pro Asn Leu Ala Ser Asp Ser Asp Leu Ser Arg Arg Ser Ser Ser Thr
                    435                 440                 445

Met Ser Lys Ser Glu Tyr Met Glu Ile Glu Glu Asp Met Asn Asn Ser
                    450                 455                 460
```

```
Ile Ala His Tyr Arg Gln Val Asn Ile Arg Thr Ala Asn Cys Thr Thr
465                 470                 475                 480

Ala Asn Gln Asn Cys Val Asn Lys Ser Lys Leu Leu Thr Asp Val
                485                 490                 495
```